United States Patent
Wu et al.

(10) Patent No.: US 7,318,928 B2
(45) Date of Patent: Jan. 15, 2008

(54) MOLECULAR VACCINE LINKING INTERCELLULAR SPREADING PROTEIN TO AN ANTIGEN

(75) Inventors: Tzvv-Choou Wu, Brookeville, MD (US); Chien-Fu Hung, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 321 days.

(21) Appl. No.: 10/343,719

(22) PCT Filed: Aug. 1, 2001

(86) PCT No.: PCT/US01/23966

§ 371 (c)(1),
(2), (4) Date: Aug. 8, 2003

(87) PCT Pub. No.: WO02/09645

PCT Pub. Date: Feb. 7, 2002

(65) Prior Publication Data

US 2004/0028693 A1    Feb. 12, 2004

Related U.S. Application Data

(60) Provisional application No. 60/281,004, filed on Apr. 4, 2001, provisional application No. 60/268,575, filed on Feb. 15, 2001, provisional application No. 60/222,185, filed on Aug. 1, 2000.

(51) Int. Cl.
*A61K 39/12* (2006.01)
(52) U.S. Cl. .............................. 424/199.1; 424/204.1; 424/229.1
(58) Field of Classification Search ............. 424/199.1, 424/204.1, 229.1; 435/69.1, 320.1
See application file for complete search history.

(56) References Cited

U.S. PATENT DOCUMENTS 6,017,735 A * 1/2000 O'Hare et al. ............... 435/325

FOREIGN PATENT DOCUMENTS

WO    WO 98 32866 A1    7/1998

OTHER PUBLICATIONS

Michel Nico et al. "Improved Immunogenicity of Human Papillomavirus Type 16 E7 DNA After Fusion to the Herpes Simplex Virus 1 VP22 Gene" Barcelona, Spain, Jul. 23-28, 2000, Abstract 458, XP002201712.
Michel Nico et al. "Enhanced Immunogenicity of HPV 16 E7 Fusion Proteins in DNA Vaccination" Virology vol. 294, pp. 47-59, 2002, XP002201708.
Wolfgang W. Leitner, et al. "DNA and RNA-Based Vaccines: Principles, Progress and Prospects" Vaccine, vol. 18, pp. 765-777, Dec. 10, 1999, XP002201709.
G.J.P. Fernando et al. "Expression, Purification and Immunological Characterization of the Transforming Protein E7, From Cervical Cancer-Associated Human Papillomavirus Type 16" Clin. Exp. Immunol, vol. 115, pp. 397-403, 1999, XP002201710.
Wen-Fang Cheng et al. "Enhancement of Sindbis Virus Self-Replicating RNA Vaccine Potency by Linkage of Herpes Simplex Virus Type 1 VP22 Protein to Antigen" Journal of Virology, vol. 75, No. 5, pp. 2368-2376, Mar. 2001-03, XP002201711.
Gillian Elliott, et al., "Intercellular Trafficking and Protein Delivery by a Herpesvirus Structural Protein", http://www.cell.com/cgi/content/full88/2/223/, Cell, vol. 88, 223-233, Jan. 1997, 12 pages.

* cited by examiner

*Primary Examiner*—Ali R. Salimi
(74) *Attorney, Agent, or Firm*—Foley Hoag LLP

(57) ABSTRACT

Superior molecular vaccines comprise nucleic acids, including naked DNA and replicon RNA, that encode a fusion polypeptide that includes an antigenic peptide or polypeptide against which an immune response is desired. Fused to the antigenic peptide is an intercellular spreading protein, in particular a herpes virus protein VP22 or a homologue or functional derivative thereof. Preferred spreading proteins are VP22 from HSV-1 and Marek's disease virus. The nucleic acid can encode any antigenic epitope of interest, preferably an epitope that is processed and presented by MHC class I proteins. Antigens of pathogenic organisms and cells such as tumor cells are preferred. Vaccines comprising HPV-16 E7 oncoprotein are exemplified. Also disclosed are methods of using the vaccines to induce heightened T cell mediated immunity, in particular by cytotoxic T lymphocytes, leading to protection from or treatment of a tumor.

9 Claims, 21 Drawing Sheets

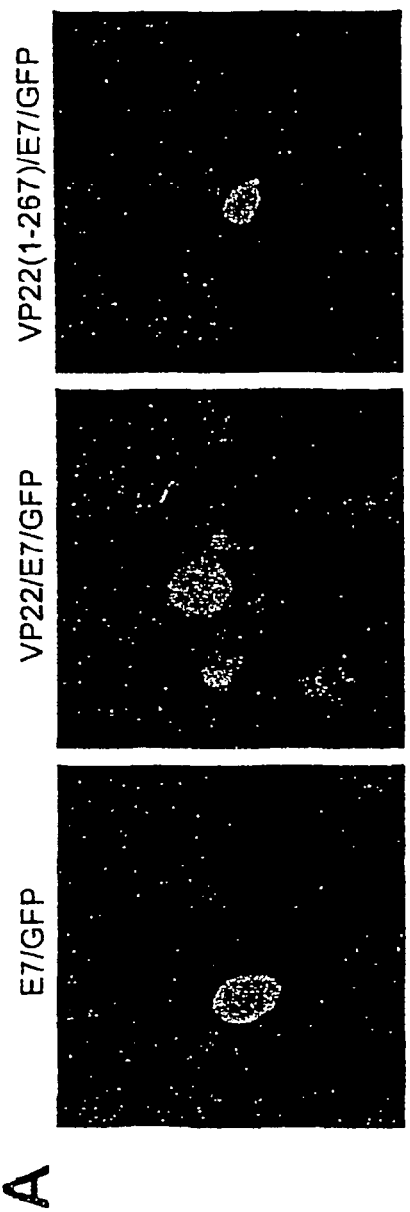
Fig. 1

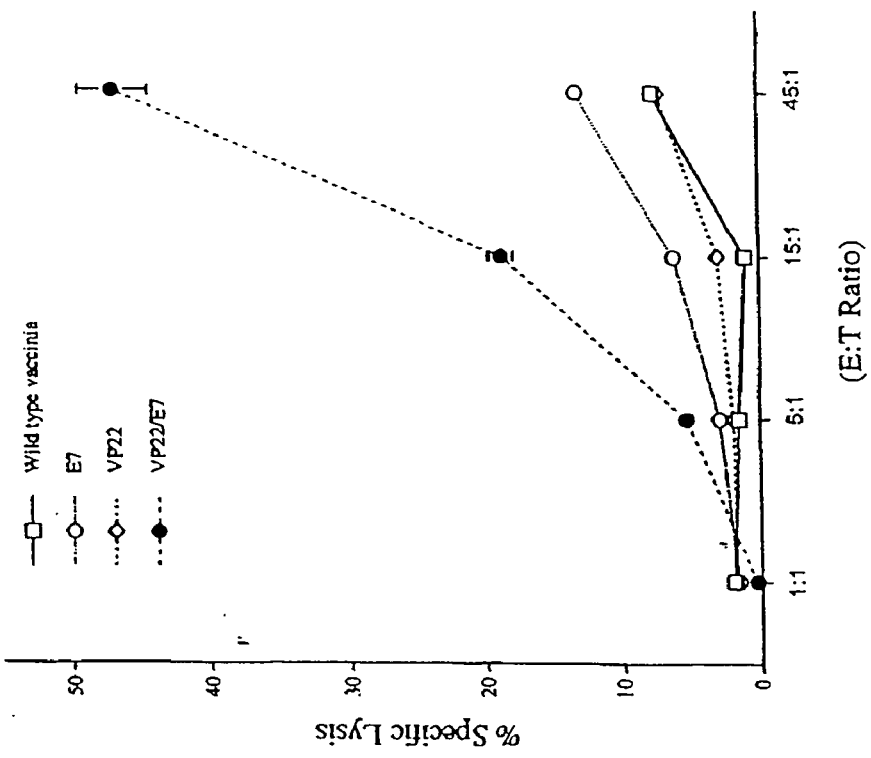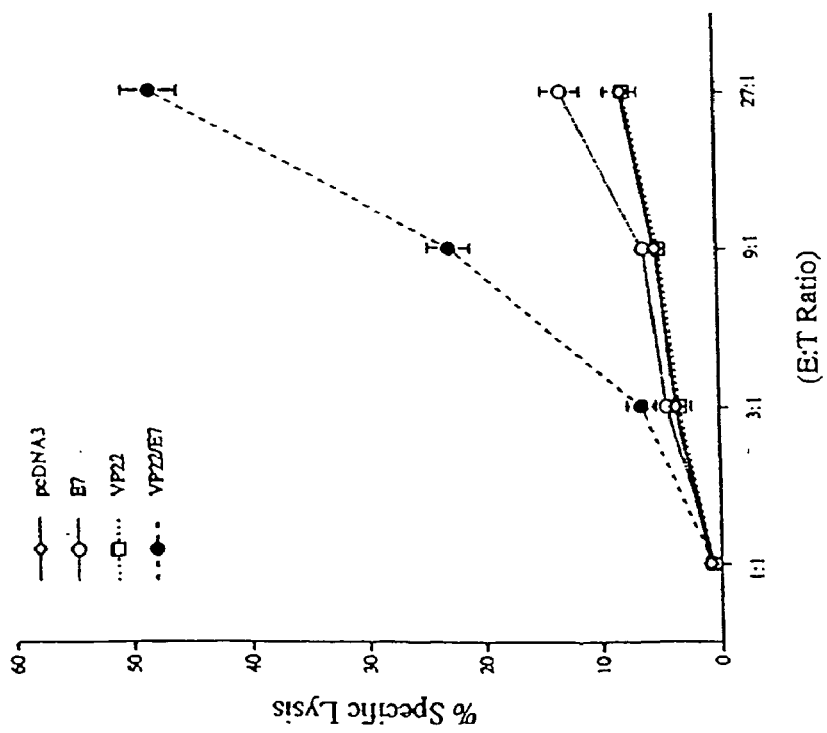
Fig. 4

```
ATG ACC TCT CGC CGC TCC GTG AAG TCG GGT CCG CGG GAG GTT CCG CGC GAT GAG TAC GAG
Met thr ser arg arg ser val lys ser gly pro arg glu val pro arg asp glu tyr glu
61/21                                   91/31
GAT CTG TAC TAC ACC CCG TCT TCA GGT ATG GCG AGT CCC GAT AGT CCG CCT GAC ACC TCC
asp leu tyr tyr thr pro ser ser gly met ala ser pro asp ser pro pro asp thr ser
121/41                                  151/51
CGC CGT GGC GCC CTA CAG ACA CGC TGG CGC CAG AGG GGC GAG GTC CGT TTC GTC CAG TAC
arg arg gly ala leu gln thr arg ser arg gln arg gly glu val arg phe val gln tyr
181/61                                  211/71
CAC GAG TCG GAT TAT GCC CTC TAC GGG GGC TCG TCT TCC GAA GAC GAC GAA CAC CCG GAG
asp glu ser asp tyr ala leu tyr gly gly ser ser ser glu asp asp glu his pro glu
241/81                                  271/91
GTC CCC CGG ACG CGG CGT CCC GTT TCC GGG GCG GTT TTG TCC GGC CCG GGG CCT CGG CGG
val pro arg thr arg arg pro val ser gly ala val leu ser gly pro gly pro ala arg
301/101                                 331/111
GCG CCT CGG CCA CCC GCT GGG TCC GGA GGG GCC GGA CGC ACA CCC ACC ACC GCC CCC CGG
ala pro pro pro ala gly ser gly gly ala gly arg thr pro thr thr ala pro arg
361/121                                 391/131
GCC CCC CGA ACC CAG CGG GTG GCG TCT AAG GCC CCC GCG GCC CGG GCG GCG GAG ACC ACC
ala pro arg thr gln arg val ala ser lys ala pro ala ala pro ala ala glu thr thr
421/141                                 451/151
CGC GGC AGG AAA TCG GCC CAG CCA GAA TCC GCC GCA CTC CCA GAC GCC CCC CCG TCC ACC
arg gly arg lys ser ala gln pro glu ser ala ala leu pro asp ala pro ala ser thr
481/161                                 511/171
GCG CCA ACC CGA TCC AAG ACA CCC GCG CAG GGG CTG GCC AGA AAG CTG CAC TTT AGC ACC
ala pro thr arg ser lys thr pro ala gln gly leu ala arg lys leu his phe ser thr
541/181                                 571/191
GCC CCC CCA AAC CCC GAC GCG CCA TGG ACC CCC CGG GTG GCC GGC TTT AAC AAG CGC GTC
ala pro pro asn pro asp ala pro trp thr pro arg val ala gly phe asn lys arg val
601/201                                 631/211
TTC TGC GCC GCG GTC GGG CGC CTG GCG GCC ATG CAT GCC CGG ATG GCG GCT GTC CAG CTC
phe cys ala ala val gly arg leu ala ala met his ala arg met ala ala val gln leu
661/221                                 691/231
TGG GAC ATG TCG CGT CCG CGC ACA GAC GAA GAC CTC AAC GAA CTC CTT GGC ATC ACC ACC
trp asp met ser arg pro arg thr asp glu asp leu asn glu leu leu gly ile thr thr
721/241                                 751/251
ATC CGC GTG ACG GTC TGC GAG GGC AAA AAC CTG CTT CAG CGC GCC AAC GAG TTG GTG AAT
ile arg val thr val cys glu gly lys asn leu leu gln arg ala asn glu leu val asn
781/261                                 811/271
CCA GAC GTG GTG CAG GAC GTC GAC GCG GCC ACG GCG ACT CGA GGG CGT TCT GCG GCG TCG
pro asp val val gln asp val asp ala ala thr ala thr arg gly arg ser ala ala ser
841/281                                 871/291
CGC CCC ACC GAG CGA CCA CCT CGA GCC CCA GCC CGC TCC GCT TCT CGC CCC AGA CGG CCC GTC
arg pro thr glu arg pro arg ala pro ala arg ser ala ser arg pro arg arg pro val
901/301                                 931/311
GAG GGT ACC GAG CTC GGA TCC atg cat gga gat aca cct aca ttg cat gaa tat atg tta
glu gly thr glu leu gly ser met his gly asp thr pro thr leu his glu tyr met leu
961/321                                 991/331
gat ttg caa cca gag aca act gat ctc tac tgt tat gag caa tta aat gac agc tca gag
asp leu gln pro glu thr thr asp leu tyr cys tyr glu gln leu asn asp ser ser glu
1021/341                                1051/351
gag gag gat gaa ata gat ggt cca gct gga caa gca gaa ccg gac aga gcc cat tac aat
glu glu asp glu ile asp gly pro ala gly gln ala glu pro asp arg ala his tyr asn
1081/361                                1111/371
act gta acc ttt tgt tgc aag tgt gac tct acg ctt cgg ttg tgc gta caa agc aca cac
ile val thr phe cys cys lys cys asp ser thr leu arg leu cys val gln ser thr his
1141/381                                1171/391
gta gac att cgt act ttg gaa gac ctg tta atg ggc aca cta gga att gtg tgc ccc atc
val asp ile arg thr leu glu asp leu leu met gly thr leu gly ile val cys pro ile
1201/401                                1231/411
tgt tct cag gat aag ctt aag ttt aaa ccg cta atc agc ctc gac tgt gcc ttc tag
cys ser gln asp lys leu lys phe lys pro leu ile ser leu asp cys ala phe AMB
```

← SEQ ID NO: 22
← SEQ ID NO: 23

Fig.7

MOLECULAR VACCINE LINKING INTERCELLULAR SPREADING PROTEIN TO AN ANTIGEN

CROSS-REFERENCE TO RELATED APPLICATIONS

This application is a 35 U.S.C. § 371 National Stage application of PCT/US01/23966, filed on Aug. 1, 2001, which claims the benefit of Provisional Application Nos. 60/222,185, filed Aug. 1, 2000, 60/268,575, filed Feb. 15, 2001, and 60/281,004, filed Apr. 4, 2001.

BACKGROUND OF THE INVENTION

1. Field of the Invention

The present invention in the fields of molecular biology, immunology and medicine relates to a chimeric nucleic acid, including DNA and viral RNA encoding a fusion protein and its use as a vaccine to enhance immune responses, primarily cytotoxic T lymphocyte (CTL) responses to specific antigens such as tumor or viral antigens. The fusion protein comprises an antigenic polypeptide fused to a protein that promotes intercellular transport and processing via the MHC class I pathway, such as the VP22 protein from herpes simples virus and related herpes viruses.

2. Description of the Background Art

Naked DNA vaccines have emerged as attractive approaches for vaccine development (for review, see (1-3)). Intradermal administration of DNA vaccines via gene gun represents a convenient way of delivering DNA vaccines into professional antigen presenting cells (APCs) in vivo. Professional APCs are a superior candidate for mediating presentation of an antigen encoded by such a DNA vaccine to T lymphocytes of the immune system. The "gene gun" strategy provides efficient delivery of DNA into epidermal bone marrow-derived APCs termed Langerhans cells, which move to draining lymph nodes where they enter the lymphatic system (Condon et al., 1996). The present inventors and their colleagues have successfully used this system of DNA delivery to test various intracellular targeting strategies (Chen et al., 2000; Ji et al., 1999); co-pending, commonly assigned U.S. patent applications U.S. Ser. Nos. 09/421,608; 09/501,097, 09/693,450 and 60/281,003).

However, one limitation of DNA vaccines is their potency, since they do not have the intrinsic ability to amplify and spread in vivo as some replicating viral vaccine vectors do. The present inventors conceived a strategy that facilitates the spread of antigen may significantly enhance the potency of naked DNA vaccines.

VP22, a herpes simplex virus (HSV-1) protein has demonstrated the remarkable property of intercellular transport and is capable of distributing protein to many surrounding cells (4) (U.S. Pat. No. 6,017,735, O'Hare & Elliott, 25 Jan. 2000). For example, VP22 has been linked to p53 (Phelan, A. et al., 1998, *Nat Biotechnol* 16:440-3) or thymidine kinase (Dilber, M S et al., 1999, *Gene Ther* 6:12-21), facilitating the spread of linked proteins to surrounding cells in vitro and the treatment of model tumors.

Marek's disease virus type 1 (MDV-1) UL49 shares homology with HSV-1 VP22 (Koptidesova et al., 1995, Arch Virol. 140, 355-362) and has been shown to be capable of intercellular transport after exogenous application (Dorange et al., 2000, J Gen Virol. 81 Pt 9, 2219-2230).

Recently, self-replicating RNA vaccines (RNA replicons) have also emerged as an important strategy to enhance the potency of nucleic acid vaccines for cancer immunotherapy (for review, see Leitner, W et al., 1999, Vaccine 18:765-777. RNA replicon vaccines may be derived from alphavirus vectors, such as Sindbis virus (Hariharan, J M et al., 1998, J. Virol. 72:950-958), Semliki Forest virus (Berglund, P et al., 1997, AIDS Res. Hum. Retrovir. 13:1487-1495; Berglund, P. et al., 1998, Nat. Biotech. 16:562-565) or Venezuelan equine encephalitis virus (Pushko, P et al., 1997, Virology 239:389-401) vectors. These vaccines are self-replicating and self-limiting and may be administered as either RNA or DNA, which is then transcribed into RNA replicons in transfected cells or in vivo (Berglund et al., supra; Leitner, W W et al., 2000, Cancer Res. 60:51-55). Self-replicating RNA eventually causes lysis of transfected cells (Ying, H et al., 1999, Nat. Med. 5:823-827). These vectors do not raise the concern about integration into the host genome associated with naked DNA vectors. This is particularly important for development of vaccines that target potentially oncogenic proteins such as the human papillomavirus (HPV) E6 and E7 proteins.

One limitation on the potency of RNA replicon vaccines is their inability to spread in vivo. The present inventors conceived a strategy that facilitates the spread of antigen to enhance significantly the potency of RNA replicon vaccines.

SUMMARY OF THE INVENTION

The potency of naked DNA vaccines is limited by their inability to amplify and spread in vivo. VP22, a herpes simplex virus type 1 (HSV-1) protein and its "homologues" in other herpes viruses, such as the avian Marek's Disease Virus (MDV) have the property of intercellular transport that provide an approach for enhancing vaccine potency. The present inventors created novel fusions of VP22 with a model antigen, human papillomavirus type 16 (HPV-16) E7, in a DNA vaccine which generated enhanced spreading and MHC class I presentation of antigen. These properties led to a dramatic increase in the number of E7-specific $CD8^+$ T cell precursors in vaccinated mice (at least 50-fold) and converted a less effective DNA vaccine into one with significant potency against E7-expressing tumors. In comparison, a non-spreading mutant, VP22(1-267), failed to enhance vaccine potency. Results presented in the Examples show that the potency of DNA vaccines is dramatically improved through enhanced intercellular spreading and MHC class I presentation of the antigen.

A similar study linking MDV-1 UL49 to E7 also led to a dramatic increase in the number of E7-specific $CD8^+$ T cell precursors and potency response against E7-expressing tumors in vaccinated mice. Mice vaccinated with a MDV-1 UL49 DNA vaccine stimulated E7-specific $CD8^+$ T cell precursor at a level comparable to that induced by HSV-1 VP22/E7. Thus, fusion of MDV-1UL49 DNA to DNA encoding a target antigen gene significantly enhances the DNA vaccine potency.

The present invention is also directed to RNA replicon vaccine vaccines, preferably one based on a Sindbis virus RNA replicon. The present inventors tested E7 in the context of such a vaccine and showed (see Examples) that a Sindbis virus RNA vaccine encoding HSV-1 VP22 linked to E7 significantly increased activation of E7-specific CD8 T cells, resulting in potent antitumor immunity against E7-expressing tumors.

The present invention includes nucleic acid vaccines (DNA or RNA replicon) for any protein or peptide antigen wherein the potency of the vaccine is increased by the fusion to the nucleic acid encoding the antigen, a second nucleic acid that encodes a spreading protein, more preferably a viral spreading protein, most preferably HSV-1 VP22 or a homologue thereof.

The present invention provides a nucleic acid molecule encoding a fusion polypeptide useful as a vaccine composition, which molecule comprises:
(a) a first nucleic acid sequence encoding a first polypeptide that comprises at least one intercellular transport polypeptide;
(b) optionally, fused in frame with the first nucleic acid sequence, a linker nucleic acid sequence encoding a linker peptide; and
(c) a second nucleic acid sequence that is linked in frame to the first nucleic acid sequence or to the linker nucleic acid sequence and that encodes an antigenic polypeptide or peptide.

Also provide is a nucleic acid molecule encoding a fusion polypeptide which polypeptide comprises:
(a) a first polypeptide comprising at least one intercellular transport polypeptide;
(b) a second polypeptide comprising at least one antigenic polypeptide or peptide; and
(c) optionally, a linker peptide linking the first and the second polypeptide.

The antigenic polypeptide above preferably comprises an epitope that binds to, and is presented on the cell surface by, an MHC class I protein and is preferably between about 8 and about 11 amino acid residues in length.

A preferred transport polypeptide is a herpesvirus VP22 polypeptide or a homologue thereof, such as from herpes simplex virus, e.g., HSV-1, or Marek's disease virus.

The nucleic acid molecule preferably encodes the transport polypeptide comprising SEQ ID NO:26 or SEQ ID NO:28.

Also included is an isolated nucleic acid molecule that hybridizes with any of the above nucleic acid molecules stringent hybridization conditions.

The antigen in the above construct is preferably one which is present on, or cross-reactive with an epitope of, a pathogenic organism, cell, or virus, e.g., human papilloma virus, preferably HPV-16 protein E7 or an antigenic fragment thereof.

In another embodiment the antigen is a tumor-specific or tumor-associated antigen such as a peptide of the HER-2/neu protein.

The above nucleic acid molecule may be operatively linked to a promoter such as one which is expressed in an antigen presenting cell (APC), e.g., a dendritic cell (DC).

The invention includes an expression vector comprising the above nucleic acid molecule operatively linked to (a) a promoter; and (b) optionally, additional regulatory sequences that regulate expression of the nucleic acid in a eukaryotic cell. Preferred vectors are plasmids and self-replicating RNA replicons such as a Sindbis virus self-replicating RNA replicon, e.g., SINrep5.

Also provided is a cell which has been modified to comprise the above nucleic acid or expression vector. Preferably, the cell expresses the nucleic acid molecule. Preferred cells are APCs, including a DCs, keratinocytes, macrophages, monocytes, B lymphocytes, microglial cells, astrocytes, or activated endothelial cells.

In another embodiment, the invention is directed to a particle comprising the nucleic acid or expression vector above. The particle preferably comprises a material is suitable for introduction into a cell or an animal by particle bombardment, e.g., gold.

The invention is also directed to a fusion polypeptide, such as one encoded by the above nucleic acid molecule. The fusion polypeptide preferably comprises
(a) a first domain comprising an intercellular transport polypeptide and
(b) a second domain comprising an antigenic peptide or polypeptide.

The antigenic peptide or polypeptide preferably comprises an epitope that binds to, and is presented on the cell surface by, MHC class I proteins. The intercellular transport polypeptide and the antigenic may be linked by a chemical linker. The order of the two above polypeptides of the fusion polypeptide may be in either order (N-to C-terminal).

The fusion polypeptide's transport polypeptide is preferably a herpesvirus VP22 polypeptide or a homologue thereof as indicated above.

Also provided is a pharmaceutical composition capable of inducing or enhancing an antigen-specific immune response, comprising (a) pharmaceutically and immunologically acceptable excipient in combination with (b) a composition selected from
(i) any of the above nucleic acid molecules or expression vectors;
(ii) any of the above cells or particles;
(iii) any of the above fusion polypeptides; and
(iv) any combination of (i)-(iii.

Another embodiment is a method of inducing or enhancing an antigen specific immune response in a subject comprising administering to the subject an effective amount of the above pharmaceutical composition, thereby inducing or enhancing the response. The response is preferably one that is mediated at least in part by $CD8^+$ cytotoxic T lymphocytes (CTL), or alternatively or simultaneously, by antibodies.

A method of inducing or enhancing an antigen specific immune response in cells or in a subject comprises administering to the cells or to the subject an effective amount of the pharmaceutical composition above, thereby inducing or enhancing the response. Administration may be ex vivo to cells which are thereafter administered to the subject, preferably one histocompatible with the cells, after an optional period of culture where they may be further stimulated or expanded. The cells are preferably APCs, e.g., DC's, preferably human APCs or DCs.

Administration of the above compositions may be by intramuscular, intradermal, or subcutaneous route, or by intratumoral or peritumoral injection or instillation. The particles may be administered by biolistic injection.

A method of increasing the numbers or lytic activity of $CD8^+$ CTLs specific for a selected antigen in a subject, comprises administering to the subject an effective amount of a any of the above compositions wherein.
(1) the nucleic acid molecule, the expression vector, the cell, the particle or the fusion polypeptide comprises the antigen,
(2) the antigen comprises an epitope that binds to, and is presented on the cell surface by, MHC class I proteins, thereby increasing the numbers or activity of the CTLs.

A method of inhibiting growth or preventing re-growth of a tumor in a subject, comprises administering to the subject an effective amount of any of the above a compositions, wherein
(1) the nucleic acid molecule, the expression vector, the cell, the particle or the fusion polypeptide comprises the antigen, (2) the antigen comprises one or more tumor-associated or tumor-specific epitopes present on the tumor in the subject thereby inhibiting the growth or preventing the re-growth. In this method, administration may be intratumoral or peritumoral, and the method may further comprise treating the subject with radiotherapy or chemotherapy.

BRIEF DESCRIPTION OF THE DRAWINGS

FIGS. 1A and 1B. In vitro and in vivo expression of VP22/GFP protein. FIG. 1A: Fluorescent microscopic examination to investigate the in vitro spread of chimeric VP22/E7/GFP protein. 293 $D^bK^b$ cells were transfected with E7/GFP, VP22(1-267)/E7/GFP, or VP22/E7/GFP DNA. Note: Significant spread of GFP was observed in cells transfected with VP22/E7/GFP DNA but not in cells transfected with E7/GFP or VP22(1-267)/E7/GFP DNA. FIG. 1B: Immunohistochemical staining to demonstrate the in vivo spread of chimeric VP22/GFP protein. Mice were vaccinated with 2 μg/mouse of pcDNA3-GFP (upper panel) or pcDNA3-VP22/GFP DNA (lower panel). Skin from vaccinated mice was stained with rabbit anti-GFP polyclonal antibody. Note: Positive cells are stained brown. Significant spread of GFP was noted in skin obtained from mice vaccinated with pcDNA3-VP22/GFP (lower panel).

FIG. 4. CTL assays using transfected or vaccinia-infected 293 $D^bK^b$ cells and an E7-specific T cell line. (A) 293 $D^bK^b$ cells transfected with various DNA constructs served as target cells. (B) 293 $D^bK^b$ cells infected with various vaccinia constructs served as target cells. Both CTL assays were performed with various E:T ratios using $D^b$-restricted E7-specific CD8$^+$ T cells as effector cells.

FIG. 7 shows the nucleotide sequence of pcDNA3-VP22/E7 DNA (SEQ ID NO:22) which is 1254 nucleotides (+stop codon). The corresponding amino acid sequence (SEQ ID NO:23) has 418 residues. SEQ ID NO:22 includes nucleotides 1-903 (upper case) encoding VP22 (SEQ ID NO:24). The VP22 amino acid sequence (1-301) is SEQ ID NO:26. Nucleotides 904-921 and the corresponding amino acids 302-307 are a "linker" sequence. Nucleotides 922-1209 (SEQ ID NO:25) (lower case) encode 96 of the 98 amino acids of wild-type E7 protein. The E7 amino sequence of 96 residues, from residues 308-403 is SEQ ID NO:27; the two C-terminal residues missing from the E7 polypeptide of this construct are Lys-Pro (which are intended as part of the present invention). Also shown in a stretch of vector sequence (underscored) from nucleotides 1210-1257 (including the stop codon).

FIG. 8A is schematic representation of the MDV-1 and HSV-1 genome and the corresponding genetic locus of UL49. Rulers indicate the size of the complete genome of MDV-1 and HSV-1 in kbp. The gene product of UL49 from MDV-1 (SEQ ID NO:29) is 249 residues whereas the HSV-1 protein [SEQ ID NO:24] is 301 residues in length. UL and US refer to long and short unique regions. Terminal and internal UL repeats are indicated as TRL and IRL. Terminal and internal US repeats are indicated as TRS and IRS. FIG. 8B shows an amino acid alignment of the VP22 of MDV-1 and HSV-1. Boxed regions represent matched amino acids. Italicized amino acids indicate insertions. Horizontal lines represent gaps. Note: MVP22 and HVP22 amino acid sequences were optimally aligned using DNASTAR software with the Clustal method and PAM250 residue weight table. The results revealed only 20.1% sequence identity.

FIG. 9A shows a flow cytometric analysis of IFN-γ-secreting E7-specific CD8$^+$ T cell precursors. Vaccination of mice with MVP22/E7 DNA generated the greatest number of IFN-γ$^+$ CD8$^+$ T cell precursors compared to vaccination with the other constructs. The results of one representative experiment are shown out of three that were performed. FIG. 9B shows a flow cytometric analysis of IFN-γ-secreting E7-specific $CD4^+$ T cell precursors. No significant difference in the number of E7-specific IFN-γ-secreting $CD4^+$ cell precursors was observed in mice immunized with the various DNA vaccines.

FIG. 10 shows the results of an ELISA measuring anti-E7-antibodies in the sera of vaccinated mice. No significant difference were observed between mice immunized with the various DNA vaccines.

FIG. 11A shows in vivo tumor protection in mice immunized and challenged subcutaneously (s.c.) with TC-1 tumor cells. The results are from one representative experiment of two performed. FIG. 2B shows survival of mice vaccinated with various DNA vaccines and challenged with 8 tumor. A comparison of post-treatment survival revealed that only mice vaccinated with MVP22/E7 DNA showed 100% survival.

FIG. 12A shows the mean number of pulmonary metastatic nodules in lungs of mice in each vaccinated group. Five mice per group were challenged intravenously (i.v.). MVP22/E7 DNA-vaccinated mice exhibited the lowest number pulmonary metastases. FIG. 12B shows mean lung masses for each group. MVP22/E7 DNA-vaccinated mice had the lowest mean lung mass.

FIG. 16A shows E7-specific T cell cytotoxic activity. Mice were immunized with various SINrep5 self-replicating RNA vaccines via intramuscular (i.m.) injection. Splenocytes were collected after 14 days. Vaccination with VP22/E7 RNA induced significantly higher lytic activity than did the other RNA vaccines (P<0.001, one-way ANOVA). FIG. 16B shows IFNγ secreted by E7-specific $CD8^+$ T cell precursors measured by ELISA. Splenocytes obtained from mice vaccinated with self-replicating VP22/E7 secreted the highest amounts of IFNγ compared to those from mice vaccinated with the other RNA vaccines (P<0.001, one-way ANOVA).

FIG. 16C shows flow cytometric analysis of IFNγ-secreting E7-specific CD8+ cells in mice vaccinated with various recombinant RNA vaccines. Splenocytes cultured with E7 peptide (aa 49-57) for 6 days were stained for both CD8 and intracellular IFNγ. The number of IFNγ-secreting $CD8^+$ T cells, indicated in the upper right-hand corner of each panel, was determined using flow cytometry. The VP22/E7-vaccinated group generated a higher number of E7-specific IFNγ-secreting CD8+ cells than did groups vaccinated with other recombinant RNA vaccines.

FIG. 21A shows tissue from mice immunized with normal saline i.m. (magnification, 3160). FIG. 21B shows tissue from mice immunized with self-replicating SINrep5 RNA i.m. (magnification, 3100) and sacrificed 4 days after immunization. Note that injection with SINrep5 RNA induced a higher number of apoptotic cells in the muscle tissues than did injection with normal saline.

Figure 2:
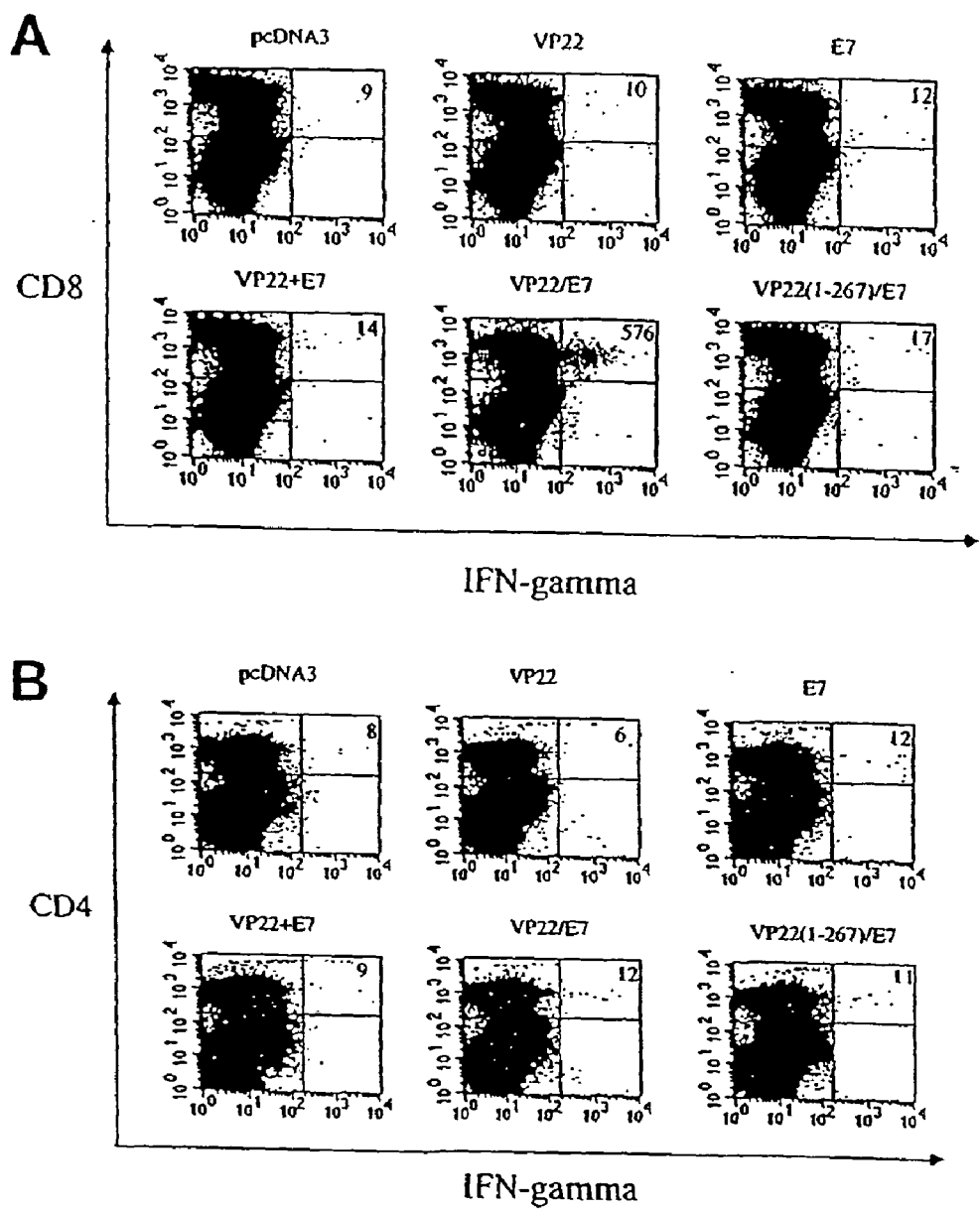
FIG. 2. Flow cytometry analysis of IFN-γ-secreting E7-specific $CD8^+$ and $CD4^+$ T cell precursors in mice vaccinated with various recombinant DNA vaccines. Mice were vaccinated via gene gun with 2 μg of E7, VP22, VP22 mixed with E7 (VP22+E7), VP22(1-267)/E7, VP22/E7 DNA, or pcDNA3 (no insert). One week later, mice were boosted with the same regimen as the first vaccination. (A) Determination of E7-specific $CD8^+$ T cells. Splenocytes from vaccinated mice were cultured in vitro with 1 μg/ml of E7 peptide (aa 49-57) overnight and analyzed for both CD8 and intracellular IFN-γ using flow cytometry analysis. Note: Vaccination of mice with VP22/E7 DNA generated the highest frequency of IFN-γ$^+$ CD8$^+$ double positive T cells compared to the other groups. The data from intracellular cytokine staining shown here are from one representative experiment of two performed. (B) Determination of E7-specific $CD4^+$ T cells. The number of IFN-γ-secreting $CD4^+$ T cells was analyzed using flow cytometry. Note: No significant difference in the frequency of E7-specific IFN-γ-secreting $CD4^+$ cells was observed in mice immunized with various recombinant DNA vaccines.

DESCRIPTION OF THE PREFERRED EMBODIMENTS (Certain documents listed at the end of the Examples, are cited below either by number in parentheses or by author name and year, without reference citation. These all appear in the list at the end, either prefaced by a number or just author name. Some of these references are duplicative)

The present inventors have now identified new proteins and nucleic acids that serve as the basis for improved immunotherapeutic (vaccine) compositions and methods. Chimeric or fusion polypeptides, and nucleic acids coding therefor, include a first polypeptide (or domain) that encodes an intercellular spreading protein fused, either directly or via a linker, to a second polypeptide or peptide that comprises an antigen which can be a single epitope or multiple epitopes. The multiple epitopes may be arranged in their native molecular conformation, or may be an engineered combination of the same or different epitopes occurring in single or multiple copies.

Specifically, the present inventors investigated the novel use of VP22 proteins linked to a model antigen (HPV-16 E7) in the context of a DNA or RNA replicon vaccine and found that it led to the spread of linked antigen to surrounding cells and enhanced antigen-specific immune responses and anti-tumor effects. As disclosed herein, linkage of two types of VP22 to E7 led to a dramatic increase in the number of E7-specific CD8$^+$ T cell precursors in vaccinated mice (at least 50-fold) and converted a less effective DNA vaccine into one with significant potency against E7-expressing tumors. Experiments using a non-spreading VP22(1-267) mutant failed to enhance vaccine potency, indicating that the property of intercellular spreading generated by VP22 was important for enhancing vaccine potency. These results indicated that the strategy of linking an intercellular spreading protein such as VP22 to any antigen can dramatically improve the potency of naked DNA or RNA replicon vaccines.

The spreading protein is preferably a viral spreading protein, most preferably a herpesvirus VP22 protein. Exemplified herein are fusion constructs that comprise herpes simplex virus-1 (HSV-1) VP22 (abbreviated HVP22) and its homologue from Marek's disease virus (MDV) termed MDV-VP22 or MVP-22). Also included in the invention are homologues of VP22 from other members of the herpesviridae or polypeptides from nonviral sources that are considered to be homologous and share the functional characteristic of promoting intercellular spreading of a polypeptide or peptide that is fused or chemically conjugated thereto.

DNA encoding HVP22 has the sequence SEQ ID NO:24 which is shown in FIG. 7 as nucleotides 1-921 of the longer sequence SEQ ID NO:22 (which is the full length nucleotide sequence of a vector that comprises HVP22). DNA encoding MVP22 is SEQ ID NO:29 shown below:

```
atg ggg gat tct gaa agg cgg aaa tcg gaa cgg cgt cgt tcc ctt gga    48 tat ccc tct gca tat gat gac gtc tcg att cct gct cgc aga cca tca    96 aca cgt act cag cga aat tta aac cag gat gat ttg tca aaa cat gga   144 cca ttt acc gac cat cca aca caa aaa cat aaa tcg gcg aaa gcc gta   192 tcg gaa gac gtt tcg tct acc acc cgg ggt ggc ttt aca aac aaa ccc   240 cgt acc aag ccc ggg gtc aga gct gta caa agt aat aaa ttc gct ttc   288 agt acg gct cct tca tca gca tct agc act tgg aga tca aat aca gtg   336 gca ttt aat cag cgt atg ttt tgc gga gcg gtt gca act gtg gct caa   384 tat cac gca tac caa ggc gcg ctc gcc ctt tgg cgt caa gat cct ccg   432 cga aca aat gaa gaa tta gat gca ttt ctt tcc aga gct gtc att aaa   480 att acc att caa gag ggt cca aat ttg atg ggg gaa gcc gaa acc tgt   528 gcc cgc aaa cta ttg gaa gag tct gga tta tcc cag ggg aac gag aac   576 gta aag tcc aaa tct gaa cgt aca acc aaa tct gaa cgt aca aga cgc   624 ggc ggt gaa att gaa atc aaa tcg cca gat ccg gga tct cat cgt aca   672 cat aac cct cgc act ccc gca act tcg cgt cgc cat cat tca tcc gcc   720 cgc gga tat cgt agc agt gat agc gaa taa                           747
```

Figure 8:
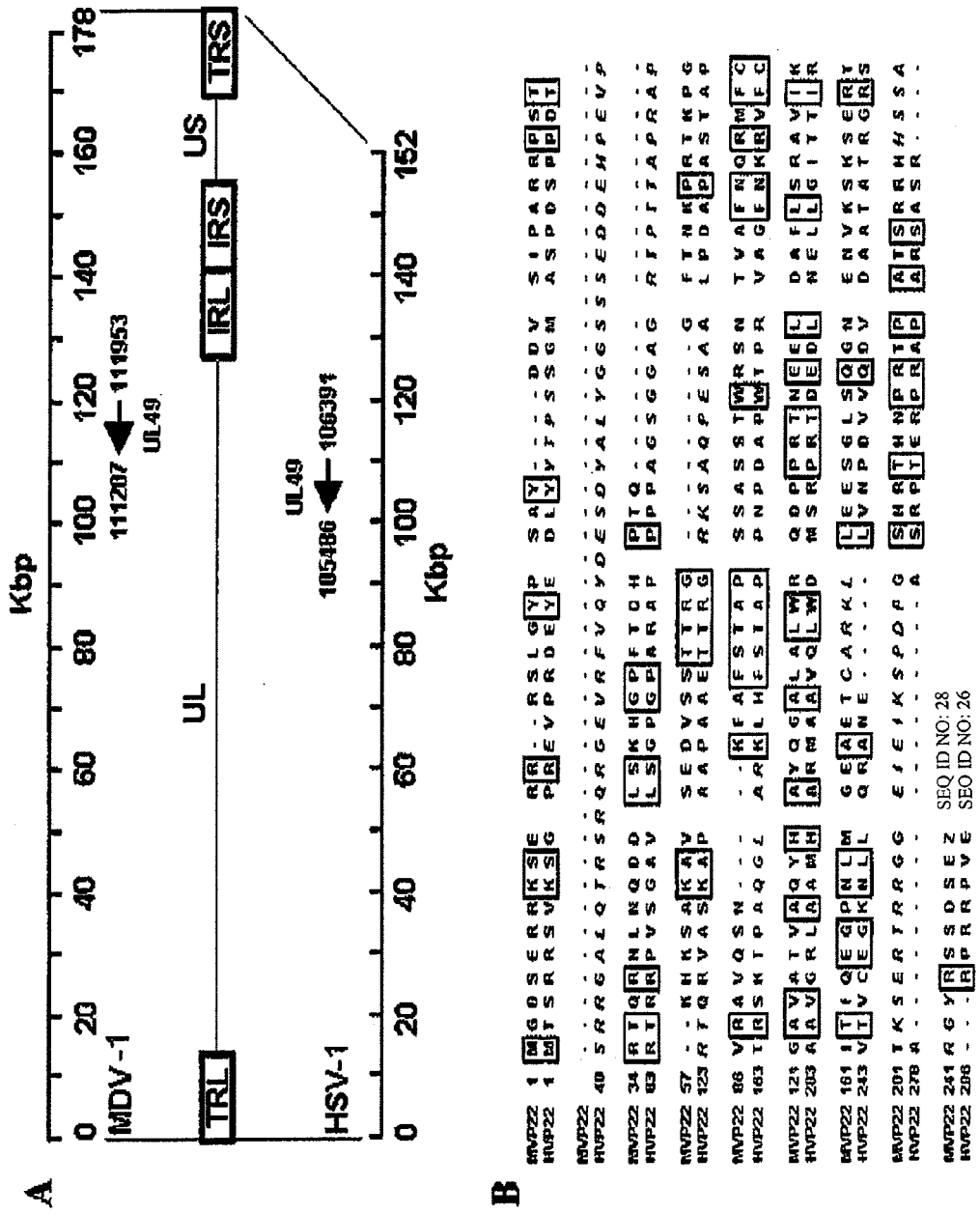
FIGS. 8A and 8B is a schematic diagram show the genetic locus and amino acid alignment of MDV-1 UL49 (VP22) [SEQ ID NO:28] and HSV-1 VP22 [SEQ ID NO:24].
Figure 9:
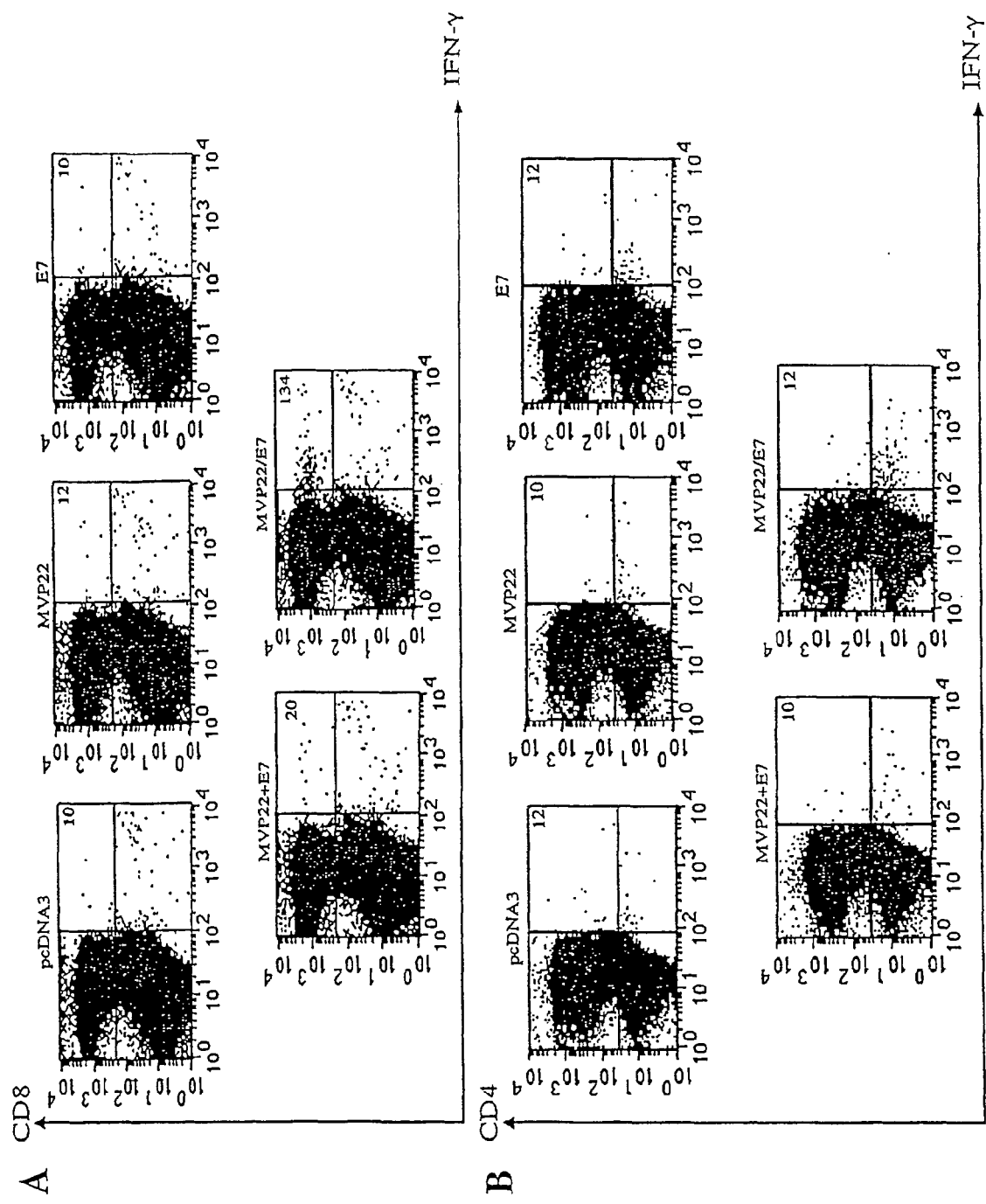
FIGS. 9A, 9B and 10 show immune reactivity induced by various recombinant DNA vaccines.

The amino acid sequence of HVP22 polypeptide is SEQ ID NO:26 which is shown in FIG. 7 as amino acid residues 1-301 of SEQ ID NO:23 (the full length amino acid encoded by the vector) and also shown aligned form in FIG. 8A.

The amino acid sequence of the MDV PV22, SEQ ID NO:28, is shown in aligned form in FIG. 8A, and is also shown below:

```
Met Gly Asp Ser Glu Arg Arg Lys Ser Glu Arg Arg Ser Leu Gly   16

Tyr Pro Ser Ala Tyr Asp Asp Val Ser Ile Pro Ala Arg Arg Pro Ser   32

Thr Arg Thr Gln Arg Asn Leu Asn Gln Asp Asp Leu Ser Lys His Gly   48

Pro Phe Thr Asp His Pro Thr Gln Lys His Lys Ser Ala Lys Ala Val   64

Ser Glu Asp Val Ser Ser Thr Thr Arg Gly Gly Phe Thr Asn Lys Pro   80

Arg Thr Lys Pro Gly Val Arg Ala Val Gln Ser Asn Lys Phe Ala Phe   96

Ser Thr Ala Pro Ser Ser Ala Ser Ser Thr Trp Arg Ser Asn Thr Val  112

Ala Phe Asn Gln Arg Met Phe Cys Gly Ala Val Ala Thr Val Ala Gln  128

Tyr His Ala Tyr Gln Gly Ala Leu Ala Leu Trp Arg Gln Asp Pro Pro  144

Arg Thr Asn Glu Glu Leu Asp Ala Phe Leu Ser Arg Ala Val Ile Lys  160

Ile Thr Ile Gln Glu Gly Pro Asn Leu Met Gly Glu Ala Glu Thr Cys  176

Ala Arg Lys Leu Leu Glu Glu Ser Gly Leu Ser Gln Gly Asn Glu Asn  192

Val Lys Ser Lys Ser Glu Arg Thr Thr Lys Ser Glu Arg Thr Arg Arg  208

Gly Gly Glu Ile Glu Ile Lys Ser Pro Asp Pro Gly Ser His Arg Thr  224

His Asn Pro Arg Thr Pro Ala Thr Ser Arg Arg His His Ser Ser Ala  240

Arg Gly Tyr Arg Ser Ser Asp Ser Glu —                            249
```

A DNA clone pcDNA3 VP22/E7, that includes the coding sequence for HVP22 and the HPV-16 protein, E7 (plus some additional vector sequence) is SEQ ID NO:22.

The amino acid sequence of E7 (SEQ ID NO:27) is residues 308-403 of SEQ ID NO:23. This particular clone has only 96 of the 98 residues present in E7. The C-terminal residues of wild-type E7, Lys and Pro, are absent from this construct. This is an example of a deletion variant as the term is described below. Such deletion variants (e.g., terminal truncation of two or a small number of amino acids) of other antigenic polypeptides are examples of the embodiments intended within the scope of the fusion polypeptides of this invention.

General Recombinant DNA Methods

Basic texts disclosing general methods of molecular biology, all of which are incorporated by reference, include: Sambrook, J et al., *Molecular Cloning: A Laboratory Manual*, 2$^{nd}$ Edition, Cold Spring Harbor Press, Cold Spring Harbor, N.Y., 1989; Ausubel, F M et al. *Current Protocols in Molecular Biology*, Vol. 2, Wiley-Interscience, New York, (current edition); Kriegler, *Gene Transfer and Expression: A Laboratory Manual* (1990); Glover, D M, ed, *DNA Cloning: A Practical Approach*, vol. I & II, IRL Press, 1985; Albers, B. et al., *Molecular Biology of the Cell*, 2$^{nd}$ Ed., Garland Publishing, Inc., New York, N.Y. (1989); Watson, J D et al., *Recombinant DNA*, 2$^{nd}$ Ed., Scientific American Books, New York, 1992; and Old, R W et al., *Principles of Gene Manipulation: An Introduction to Genetic Engineering*, 2$^{nd}$ Ed., University of California Press, Berkeley, Calif. (1981).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, cDNA molecules encoding the amino acid sequence corresponding to the fusion polypeptide of the present invention or fragments or derivatives thereof can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

This invention includes isolated nucleic acids having a nucleotide sequence encoding the novel fusion polypeptides that comprise a spreading protein and an antigen, fragments thereof or equivalents thereof. The term nucleic acid as used herein is intended to include such fragments or equivalents. The nucleic acid sequences of this invention can be DNA or RNA.

A cDNA nucleotide sequence the fusion polypeptide can be obtained by isolating total mRNA from an appropriate cell line. Double stranded cDNA is prepared from total mRNA. cDNA can be inserted into a suitable plasmid, bacteriophage or viral vector using any one of a number of known techniques.

In reference to a nucleotide sequence, the term "equivalent" is intended to include sequences encoding structurally homologous and/or a functionally equivalent proteins. For example, a natural polymorphism of the viral VP22 spreading protein nucleotide sequence (especially at the third base of a codon) may be manifest as "silent" mutations which do not change the amino acid sequence. Furthermore, there may be one or more naturally occurring isoforms or related, immunologically cross-reactive family members of the VP22 proteins described herein. Such isoforms or family members are defined as proteins that share function amino acid sequence similarity to HVP22.

Fragment of Nucleic Acid

A fragment of the nucleic acid sequence is defined as a nucleotide sequence having fewer nucleotides than the nucleotide sequence encoding the full length VP22 protein, antigenic polypeptide or the fusion thereof. This invention includes such nucleic acid fragments that encode polypeptides which retain (1) the ability of the fusion polypeptide to induce increases in frequency or reactivity of T cells, preferably CD8+ T cells, that are specific for the antigen portion of the fusion polypeptide.

For example, a nucleic acid fragment as intended herein encodes a VP22 polypeptide that retains the ability to improve the immunogenicity of an antigen when administered as a fusion polypeptide with an antigenic polypeptide or peptide.

Generally, the nucleic acid sequence encoding a fragment of a VP22 polypeptide comprises of nucleotides from the sequence encoding the mature protein.

Nucleic acid sequences of this invention may also include linker sequences, natural or modified restriction endonuclease sites and other sequences that are useful for manipulations related to cloning, expression or purification of encoded protein or fragments. These and other modifications of nucleic acid sequences are described herein or are well-known in the art.

The techniques for assembling and expressing DNA coding sequences for spreading proteins such as VP22 and antigenic polypeptides such as synthesis of oligonucleotides, PCR, transforming cells, constructing vectors, expression systems, and the like are well-established in the art. Those of ordinary skill are familiar with the standard resource materials for specific conditions and procedures.

Expression Vectors and Host Cells

This invention includes an expression vector comprising a nucleic acid sequence encoding a spreading protein/antigen fusion polypeptide operably linked to at least one regulatory sequence. "Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Those skilled in the art appreciate that the particular design of an expression vector of this invention depends on considerations such as the host cell to be transfected and/or the type of protein to be expressed.

The present expression vectors comprise the full range of nucleic acid molecules encoding the various embodiments of the fusion polypeptide and its functional derivatives (defined herein) including polypeptide fragments, variants, etc.

Such expression vectors are used to transfect host cells for expression of the DNA and production of the encoded proteins which include fusion proteins or peptides. It will be understood that a genetically modified cell expressing the fusion polypeptide may transiently express the exogenous DNA for a time sufficient for the cell to be useful for its stated purpose.

The present in invention provides methods for producing the fusion polypeptides, fragments and derivatives. For example, a host cell transfected with a nucleic acid vector that encodes the fusion polypeptide is cultured under appropriate conditions to allow expression of the polypeptide.

Host cells may also be transfected with one or more expression vectors that singly or in combination comprise DNA encoding at least a portion of the fusion polypeptide and DNA encoding at least a portion of a second protein, so that the host cells produce yet further fusion polypeptides that include both the portions.

A culture typically includes host cells, appropriate growth media and other byproducts. Suitable culture media are well known in the art. The fusion polypeptide can be isolated from medium or cell lysates using conventional techniques for purifying proteins and peptides, including ammonium sulfate precipitation, fractionation column chromatography (e.g. ion exchange, gel filtration, affinity chromatography, etc.) and/or electrophoresis (see generally, "Enzyme Purification and Related Techniques", *Methods in Enzymology*, 22: 233-577 (1971)). Once purified, partially or to homogeneity, the recombinant polypeptides of the invention can be utilized in pharmaceutical compositions as described in more detail herein.

Prokaryotic or eukaryotic host cells transformed or transfected to express the fusion polypeptide or a homologue or functional derivative thereof are within the scope of the invention. For example, the fusion polypeptide may be expressed in bacterial cells such as *E. coli*, insect cells (baculovirus), yeast, or mammalian cells such as Chinese hamster ovary cells (CHO) or human cells. Other suitable host cells maybe found in Goeddel, (1990) supra or are otherwise known to those skilled in the art.

Expression in eukaryotic cells leads to partial or complete glycosylation and/or formation of relevant inter- or intra-chain disulfide bonds of the recombinant protein.

Although preferred vectors are described in the Examples, other examples of expression vectors are provided here. Examples of vectors for expression in yeast *S. cerevisiae* include pYepSec1 (Baldari et al., (1987) *EMBO J.* 6:229-234), pMFa (Kurjan et al. (1982) *Cell* 30:933-943), pJRY88 (Schultz et al., (1987) *Gene* 54:113-123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3: 2156-2165,) and the pVL series (Lucklow, V. A., and Summers, M. D., (1989) *Virology* 170: 31-39). Generally, COS cells (Gluzman, Y., (1981) *Cell* 23: 175-182) are used in conjunction with such vectors as pCDM 8 (Aruffo A. and Seed, B., supra, for transient amplification/expression in mammalian cells, while CHO (dhfr-negative CHO) cells are used with vectors such as pMT2PC (Kaufman et al. (1987), *EMBO J.* 6: 187-195) for stable amplification/expression in mammalian cells. The NS0 myeloma cell line (a glutamine synthetase expression system.) is available from Celltech Ltd.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69: 301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21 (DE3) or HMS174(DE3) from a resident λ prophage harboring a T7gn1 under the transcriptional control of the lacUV 5 promoter.

One embodiment of this invention is a transfected cell which expresses novel fusion polypeptide.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; and Jay, E., *J Biol Chem* (1984) 259:6311.

Synthetic oligonucleotides are prepared by either the phosphotriester method as described by references cited above or the phosphoramidite method as described by Beaucage, S. L., and Caruthers, M. H., *Tet Lett* (1981) 22:1859; and Matteucci, M. D., and Caruthers, M. H., *J Am Chem Soc* (1981) 103:3185 and can be prepared using commercially available automated oligonucleotide synthesizers. Kinase treatment of single strands prior to annealing or for labeling is achieved using an excess, e.g., about 10 units of polynucleotide kinase to 1 mmole substrate in the presence of 50 mM Tris, pH 7.6, 10 mM $MgCl_2$, 5 mM dithiothreitol, 1-2 mM ATP, 1.7 pmoles $\gamma$-$^{32}$P-ATP (2.9 mCi/mmole), 0.1 mM spermidine, 0.1 mM EDTA.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are typically performed in 15-50 ml volumes under the following standard conditions and temperatures: for example, 20 mM Tris-HCl pH 7.5, 10 mM $MgCl_2$, 10 mM DTT, 33 µg/ml BSA, 10-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 nM total end concentration). Intermolecular blunt end ligations are performed at 1 mM total ends concentration.

In vector construction employing "vector fragments", the fragment is commonly treated with bacterial alkaline phosphatase (BAP) or calf intestinal alkaline phosphatase (CIAP) in order to remove the 5' phosphate and prevent self-ligation. Digestions are conducted at pH 8 in approximately 10 mM Tris-HCl, 1 mM EDTA using BAP or CIAP at about 1 unit/mg vector at 60° for about one hour. The preparation is extracted with phenol/chloroform and ethanol precipitated. Alternatively, re-ligation can be prevented in vectors which have been double digested by additional restriction enzyme and separation of the unwanted fragments.

Any of a number of methods are used to introduce mutations into the coding sequence to generate the variants of the invention. These mutations include simple deletions or insertions, systematic deletions, insertions or substitutions of clusters of bases or substitutions of single bases.

For example, modifications of the spreading protein or the antigenic polypeptide DNA sequence are created by site-directed mutagenesis, a well-known technique for which protocols and reagents are commercially available (Zoller, M J et al., *Nucleic Acids Res* (1982) 10:6487-6500 and Adelman, J P et al, *DNA* (1983) 2:183-193)). Correct ligations for plasmid construction are confirmed, for example, by first transforming *E. coli* strain MC1061 (Casadaban, M., et al., *J Mol Biol* (1980) 138:179-207) or other suitable host with the ligation mixture. Using conventional methods, transformants are selected based on the presence of the ampicillin-, tetracycline- or other antibiotic resistance gene (or other selectable marker) depending on the mode of plasmid construction. Plasmids are then prepared from the transformants with optional chloramphenicol amplification optionally following chloramphenicol amplification ((Clewell, D B et al., *Proc Natl Acad Sci USA* (1969) 62:1159; Clewell, D. B., *J Bacteriol* (1972) 110:667). Several mini DNA preps are commonly used. See, e.g., Holmes, D S, et al., *Anal Biochem* (1981) 114:193-197; Birnboim, H C et al., *Nucleic Acids Res* (1979) 7:1513-1523. The isolated DNA is analyzed by restriction and/or sequenced by the dideoxy nucleotide method of Sanger (*Proc Natl Acad Sci USA* (1977) 74:5463) as further described by Messing, et al., *Nucleic Acids Res* (1981) 9:309, or by the method of Maxam et al. *Methods in Enzymology* (1980) 65:499.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69: 301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21(DE3) or HMS174(DE3) from a resident λ prophage harboring a T7gn1 under the transcriptional control of the lacUV 5 promoter.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The preferred promoter sequences of the present invention must be operable in mammalian cells and may be either eukaryotic or viral promoters. Although preferred promoters are described in the Examples, other useful promoters and regulatory elements are discussed below. Suitable promoters may be inducible, repressible or constitutive. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., *Cell* 41:521 (1985)) or in the RSV-LTR (from Rous sarcoma virus) (Gorman, C. M., *Proc. Natl. Acad. Sci. USA* 79:6777 (1982). Also useful are the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982); the SV40 early promoter (Benoist, C., et al., *Nature* 290:304-310 (1981)); and the yeast gal4 gene promoter (Johnston, S. A., et al., *Proc. Natl. Acad. Sci. (USA)* 79:6971-6975 (1982); Silver, P. A., et al., *Proc. Natl. Acad. Sci. (USA)* 81:5951-5955 (1984)). Other illustrative descriptions of transcriptional factor association with promoter regions and the separate activation and DNA binding of transcription factors include: Keegan et al., *Nature* (1986) 231:699; Fields et al., *Nature* (1989) 340:245; Jones, *Cell* (1990) 61:9; Lewin, *Cell* (1990) 61:1161; Ptashne et al., *Nature* (1990) 346:329; Adams et al., *Cell* (1993) 72:306. The relevant disclosure of all of these above-listed references is hereby incorporated by reference.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B. M., *Genes IV*, Oxford University Press, Oxford, (1990), pp. 552-576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

The nucleic acid sequences of the invention can also be chemically synthesized using standard techniques. Various methods of chemically synthesizing polydeoxynucleotides are known, including solid-phase synthesis which, like peptide synthesis, has been fully automated with commercially available DNA synthesizers (See, e.g., Itakura et al. U.S. Pat.

No. 4,598,049; Caruthers et al. U.S. Pat. No. 4,458,066; and Itakura U.S. Pat. Nos. 4,401,796 and 4,373,071, incorporated by reference herein).

Proteins and Polypeptides

The present invention includes an "isolated" fusion polypeptide comprising a spreading polypeptide and an antigenic polypeptide, such as the VP22/E7 fusion in SEQ ID NO:23. While the present disclosure exemplifies the full length VP22 protein of HSV-1 and MDV, it is to be understood that homologues of VP22 from other viruses or from non-viral origin, and mutants thereof that possess the characteristics disclosed herein are intended within the scope of this invention.

Also included is a "functional derivative" of VP22 which is an amino acid substitution variant, a "fragment," or a "chemical derivative" of VP22, which terms are defined below. A functional derivative retains measurable VP22-like activity, preferably that of promoting intercellular spreading and immunogenicity of one or more antigenic epitopes fused thereto which permits its utility in accordance with the present invention. "Functional derivatives" encompass "variants" and "fragments" regardless of whether the terms are used in the conjunctive or the alternative herein.

A functional homologue must possess the above biochemical and biological activity. In view of this functional characterization, use of homologous VP22 proteins including proteins not yet discovered, fall within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence (e.g., HPV22, SEQ ID NO:27). The amino acid residues (or nucleotides) at corresponding amino acid positions (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to HVP22 nucleic acid molecules. BLAST protein searches can be performed with the XBLAST program, score=50, wordlength=3 to obtain amino acid sequences homologous to HVP22 protein molecules. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Thus, a homologue of HVP22 described above is characterized as having (a) functional activity of native HVP22 and (b) sequence similarity to a native VP22 protein (such as SEQ ID NO:27 or SEQ ID NO:29 when determined above, of at least about 20% (at the amino acid level), preferably at least about 40%, more preferably at least about 70%, even more preferably at least about 90%.

It is within the skill in the art to obtain and express such a protein using DNA probes based on the disclosed sequences of VP22. Then, the fusion protein's biochemical and biological activity can be tested readily using art-recognized methods such as those described herein, for example, a T cell proliferation, cytokine secretion or a cytolytic assay, or an in vivo assay of tumor protection or therapy. A biological assay of the stimulation of antigen-specific T cell reactivity will indicate whether the homologue has the requisite activity to qualify as a "functional" homologue.

A "variant" of a VP22 refers to a molecule substantially identical to either the full protein or to a fragment thereof in which one or more amino acid residues have been replaced (substitution variant) or which has one or several residues deleted (deletion variant) or added (addition variant). A "fragment" of VP22 refers to any subset of the molecule, that is, a shorter polypeptide of the full-length protein.

A number of processes can be used to generate fragments, mutants and variants of the isolated DNA sequence. Small subregions or fragments of the nucleic acid encoding the spreading protein, for example 1-30 bases in length, can be prepared by standard, chemical synthesis. Antisense oligonucleotides and primers for use in the generation of larger synthetic fragment.

A preferred group of VP22 variants are those in which at least one amino acid residue and preferably, only one, has been substituted by different residue. For a detailed description of protein chemistry and structure, see Schulz, G E et al., *Principles of Protein Structure,* Springer-Verlag, New York, 1978, and Creighton, T. E., *Proteins: Structure and*

*Molecular Properties,* W. H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIGS. 3-9 of Creighton (supra). Based on such an analysis, conservative substitutions are defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the VP22 protein in terms of its intercellular spreading activity and its ability to stimulate antigen specific T cell reactivity to an antigenic epitope or epitopes that are fused to the spreading protein. However, when it is difficult to predict the exact effect of the substitution, deletion or insertion in advance of doing so, one skilled in the art will appreciate that the effect can be evaluated by routine screening assays such as those described here, without requiring undue experimentation.

Whereas shorter chain variants can be made by chemical synthesis, for the present invention, the preferred longer chain variants are typically made by site-specific mutagenesis of the nucleic acid encoding the VP22 polypeptide, expression of the variant nucleic acid in cell culture, and, optionally, purification of the polypeptide from the cell culture, for example, by immunoaffinity chromatography using specific antibody immobilized to a column (to absorb the variant by binding to at least one epitope).

Chemical Derivatives

"Chemical derivatives" of the VP22 or fusion polypeptide contain additional chemical moieties not normally a part of the protein. Covalent modifications of the polypeptide are included within the scope of this invention. Such derivatized moieties may improve the solubility, absorption, biological half life, and the like. Moieties capable of mediating such effects are disclosed, for example, in *Remington 's Pharmaceutical Sciences,* 16$^{th}$ ed., Mack Publishing Co., Easton, Pa. (1980).

Such modifications may be introduced into the molecule by reacting targeted amino acid residues of the polypeptide with an organic derivatizing agent that is capable of reacting with selected side chains or terminal residues. Another modification is cyclization of the protein. Examples of chemical derivatives of the polypeptide follow.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79-86), acetylation of the N-terminal amine, and amidation of the C-terminal carboxyl groups.

Also included are peptides wherein one or more D-amino acids are substituted for one or more L-amino acids.

Multimeric Peptides

The present invention also includes longer polypeptides in which a basic peptidic sequence obtained from the sequence of either the VP22 or the antigenic polypeptide or peptide unit is repeated from about two to about 100 times, with or without intervening spacers or linkers. It is understood that such multimers may be built from any of the peptide variants defined herein. Moreover, a peptide multimer may comprise different combinations of peptide monomers and the disclosed substitution variants thereof. Such oligomeric or multimeric peptides can be made by chemical synthesis or by recombinant DNA techniques as discussed herein. When produced chemically, the oligomers preferably have from 2-8 repeats of the basic peptide sequence. When produced recombinantly, the multimers may have as many repeats as the expression system permits, for example from two to about 100 repeats.

In tandem multimers, preferably dimers and trimers, of the fusion polypeptide, the chains bonded by interchain disulfide bonds or other "artificial" covalent bonds between the chains such th; the chains are "side-by-side" rather than "end to end."

Therapeutic Compositions and their Administration

A vaccine composition comprising the nucleic acid encoding the fusion polypeptide, or a cell expressing this nucleic acid is administered to a mammalian subject, preferably a human. The vaccine composition is administered in a pharmaceutically acceptable carrier in a biologically effective or a therapeutically effective amount. The composition may be given alone or in combination with another protein or peptide such as an immunostimulatory molecule. Treatment may include administration of an adjuvant, used in its broadest sense to include any nonspecific immune stimulating compound such as an interferon. Adjuvants contemplated herein include resorcinols, non-ionic surfactants such as polyoxyethylene oleyl ether and n-hexadecyl polyethylene ether.

A therapeutically effective amount is a dosage that, when given for an effective period of time, achieves the desired immunological or clinical effect.

A therapeutically active amount of a nucleic acid encoding the fusion polypeptide may vary according to factors such as the disease state, age, sex, and weight of the individual, and the ability of the peptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount is between about 1 nanogram and about 10 milligram per kilogram of body weight of the recipient, more preferably between about 0.1 µg and 1 µg/kg. Dosage forms suitable for internal administration preferably contain (for the latter dose range) from about 0.01 µg to 100 µg of active ingredient per unit. The active ingredient may vary from 0.5 to 95% by weight based on the total weight of the composition. Alternatively, an effective dose of cells expressing the nucleic acid is between about $10^4$ and $10^8$ cells. Those skilled in the art of immunotherapy will be able to adjust these doses without undue experimentation.

The active compound may be administered in a convenient manner, e.g., injection by a convenient and effective route. Preferred routes include subcutaneous, intradermal, intravenous and intramuscular routes. Other possible routes include oral administration, intrathecal, inhalation, transdermal application, or rectal administration. For the treatment of tumors which have not been completely resected, direct intratumoral injection is also intended.

Depending on the route of administration, the active compound may be coated in a material to protect the compound from the action of enzymes, acids and other natural conditions which may inactivate the compound. Thus it may be necessary to coat the composition with, or co-administer the composition with, a material to prevent its inactivation. For example, an enzyme inhibitors of nucleases or proteases (e.g., pancreatic trypsin inhibitor, diisopropylfluorophosphate and trasylol) or in an appropriate carrier such as liposomes (including water-in-oil-in-water emulsions as well as conventional liposomes (Strejan et al., (1984) *J. Neuroimmunol* 7:27).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like.

Parenteral compositions are preferably formulated in dosage unit form for ease of administration and uniformity of dosage. Dosage unit form refers to physically discrete units suited as unitary dosages for a mammalian subject; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

Other pharmaceutically acceptable carriers for the nucleic acid vaccine compositions according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

Antigens Associated with Pathogens

A major utility for the present invention is the use of the present nucleic acid compositions in therapeutic vaccine for cancer and for major chronic viral infections that cause morbidity and mortality worldwide. Such vaccines are designed to eliminate infected cells—this requires T cell responses as antibodies are often ineffective. The vaccines of the present invention, include, the antigenic epitope itself and an intercellular spreading protein such as VP22. In addition to the specific antigens and vectors employed in the Examples, the present invention is intended to encompass (a) a vector such as naked DNA, naked RNA, self replicating RNA replicons and viruses including vaccinia, adenoviruses, adeno-associated virus (AAV), lentiviruses and RNA alphaviruses;
(b) an additional antigen targeting or processing signal such as HSP70, calreticulin, the extracellular domain of Flt-3 ligand, domain II of Pseudomonas exotoxin ETA,; and
(c) a costimulatory signal, such as a B7 family protein, including B7-DC (see commonly assigned U.S. patent application Ser. No. 09/794,210 which is incorporated by reference in its entirety), B7.1, B7.2, soluble CD40, etc.).

Preferred antigens are preferably epitopes of pathogenic microorganisms against which the host is defended by effector T cells responses, including cytotoxic T lymphocyte (CTL) and delayed type hypersensitivity. These typically include viruses, intracellular parasites such as malaria, and bacteria that grow intracellularly such as mycobacteria and listeria. Thus, the types of antigens included in the vaccine compositions of this invention are any of those associated with such pathogens (in addition, of course, to tumor-specific antigens). It is noteworthy that some viral antigens are also tumor antigens in the case where the virus is a causative factor in cancer.

In fact, the two most common cancers worldwide, hepatoma and cervical cancer, are associated with viral infection. Hepatitis B virus(HBV) (Beasley, R. P. et al., Lancet 2, 1129-1133 (1981) has been implicated as etiologic agent of hepatomas. 80-90% of cervical cancers express the E6 and E7 antigens (exemplified herein) from one of four "high risk" human papillomavirus types: HPV-16, HPV-18, HPV-31 and HPV-45 (Gissmann, L. et al., Ciba Found Symp. 120, 190-207 (1986); Beaudenon, S., et al. Nature 321, 246-249 (1986). The HPV E6 and E7 antigens are the most promising targets for virus associated cancers in immunocompetent individuals because of their ubiquitous expression in cervical cancer. In addition to their importance as targets for therapeutic cancer vaccines, virus associated tumor antigens are also ideal candidates for prophylactic vaccines. Indeed, introduction of prophylactic HBV vaccines in Asia have decreased the incidence of hepatoma (Chang, M. H., et al. New Engl. J. Med. 336, 1855-1859 (1997), representing a great impact on cancer prevention.

Among the most important viruses in chronic human viral infections are human papillomavirus (HPV) hepatitis B virus (HBV), hepatitis C Virus (HCV), human immunodeficiency virus (HIV), Epstein Barr Virus (EBV) and herpes simplex virus (HSV).

In addition to its applicability to human cancer and infectious diseases, the present invention is also intended for use in treating animal diseases in the veterinary medicine context. Thus, the approaches described herein may be readily applied by one skilled in the art to treatment of veterinary herpesvirus infections including equine herpesviruses, bovine herpesviruses, Marek's disease virus in chickens and other fowl; animal retroviral diseases; pseudorabies and rabies and the like.

The following references set forth principles and current information in the field of basic, medical and veterinary virology and are incorporated by reference: *Fields Virology,* Fields, B N et al., eds., Lippincott Williams & Wilkins, NY, 1996; *Principles of Virology: Molecular Biology, Pathogenesis, and Control,* Flint, S. J. et al., eds., Amer Society for Microbiology, Washington, 1999; *Principles and Practice of Clinical Virology,* 4th Edition, Zuckerman. A. J. et al., eds, John Wiley & Sons, NY, 1999; *The Hepatitis C Viruses,* by Hagedorn, C H et al., eds., Springer Verlag, 1999; *Hepatitis B Virus: Molecular Mechanisms in Disease and Novel Strategies for Therapy,* Koshy, R. et al., eds, World Scientific Pub Co, 1998; *Veterinary Virology,* Murphy, F. A. et al., eds., Academic Press, NY, 1999; *Avian Viruses: Function and Control,* Ritchie, B. W., Iowa State University Press, Ames, 2000; *Virus Taxonomy: Classification and Nomenclature of Viruses: Seventh Report of the International Committee on Taxonomy of Viruses,* by M. H. V. Van Regenmortel, M H V et al., eds., Academic Press; NY, 2000.

Delivery of Vaccine Nucleic Acid to Cells and Animals

The Examples below describe certain preferred approaches to delivery of the vaccines of the present invention.

DNA delivery, for example to effect what is generally known as "gene therapy" involves introduction of a "foreign" DNA into a cell and ultimately, into a live animal. Several general strategies for gene therapy have been studied and have been reviewed extensively (Yang, N-S., *Crit. Rev. Biotechnol.* 12:335-356 (1992); Anderson, W. F., *Science* 256:808-813 (1992); Miller, A. S., *Nature* 357:455-460 (1992); Crystal, R. G., *Amer. J. Med.* 92(suppl 6A):44S-52S (1992); Zwiebel, J. A. et al., *Ann. N.Y. Acad. Sci.* 618:394-404 (1991); McLachlin, J. R. et al., *Prog. Nucl. Acid Res. Molec. Biol.* 38:91-135 (1990); Kohn, D. B. et al., *Cancer Invest.* 7:179-192 (1989), which references are herein incorporated by reference in their entirety).

One approach comprises nucleic acid transfer into primary cells in culture followed by autologous transplantation of the ex vivo transformed cells into the host, either systemically or into a particular organ or tissue.

For accomplishing the objectives of the present invention, nucleic acid therapy would be accomplished by direct transfer of a the functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the antigen-containing expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful "gene transfer" reported in the art include: (a) direct injection of plasmid DNA into mouse muscle tissues, which led to expression of marker genes for an indefinite period of time (Wolff, J. A. et al., *Science* 247:1465 (1990); Acsadi, G. et al., *The New Biologist* 3:71 (1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., *J. Biol. Chem.* 265:17285 (1990); Koleko, M. et al., *Human Gene Therapy* 2:27 (1991); Ferry, N. et al., *Proc. Natl. Acad. Sci. USA* 88:8387 (1991)); (d) intratracheal infusion of recombinant adenovirus into lung tissues was effective for in vivo transfer and prolonged expression of foreign genes in lung respiratory epithelium (Rosenfeld, M.

A. et al., *Science* 252:431 (1991); (e) Herpes simplex virus vectors achieved in vivo gene transfer into brain tissue (Ahmad, F. et al., eds, *Miami Short Reports—Advances in Gene Technology: The Molecular Biology of Human Genetic Disease*, Vol 1, Boehringer Manneheiml Biochemicals, USA, 1991).

Retroviral-mediated human therapy utilizes amphotrophic, replication-deficient retrovirus systems (Temin, H. M., *Human Gene Therapy* 1:111 (1990); Temin et al., U.S. Pat. No. 4,980,289; Temin et al., U.S. Pat. No. 4,650,764; Temin et al., U.S. Pat. No. 5,124,263; Wills, J. W. U.S. Pat. No. 5,175,099; Miller, A. D., U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D. G. et al., *Mol. Cell. Biol.* 10:4239 (1990). This condition is met by certain of the preferred target cells into which the present DNA molecules are to be introduced, i.e., actively growing tumor cells. Gene therapy of cystic fibrosis using transfection by plasmids using any of a number of methods and by retroviral vectors has been described by Collins et al., U.S. Pat. No. 5,240,846.

The DNA molecules encoding the fusion polypeptides of the present invention may be packaged into retrovirus vectors using packaging cell lines that produce replication-defective retroviruses, as is well-known in the art (see, for example, Cone, R. D. et al., *Proc. Natl. Acad. Sci. USA* 81:6349-6353 (1984); Mann, R. F. et al., *Cell* 33:153-159 (1983); Miller, A. D. et al., *Molec. Cell. Biol.* 5:431-437 (1985),; Sorge, J., et al., *Molec. Cell. Biol.* 4:1730-1737 (1984); Hock, R. A. et al., *Nature* 320:257 (1986); Miller, A. D. et al., *Molec. Cell. Biol.* 6:2895-2902 (1986). Newer packaging cell lines which are efficient an safe for gene transfer have also been described (Bank et al., U.S. Pat. No. 5,278,056.

This approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M. S., In: *Virology*, Fields, B N et al., eds, Raven Press, New York, 1990, p. 1679; Berkner, K. L., *Biotechniques* 6:616 Sep. 19, 1998), Strauss, S. E., In: *The Adenoviruses*, Ginsberg, H S, ed., Plenum Press, New York, 1984, chapter 11), herpes simplex virus (HSV) for neuron-specific delivery and persistence. Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R. J. et al., *EMBO J.* 10:3941 (1991) according to the present invention.

Another vector which can express the DNA molecule of the present invention, and is useful in the present therapeutic setting, particularly in humans, is vaccinia virus, which can be rendered non-replicating (U.S. Pat. Nos. 5,225,336; 5,204,243; 5,155,020; 4,769,330; Sutter, G et al., *Proc. Natl. Acad. Sci. USA* (1992) 89:10847-10851; Fuerst, T. R. et al., *Proc. Natl. Acad. Sci. USA* (1989) 86:2549-2553; Falkner F. G. et al.; *Nucl. Acids Res* (1987) 15:7192; Chakrabarti, S et al., *Molec. Cell. Biol.* (1985) 5:3403-3409). Descriptions of recombinant vaccinia viruses and other viruses containing heterologous DNA and their uses in immunization and DNA therapy are reviewed in: Moss, B., *Curr. Opin. Genet. Dev.* (1993) 3:86-90; Moss, B. *Biotechnology* (1992) 20: 345-362; Moss, B., *Curr Top Microbiol Immunol* (1992) 158: 25-38; Moss, B., *Science* (1991) 252:1662-1667; Piccini, A et al., *Adv. Virus Res.* (1988) 34:43-64; Moss, B. et al., *Gene Amplif Anal* (1983) 3:201-213.

In addition to naked DNA or RNA, or viral vectors, engineered bacteria may be used as vectors. A number of bacterial strains including Salmonella, BCG and *Listeria monocytogenes* (LM) (Hoiseth & Stocker, *Nature* 291, 238-239 (1981); Poirier, T P et al. *J. Exp. Med.* 168, 25-32 (1988); (Sadoff, J. C., et al., *Science* 240, 336-338 (1988); Stover, C. K., et al., *Nature* 351, 456-460 (1991); Aldovini, A. et al., *Nature* 351, 479-482 (1991); Schafer, R., et al., *J. Immunol.* 149, 53-59 (1992); Ikonomidis, G. et al., *J. Exp. Med.* 180, 2209-2218 (1994)). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R. S. et al., *Proc. Natl. Acad. Sci. USA* 88:2726 (1991); Zelenin, A. V. et al., *FEBS Lett.* 280:94 (1991); Zelenin, A. V. et al., *FEBS Lett.* 244:65 (1989); Johnston, S. A. et al., *In Vitro Cell. Dev. Biol.* 27:11 (1991)). Furthermore, electroporation, a well-known means to transfer genes into cell in vitro, can be used to transfer DNA molecules according to the present invention to tissues in vivo (Titomirov, A. V. et al., *Biochim. Biophys. Acta* 1088:131 ((1991)).

"Carrier mediated gene transfer" has also been described (Wu, C. H. et al., *J. Biol. Chem.* 264:16985 (1989); Wu, G. Y. et al., *J. Biol. Chem.* 263:14621 (1988); Soriano, P. et al., *Proc. Natl. Acad. Sci. USA* 80:7128 (1983); Wang, C-Y. et al., *Proc. Natl. Acad. Sci. USA* 84:7851 (1982); Wilson, J. M. et al., *J. Biol. Chem.* 267:963 (1992)). Preferred carriers are targeted liposomes (Nicolau, C. et al., *Proc. Natl. Acad. Sci. USA* 80:1068 (1983); Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

Plasmid DNA used for transfection or microinjection may be prepared using methods well-known in the art, for example using the Quiagen procedure (Quiagen), followed by DNA purification using known methods, such as the methods exemplified herein.

Having now generally described the invention, the same will be more readily understood through reference to the following examples which are provided by way of illustration, and are not intended to be limiting of the present invention, unless specified.

EXAMPLE I

Materials and Methods for HSV-VP22 DNA Study

Plasmid DNA Construction

The pcDNA3 expression vector and pcDNA3-E7 have been described (Chen, C H et al., 1999, *Gene Ther* 6:1972-81; Ji, H. et al., 1999, *Human Gene Therapy* 10:2727-2740). pcDNA3 has been used successfully in DNA vaccine induced immune responses and antitumor effects (Chen, C H et al., 2000, *Cancer Res* 60:1035-42; co-pending, commonly assigned U.S. patent applications U.S. Ser. No. 09/421,608, filed 20, Oct. 1999, U.S. Ser. No. 0911,097, filed 9, Feb. 2000 and U.S. Ser. No. 09/693,450; filed 20, Oct. 2000, which are incorporated by reference). For the generation of pcDNA3-VP22, VP22 was subcloned from pVP22/myc-His (Invitrogen, Carlsbad, Calif.) into the unique EcoRV and BamHI cloning sites of the pcDNA3.1 (−) expression vector (Invitrogen, Carlsbad, Calif.) downstream of the CMV promoter. The generation of pcDNA3-E7 has been described previously (Chen et al., supra). For the generation of pcDNA3-VP22/E7, VP22 was subcloned from pcDNA3-VP22 into the unique EcoRV and BamHI cloning sites of the pcDNA3-E7. For the generation of pcDNA3-E7(E/B), which contains E7 with EcoRI and BamHI restriction sites on the flanking ends of E7, PCR was used to amplify the E7 fragment with pcDNA3-E7 and a set of primers:

5'-ggggaattcatggagatacaccta-3' and (SEQ ID NO:1)

5'-ggtggatccttgagaacagatgg-3'. (SEQ ID NO:2)

The amplified product was further cloned into the EcoRI/BamHI sites of pcDNA3. For the generation of pcDNA3-VP22(1-267)/E7, a DNA fragment encoding VP22(1-267) was first amplified using PCR with pcDNA3-VP22 and a set of primers:

(SEQ ID NO:3)
5'-gggtctagaatgacctctcgccgctccgt-3' and (SEQ ID NO:4)
5'-ggggaattcgtcctgcaccacgtctggat-3'.

The amplified product was cloned into the XbaI/EcoRI cloning sites of pcDNA3-E7(E/B).

For the generation of pcDNA3-GFP, DNA fragment encoding GFP was first amplified using PCR with pEGFPN1 DNA (Clontech, Palo Alto, Calif.) and a set of primers:

(SEQ ID NO:5)
5'-atcggatccatggtgagcaagggcgaggag-3' and (SEQ ID NO:6)
5'-gggaagctttacttgtacagctcgtccatg-3'.

The amplified product was cloned into the BamHI/HindIII cloning sites of pcDNA3. For the generation of pcDNA3-VP22/GFP, VP22 was subcloned from pcDNA3-VP22 into the unique EcoRV and BamHI cloning sites of the pcDNA3-GFP. For construction of pcDNA3-E7/GFP, GFP was isolated from pcDNA3-GFP and cloned into BamHI/HindIII sites of pcDNA3-E7(E+B). For construction of VP22/E7/GFP, VP22 was amplified by and a set of primers:

(SEQ ID NO:7)
5'-gggtctagaatgacctctcgccgctccgt-3' and (SEQ ID NO:8)
5'-ggggaattcctcgacgggccgtctggggc-3' and cloned into XbaI/EcoRI sites of pcDNA3-E7/GFP. For construction of pcDNA3-VP22(1-267)/E7/GFP, VP22(1-267) was isolated from pcDNA3-VP22(1-267) and cloned into XbaI/EcoRI sites of pcDNA3-E7/GFP.

The generation of pSC11-E7 has been described previously (10). For cloning pSC11-VP22/E7, VP22 was isolated from pcDNA3-VP22/E7 by NotI/PmeI and coned into NotI/SamI sites of pSC11 vector. To generate pSC11-VP22, VP22 was isolated from pcDNA3-VP22 by NotI/PmeI and cloned into NotI/SamI sites of pSC11 vector.

For the generation of pcDNA3-TAT/E7, the following complementary oligomers encoding MRKKRRQRRR (SEQ ID NO:9) (Green, M et al., 1988, *Cell* 55:1179-88; Schwarze, S R et al., 1999, *Science* 285:1569-72) were synthesized:

(SEQ ID NO:10)
5'-ctagaatgtacggccgcaagaaacgccgccagcgccgccgcg-3'
and (SEQ ID NO:11)
5'-aattcgcggcggcgctggcggcgtttcttgcggccgtacatt-3'.

The oligomers were annealed and cloned into the XbaI/EcoRI sites of pcDNA3-E7(E/B).

For the generation of pcDNA3-E7/MTS, the following complementary oligomers encoding AAVLLPVLLAAP (SEQ ID NO:12) (Rojas, M et al., 1998, *Nat Biotechnol* 16:370-5) were synthesized:

(SEQ ID NO:13)
5'-gatccgcagccgttcttctccctgttcttcttgccgcaccta-3'
and (SEQ ID NO:14)
5'-agcttagggtgcggcaagaagaacagggagaagaacggctgcg-3'.

The oligomers were annealed and cloned into the BamHI/HindIII sites of pcDNA3-E7(E/B).

For the generation of pcDNA3-AH/E7, the following complementary oligomers encoding MRQIKIWFQNR-RMKWKK (SEQ ID NO:15) (Derossi, D et al., 1994, *J Biol Chem* 269:10444-10450) were synthesized:

5'-ctagaatgcgccaaatcaaaatctggttccagaatcgacgaatgaagtggaaaaaag-3' and (SEQ ID NO:16)

5'-aattcttttttccacttcattcgtcgattctggaaccagattttgatttggcgcatt-3'. (SEQ ID NO:17)

The oligomers were annealed and cloned into the XbaI/EcoRI sites of pcDNA3-E7(E/B). The accuracy of all the DNA constructs was confirmed by sequencing.

DNA Vaccination

Preparation of DNA-coated gold particles and gene gun particle-mediated DNA vaccination was performed using a helium-driven gene gun (Bio-rad, Hercules, Calif.) according to a previously described protocol (Chen et al., supra). DNA-coated gold particles (1 μg DNA/bullet) were delivered to the shaved abdominal region of C57BL/6 mice using a helium-driven gene gun (Bio-rad, Hercules, Calif.) with a discharge pressure of 400 p.s.i.

Fluorescence Microscopy for In Vitro Distribution of VP22/E7

293 $D^bK^b$ cells (provided by Dr. J C Yang, National Cancer Institute, NIH; Bloom, M B et al., 1997, *J Exp Med* 185:453-459) were utilized for an in vitro assay of GFP expression. 20 μg of VP22, E7/GFP, VP22(1-267)/E7/GFP or VP22/E7/GFP DNA were transfected into $5 \times 10^6$ 293 $D^bK^b$ cells using lipofectamine 2000 (Life Technologies, Rockville, Md.). Transfected cells were fixed with 4% paraformaldehyde in 1×PBS, permeabilized with 1×PBS containing 0.05% saponin and 1% BSA, then incubated with 0.5 μg/ml of primary anti-calnexin antibody (Stressgen Biotechnologies, Victoria, B C). Samples were acquired with the Noran Oz confocal laser scanning microscope system using Invertension® software (v. 6.5). Slides were imaged with an Olympus IX-50 inverted microscope (100× magnification).

Immunohistochemical Staining for In Vivo Distribution of VP22/E7

Mice were sacrificed 3 days after vaccination with pcDNA3-VP22/GFP or pcDNA3-. Skin was biopsied, fixed, paraffin-embedded, and cut into 5 μm sections. After deparaffinization and hydration, slides were incubated with rabbit anti-GFP polyclonal antibody (1:200 dilution; Molecular Probes, Eugene, Oreg.) followed by biotinylated goat anti-rabbit IgG (1:200 dilution) and avidin-biotin complex (1:100 dilution; Vector, Burlingame, Calif.). The slides were developed by adding DAB substrate solution (DAKO, Carpenteria, Calif.) and counterstained with Mayer's hematoxylin. Stained slides were dehydrated, mounted and observed by light microscopy.

Intracellular Cytokine Staining

Cell surface marker staining of CD8 or CD4 and intracellular cytokine staining for IFN-γ and IL-4 as well as FACScan analysis was performed using conditions described previously (Chen et al., supra). Prior to FACScan, splenocytes from naïve or vaccinated groups of mice were incubated for 20 hours with either 1 μg/ml of E7 peptide (aa 49-57) (Feltkamp et al., supra) containing MHC class I epitope for detecting E7-specific CD8$^+$ T cell precursors or 10 μg/ml of E7 peptide (aa 30-67) (Tindle, R W et al., 1991, *Proc Natl Acad Sci USA* 88:5887-5891) containing MHC class II peptide for detecting E7-specific CD4$^+$ T cell precursors. The number of IFN-γ-secreting CD8$^+$ and CD4$^+$ T cells was analyzed using flow cytometry. Phycoerythrin-conjugated CDS antibody, fluorescein isothiocyanate (FITC)-conjugated anti-IFNγ antibody, and the immunoglobulin isotype control antibody (rat IgG1) were all purchased from PharMingen (San Diego, Calif.). Analysis was performed on a Becton Dickinson FACScan with CELLQuest software (Becton Dickinson Immunocytometry Systems, Mountain View, Calif.).

Cytotoxic T Lymphocyte (CTL) Assays

Splenocytes from vaccinated mice were harvested 2 weeks after vaccination and cultured with the E7 peptide (aa 49-57) containing an MHC class I epitope (Feltkamp, M C et al., 1993, *Eur J Immunol* 23:2242-2249) at a concentration of 1 μg/ml in a total volume of 2 ml of RPMI 1640, supplemented with 10% (vol/vol) fetal bovine serum, 50 units/ml penicillin and streptomycin, 2 mM L-glutamine, 1 mM sodium pyruvate, 2 mM nonessential amino acids in a 24-well tissue culture plate for 6 days. Splenocytes served as effector ("E") cells while TC-1 tumor cells (Lin, K-Y et al., 1996, *Cancer Research* 56:21-26) were target ("T") cells. CTL assays were performed in 96-well round-bottom plates and measured quantitative release of lactate dehydrogenase (LDH) (Corr et al., 1999, *J Immunol* 163:4721-4727). Effector cells and targets cells ($1 \times 10^4$ per well) were mixed at various ratios (1:1, 5:1, 15:1, and 45:1) in a final volume of 200 μl. After 5 hr incubation at 37° C., 50 μl of medium was collected from each well and LDH measured according to the manufacturer's protocol (CytoTox® assay kit, Promega Corp., Madison, Wis.). Cytolysis was calculated using the following formula $$\% \text{ Lysis} = [(A-B)/(C-D)] \times 100$$

where A is the experimental effector signal value, B is the effector spontaneous background signal value, C is maximum signal value from target cells, D is the target spontaneous background signal value.

CTL Assay Using Transfected or Vaccinia-Infected 293 $D^bK^b$ Cells as Target Cells 20 μg of pcDNA3 (no insert), VP22, E7, or VP22/E7 DNA were transfected into $5 \times 10^6$ 293 $D^bK^b$ cells using lipofectamine 2000 (Life Technologies, Rockville, Md.). Transfected 293 $D^bK^b$ cells were used as target cells while an E7-specific CD8$^+$ T cell line (Wang, T-L et al., 2000, *Gene Therapy* 7:726-733) served as effector cells. Untransfected 293 $D^bK^b$ cells were used as a negative control. Cells were collected 40-44 hr after transfection. Cytolysis was determined as above. E:T ratios were 1:1, 3:1, 9:1, and 27:1.

In a second CTL assay, vaccinia-infected 293 $D^bK^b$ cells served as target cells using a previously described protocol (Ji et al., supra). $5 \times 10^6$ 293 $D^bK^b$ cells were infected with $10^7$ PFU of wild-type, VP22, E7, or VP22/E7 vaccinia. Cells were collected 16 hr after infection. Cytolysis was determined as above (E:T ratios were 1:1, 5:1, 15:1, and 45:1).

In Vivo Tumor Protection

Mice (5 per group) were vaccinated via gene gun with 2 μg of pcDNA3 (no insert), VP22, E7, VP22(1-267)/E7, or VP22/E7 DNA. One week later, mice were boosted with the same regimen as the first vaccination. One week after the last vaccination, each mouse was challenged s.c. with $5 \times 10^4$ TC-1 tumor cells in the right leg and then monitored twice weekly. The day of first gene gun vaccination was considered the day 0 for counting posttreatment survival days.

In Vivo Tumor Therapy

Tumor cells and DNA vaccines were prepared as described above. Each mouse (5 per group) were challenged i.v. with $10^4$ TC-1 tumor cells on day 0. Three days later, mice received 2 μg of pcDNA3 (no insert), VP22, E7, or VP22/E7 DNA via gene gun. One week later, mice were boosted using the same regimen. On day 21, mice were sacrificed and the lungs evaluated for pulmonary nodules which were counted, and the lungs weighed by experimenters blinded to sample identity. When compared to determining the percent of tumor free mice in the subcutaneous tumor model, the mean number of tumor nodules in the pulmonary tumor model is a more sensitive indicator of the vaccine's antitumor effect. The pulmonary tumor model allows detection of subtle differences between groups that might go undetected in the subcutaneous tumor model.

In Vivo Antibody Depletion Experiment

In vivo antibody depletions have been described previously (Lin et al, supra). Briefly, mice were vaccinated with 2 µg VP22/E7 DNA via gene gun, boosted one week later, and challenged s.c. with $5 \times 10^4$ TC-1 tumor cells/mouse. Depletion treatment was initiated one week prior to tumor challenge. Depletion was terminated on day 63 after tumor challenge. MAb GK1.5 (Dialynas et al., 1983, *J. Immunol.* 131:2445) was used for CD4 depletion. MAb 2.43 (Sarmiento et al., 1980, *J. Immunol.* 125:2665-2672) was used for CD8 depletion, and MAb PK136 (Koo et al., 1986, *J. Immunol.* 137:3742) was used for NK1.1 depletion.

EXAMPLE II

Enhanced Intercellular Spreading of VP22 Fusion Proteins

We initially generated several DNA constructs (E7, VP22, VP22/E7, VP22(1-267)/E7, E7/GFP, VP22/GFP, VP22/E7/GFP, and VP22(1-267)/E7/GFP) using a mammalian cell expression vector (pcDNA3). To demonstrate if VP22/E7 protein generated enhanced intercellular spreading of E7 in 293 $D^bK^b$ cells, we used green fluorescent protein (GFP) as a marker protein and examined green fluorescence. 293 $D^bK^b$ cells were transfected with E7/GFP, VP22(1-267)/E7/GFP, or VP22/E7/GFP DNA. We performed fluorescent microscopic examination of 293 $D^bK^b$ cells to investigate the topological distribution of GFP protein. We observed significant spread of GFP protein in cells transfected with VP22/E7/GFP DNA but not in cells transfected with E7/GFP or VP22(1-267)/E7/GFP DNA (FIG. 1A).

We also administered VP22/GFP or GFP intradermally into C57BL/6 mice via gene gun. To demonstrate if the linkage of VP22 to protein led to enhanced intercellular spreading of the linked protein in vaccinated mice, we used green fluorescent protein (GFP) as a marker protein since we had difficulty detecting E7 in paraffin-embedded tissue sections using available E7-specific antibodies. pcDNA3, pcDNA3-VP22/GFP, or pcDNA3-GFP was administered intradermally into C57BL/6 mice via gene gun. The skin at the vaccinated sites was biopsied 3 days following vaccination and processed for the detection of GFP using immunocytochemical staining. As shown in FIG. 1B, a widespread distribution of positive brown staining was observed in the epidermis and skin appendices from mice vaccinated with pcDNA3-VP22/GFP, with some positive staining of nuclei in the epidermis. In contrast, only a few positive cells were observed in the epidermis of pcDNA3-GFP-vaccinated mice. These results suggested that the linkage of VP22 to protein led to enhanced intercellular spreading of the linked protein.

EXAMPLE III

Enhanced T Cell Activities Induced by VP22 Linked to Antigen

The observed increase in intercellular spreading of the marker protein within the epidermis raises the possibility of generating an increased number of antigen presenting cells (APCs) that present the linked protein since the epidermis is rich with Langerhans' cells, the professional APC precursors. To further investigate if such increased spreading can lead to enhanced antigen-specific T cell activities, we linked VP22 to a model antigen, HPV-16 E7, which is associated with a majority of cervical cancers. E7 is important in the induction and maintenance of cellular transformation and co-expressed in most HPV-containing cervical cancers and their precursor lesions and therefore represents an ideal target for vaccine development (21).

The importance of CD8$^+$ cytotoxic T cells for the control of viral infections and neoplasms has been demonstrated in several pre-clinical models (9, 22). To determine whether vaccination of mice with the pcDNA3-VP22/E7 DNA vaccine enhanced E7-specific CD8$^+$ T cell activity, we performed intracellular cytokine staining for E7-specific CD8$^+$ T cell precursors using splenocytes from vaccinated mice.

As shown in FIG. 2A, mice vaccinated with VP22/E7 DNA exhibited a greater than 50-fold increase in E7-specific IFN-γ$^+$ CD8$^+$ T cell precursors (576/3×10$^5$ splenocytes) compared to mice vaccinated with wild-type E7 DNA (9/3×10$^5$ splenocytes). These results indicated that the addition of VP22 to E7 significantly enhanced E7-specific CD8$^+$ T cell-mediated immune responses and that fusion of E7 to VP22 was essential for this observed enhancement since VP22 mixed to E7 (VP22+E7 DNA) did not generate enhancement of CD8$^+$ T cell activity. Furthermore, the linkage of irrelevant proteins (such as GFP) to E7 did not generate enhancement of E7-specific CD8+ T cell activity (data not shown).

To explore if the property of intercellular spreading of VP22 is important for the observed enhancement of E7-specific CD8$^+$ T cell activity, we generated VP22(1-267) lacking 34 C-terminal residues, a mutant that is unable to spread intercellularly (4). We observed that the linkage of the mutant VP22(1-267) to E7 failed to enhance the number of E7-specific CD8$^+$ T cell precursors in vaccinated mice (FIG. 2A). The property of intercellular spreading generated by full-length VP22 was important for the enhancement of E7-specific CD8$^+$ T cell activity.

While addition of VP22 to E7 led to enhanced E7-specific CD8$^+$ T cell activities, we did not detect a significant difference in the number of E7-specific IFN-γ-secreting CD4$^+$ T cells (FIG. 2B) or IL-4-secreting CD4 T cells among the various vaccination groups. Using a direct ELISA, we detected no significant difference in E7-specific antibody responses in the sera of mice vaccinated with various DNA vaccines (data not shown).

EXAMPLE IV

VP22-E7 DNA Vaccine Induces E7-Specific Cytotoxic T Lymphocytes

Figure 3:
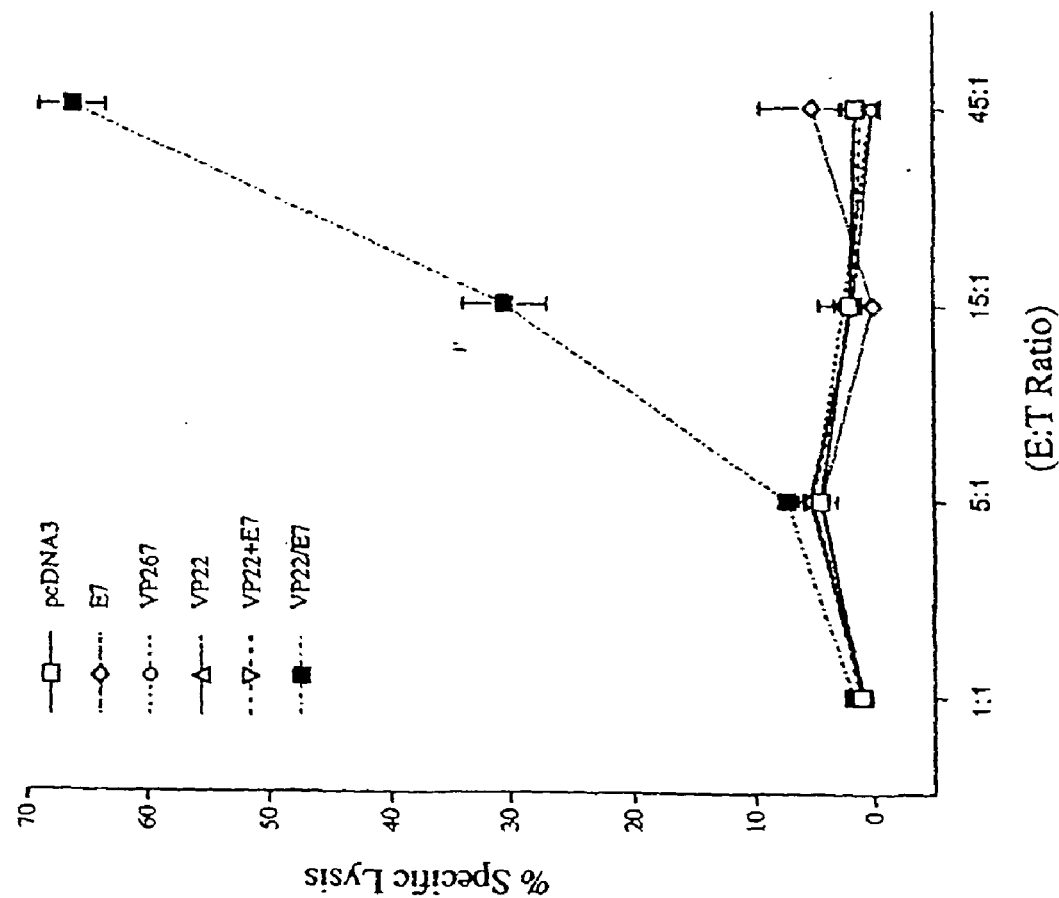
FIG. 3. CTL assay using 293 $D^bK^b$ cells pulsed with E7 peptide and splenocytes from vaccinated mice. TC-1 tumor cells served as target cells. CTL assays were performed with various E:T ratios using splenocytes obtained from vaccinated mice. Note: Vaccination with VP22/E7 DNA generated the highest CTL activity compared to vaccination with E7 DNA or empty plasmid.

Since CD8$^+$ cytotoxic T cells have been implicated as important effector cells for generating antitumor effects, we used CTL assays to study E7-specific CTL killing generated in mice vaccinated with various DNA vaccines. We used splenocytes from mice vaccinated with various DNA vaccines as effector cells and TC-1 tumor cells as target cells. We observed that highest CTL activity in mice vaccinated with VP22/E7 compared to mice vaccinated with pcDNA3 (no insert), VP22, or E7 DNA (FIG. 3). Our data indicated that the CTL activity correlated with the frequency of E7-sepcific CD8+ T cell precursors generated by each DNA vaccine.

One of the potential explanations that may account for the observed enhancement of E7-specific CD8+ T cell activity in mice vaccinated with VP22/E7 DNA may be the enhanced MHC class I presentation of E7 in cells transfected with this chimeric vaccine. We therefore conducted CTL assays to determine if cells transfected with pcDNA3 (no insert), VP22, E7, or VP22/E7 DNA presented E7 directly to a $D^b$-restricted E7-specific CD8+ T cell line. We chose 293 $D^bK^b$ cells (15) as target cells because they have been shown to have a stable high transfection efficiency (up to 80%) and express the murine MHC class I molecule, $D^b$. As shown in FIG. 4A, 293 $D^bK^b$ cells transfected with VP22/E7 DNA displayed significantly higher percentages of specific lysis at the 9:1 (22.8±1.8% versus 6.2±1.5%, p<0.001) and 27:1 (48.1±2.4% versus 13.0±1.6%, p<0.001) E:T ratios compared to cells transfected with wild-type E7 DNA. Since intercellular spreading of VP22/E7 may affect the results of this assay by generating more E7-positive target cells, we performed a CTL assay using vaccinia-infected target cells to alleviate this concern. Vaccinia have been shown to infect nearly 100% of target cells. We used a C57BL/6-derived dendritic cell line (23) infected with E7, VP22, or VP22/E7 vaccinia as target cells using a previously described protocol (8) and observed a higher percentage of lysis for dendritic cells infected with VP22/E7 vaccinia compared to cells infected with other vaccinia (FIG. 4B). These data suggested that cells expressing VP22/E7 may present E7 antigen through the MHC class I pathway more efficiently than cells expressing wild-type E7.

EXAMPLE V

Antitumor Effects of VP22-E7 DNA Vaccine: Tumor Protection

To determine if the observed enhancement in E7-specific CD8+ T cell-mediated immunity translated to a significant E7-specific antitumor effect, we performed an in vivo tumor protection experiment using a previously characterized E7-expressing tumor model, TC-1. As shown in FIG. 5A, 100% of mice receiving the VP22/E7 DNA vaccine remained tumor-free 63 days after TC-1 challenge. In contrast, all of the unvaccinated mice and mice receiving pcDNA3 (no insert), VP22, or wild-type E7 developed tumor growth within 14 days after tumor challenge. We also observed that fusion of E7 to VP22 was required for antitumor immunity, since VP22 mixed to E7 (VP22+E7 DNA) did not generate enhancement of tumor protection. Furthermore, the linkage of the mutant VP22(1-267) to E7 failed to generated a significant antitumor effect in vaccinated mice (FIG. 5A). The property of intercellular spreading generated by linkage of full-length VP22 to E7 was important for the observed enhancement of E7-specific tumor protection.

EXAMPLE VI

Antitumor Effects of VP22-E7 DNA Vaccine: Therapy of Metastases

We then investigated the therapeutic potential of the chimeric VP22/E7 DNA construct in treating TC-1 tumor metastases in the lungs. As shown in FIG. 5B, mice vaccinated with VP22/E7 DNA exhibited the lowest mean number of pulmonary nodules (0.75±0.95) compared to mice vaccinated with wild-type E7 DNA (32.6±2.5), or VP22 DNA (13±2.58) (one-way ANOVA, p<0.001). Interestingly, vaccination with VP22 DNA generated a weak non-specific antitumor effect in the lung metastasis model. The results from the tumor protection and treatment experiments indicated that linkage of VP22 to E7 dramatically enhanced antitumor effects against the growth of TC-1 tumors.

To determine the subset of lymphocytes important for the antitumor effects, we performed in vivo antibody depletion experiments. As shown in FIG. 5C, all naïve mice and VP22/E7 DNA-vaccinated mice depleted of CD8+ T cells grew tumors within 14 days after tumor challenge. In contrast, all of the non-depleted mice and all of the mice depleted of CD4+ T cells remained tumor-free 63 days after tumor challenge. 40% of NK1.1-depleted mice grew tumors 6 weeks after tumor injections. These results suggested that CD8+ T cells but not CD4+ T cells are essential for the antitumor immunity generated by the VP22/E7 DNA vaccine. NK1.1 cells may also contribute to the antitumor effect generated by the chimeric VP22/E7 DNA vaccine.

EXAMPLE VII

Three Other Trafficking Proteins Did Not Potentiate CD8+ T Cell Immune Responses The success of the VP22/E7 DNA vaccine warranted testing of other proteins with trafficking properties. For example, the TAT protein has been shown to have transcellular transport properties (11, 12). In addition, a peptide containing nine amino acids of TAT (RKKRRQRRR) (SEQ ID NO:18) conjugated with ovalbumin (OVA) was able to generate higher CTL activity in mice were vaccinated with TAT-OVA compared to mice vaccinated with OVA (24). Another molecule with similar properties is the membrane-translocation sequence (MTS), which has also been shown to have transmembrane permeability. The amino acid residues accounting for this property have been narrowed down to twelve amino acids (AAVLLPVLLAAP) (SEQ ID NO:12) (13). Finally, the third helix of the Antennapedia homeodomain of *Drosophila* has also been shown to have membrane translocation properties and sixteen amino acid residues have been shown to account for this effect (RQIKIWFQNRRMKWKK) (SEQ ID NO:19) (14). The present inventors tested chimeric proteins that include these molecules will result in similar effects to that observed with VP22/E7.

Figure 6:
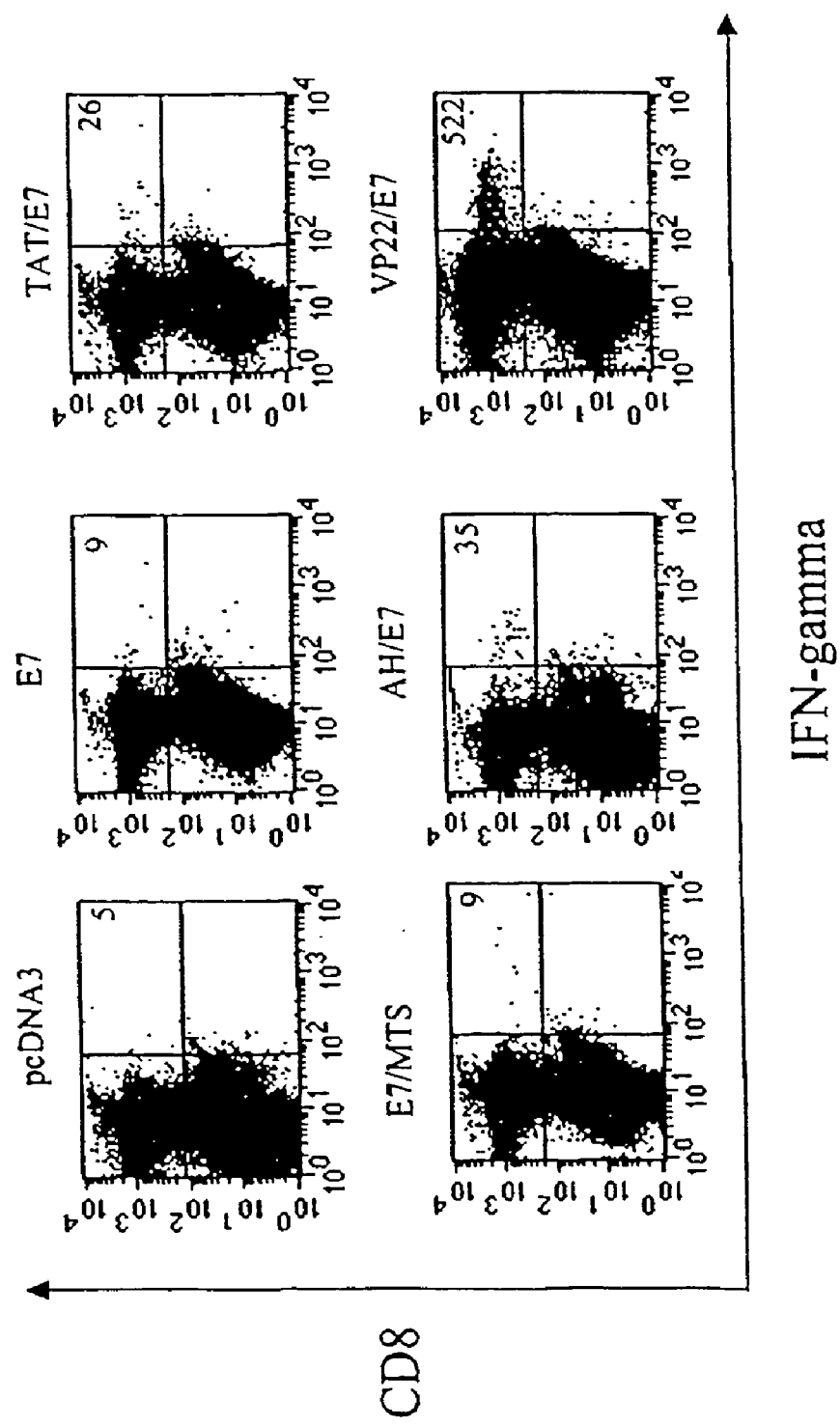
FIG. 6. Flow cytometry analysis of IFN-γ-secreting E7-specific CD8$^+$ T cell precursors in mice vaccinated with various recombinant DNA vaccines. Mice were vaccinated via gene gun with 2 μg of pcDNA3, E7, TAT/E7, E7/MTS, AH/E7, or VP22/E7 DNA. One week later, mice were boosted with the same regimen as the first vaccination. Splenocytes from vaccinated mice were cultured in vitro with 1 μg/ml of E7 peptide (aa 49-57) overnight and analyzed for both CD8 and intracellular IFN-γ using flow cytometry analysis. Note: Vaccination of mice with VP22/E7 DNA generated the highest frequency of IFN-γ$^+$ CD8$^+$ double positive T cells compared to the other groups. The data from intracellular cytokine staining shown here are from one representative experiment of two performed.

These polypeptides were therefore linked to E7 at the DNA level. Mice were vaccinated with each construct in order to examine the E7-specific immune responses generated by these vaccines in comparison to VP22/E7 DNA. We performed intracellular cytokine staining for E7-specific CD8+ T cell precursors using splenocytes from vaccinated mice. As shown in FIG. 6, the linkage of the DNA sequence encoding the characterized membrane translocation region of each of these proteins to E7 did not generate such a dramatic enhancement of E7-specific CD8+ T cell immune responses as we have observed with HSV-1 VP22. These results showed the advantages of VP22/E7 DNA over these other tested constructs. Therefore, the mere fact that a protein is identified as a "trafficking protein" does not mean that it will have the unexpected immunostimulatory activity of VP22 when used in a chimeric DNA construct in combination with antigen-coding DNA.

Discussion of Examples I-VII

As shown above, E7 linked to VP22 enhanced intercellular spreading. We demonstrated that VP22/E7 DNA generated a greater number of E7 specific CD8+ T cells than did E7 DNA alone or fused to VP22(1-267) DNA that lacks the property of intercellular spreading (4). We also found that VP22/E7 generated a stronger antitumor effect than did E7 or VP22(1-267)/E7, proving that the antitumor effect is CD8-dependent. Finally, DNA vaccines encoding HIV-TAT, MTS, or the third helix of the Antennapedia homeodomain linked to E7 did not generate T cell-stimulatory and antitumor effects that were as potent as those generated by VP22/E7 DNA.

A dramatic increase in the number of E7-specific CD8+ T cell precursors was observed in mice vaccinated with VP22/E7 (FIG. 2). One explanation for this enhancement is that intradermal administration of VP22/E7 DNA introduces DNA directly into professional antigen presenting cells (APCs) in the skin (25), allowing transfected APCs to directly present E7 through the MHC class I pathway. Another important reason for this observed enhancement is that the linkage VP22 to E7 may facilitate the spreading of antigen from VP22/E7 DNA-transfected cells to surrounding APCs, increasing the number of APCs that present E7 through MHC class I pathway. Finally, our data indicated that the linkage of VP22 to E7 is capable of presenting the antigen more efficiently in transfected cells. As a result, the number of E7-specific CD8$^+$ T cell precursors was significantly enhanced in vaccinated mice.

Another potentially important explanation for the observed enhancement of E7-specific CD8$^+$ T cell immune responses in vivo may be related to the "cross-priming effect" whereby chimeric VP22/E7 can lead exogenous proteins to the MHC-I restricted antigen presentation pathway (26). We observed that dendritic cells pulsed with apoptotic cells transfected with SINrep5-VP22/E7 (27) or cell lysates containing VP22/E7 fusion protein (Hung, personal communication) were capable of presenting E7 antigen through the MHC class I pathway more efficiently than wild-type E7 counterparts. However, previous studies suggest that direct priming of CD8+ T cells by gene-transfected DCs is the key event in gene gun-mediated DNA immunization and cross-priming is not a major mechanism (28, 29). Thus, the extent of the involvement of cross-priming in CD8+ T cell-mediated immune responses remains unclear and requires further experiments to characterize its role in antigen presentation.

Figure 5:
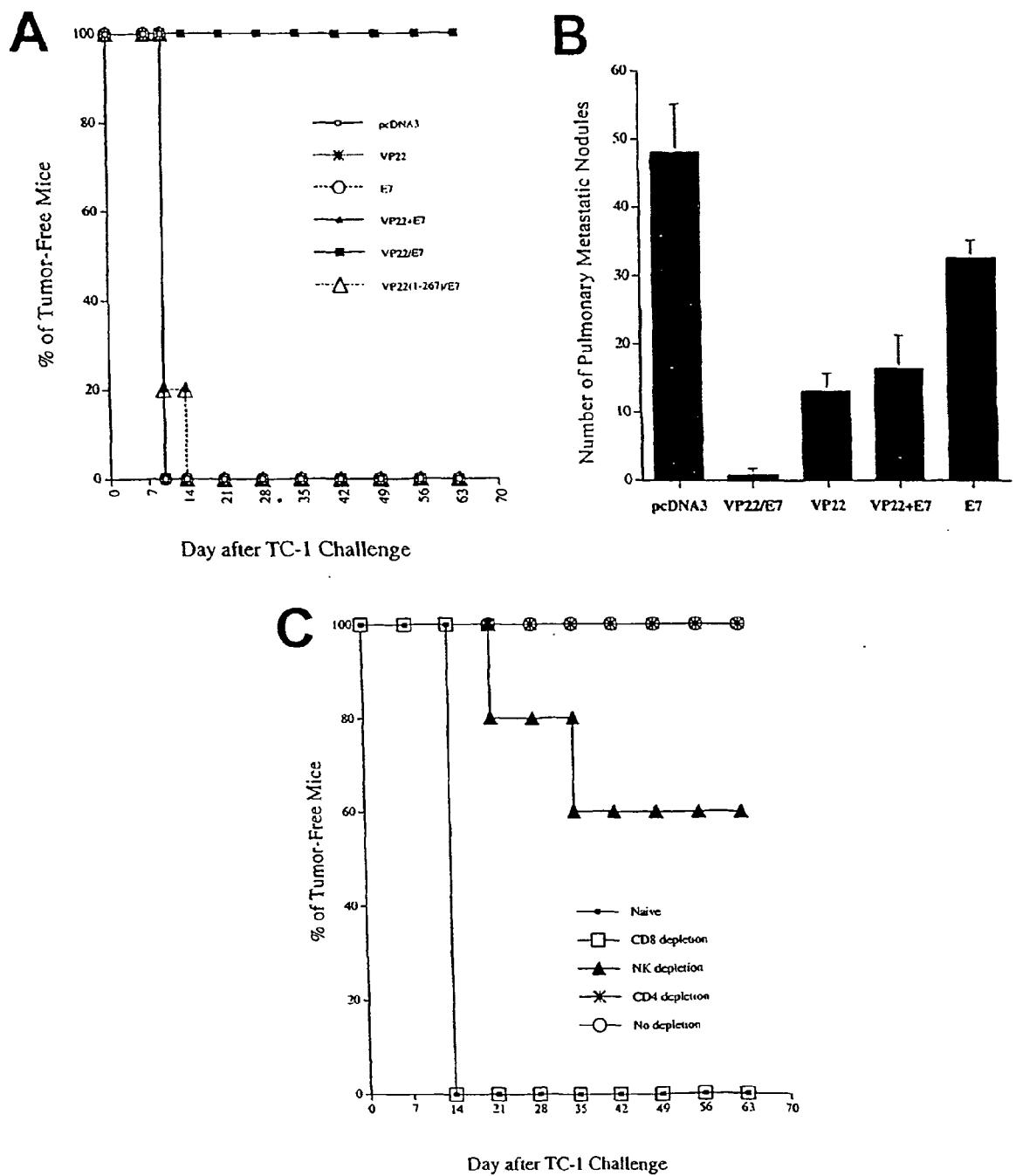
FIG. 5. In vivo tumor protection and treatment experiments against the growth of TC-1 tumors; the effect of lymphocyte subsets on tumor treatment. (A) In vivo tumor protection experiment. Mice were immunized and challenged as described in FIG. 2. The data collected from the in vivo tumor protection experiments shown here are from one representative experiment of two performed. (B) In vivo tumor treatment experiment. Mice were challenged and subsequently immunized as described in the Materials and Methods. The data obtained from these in vivo treatment experiments are from one representative experiment of two performed. (C) In vivo antibody depletion experiments to determine the effect of lymphocyte subsets on the potency of the VP22/E7 DNA vaccine. CD4, CD8 and NK1.1 depletions were initiated one week prior to tumor challenge and lasted 63 days after tumor challenge. The antibody depletion experiment data shown here are from one representative experiment of two performed.

Intercellular spreading is an important and desirable property for an antigen-specific immune response and antitumor effects. In this study, we tested a "control" construct lacking the property of intercellular spreading, VP22(1-267)/E7 DNA, and found that this vaccine did not generate significant enhancement of E7-specific CD8$^+$ T cell activity or tumor protection. However, it was not clear whether the property of intercellular spreading is alone sufficient to account for the enhancement of the T cell response. Examination of some of the molecules with trafficking properties linked to E7—TAT, MTS, or the third helix of the Antennapedia homeodomain—did not generate E7-specific CD8+ T cell immune responses comparable to those generated by VP22/E7 DNA (FIG. 5). The trafficking properties of these molecules may be different than those of VP22.

Recently, two additional examples of proteins with purported intercellular spreading properties have emerged, bovine herpesvirus VP22 (BVP22) (30) and Marek's disease virus VP22 (31, 32), both of which are VP22 homologues. Bovine herpesvirus VP22 shares about 30% amino acid identity to human herpesvirus VP22. BVP22 trafficking may be more efficient than that of human HSV VP22 after endogenous synthesis (30). Marek's disease virus VP22 also shares about 30% amino acid identity to human herpesvirus VP22 (31) and may be capable of intercellular transport after exogenous application (32). Interestingly, both molecules linked to E7 enhanced antigen processing or activate E7-specific CD8$^+$ T cells compared to wild-type E7.

The present inventors and their colleagues recently tested the VP22 strategy in a naked Sindbis RNA vector (SINrep5) (27); (see also U.S. Provisional Application Ser. No. 60/281, 004, entitled "Sindbis Virus Self Replicating RNA Vaccine Linking Antigen to HSV-1 Protein" and incorporated by reference herein). Naked DNA and Sindbis virus RNA vectors enhanced E7-specific CD8$^+$ T cell immune responses and antitumor effects, although examination of effector cells involved in the antitumor effects revealed some interesting differences between these vectors. CD8$^+$ T cells are important mediators of responses induced by of the vectors we tested, while CD4$^+$ T cells were not essential for the antitumor effect generated by either of these vaccines. Depletion of CD4$^+$ T cells after vaccination with VP22/E7 naked DNA or naked Sindbis virus RNA did not lead to significant loss in antitumor effects (27). In contrast, NK cells were essential for the antitumor effect generated by the naked Sindbis virus RNA vaccine but were not as important when using the VP22/E7 naked DNA vaccine. Thus, different types of vaccine vectors encoding the same gene(s) may activate different subsets of effector cells in the vaccinated host and have different immunological consequences and antitumor effects.

According to the present invention, the intercellular spreading strategy is useful conjunction with other strategies to further enhance vaccine potency. We previously used *Mycobacterium tuberculosis* heat shock protein 70 (HSP70) linked to E7 to significantly enhance MHC class I presentation of E7 antigen to CD8+ T cells (9). Furthermore, we developed an endosomal/lysosomal targeting strategy using E7 linked to a signal peptide (Sig) and the endosomal/lysosomal sorting signal (derived from lysosome associated membrane protein, LAMP-1) to enhance MHC class II presentation of antigen to CD4+ T cells (10). Because these two approaches may act through a different mechanism than VP22/E7, the vaccine potency of HSP70 or Sig/E7/LAMP-1 vaccines may be further enhanced if the intercellular spreading strategy is included in their design.

In summary, the results disclosed herein provide methods to enhance vaccine potency by linking VP22 to antigen, allowing for increased intercellular spreading of the antigen and enhanced stimulation of antigen-specific CD8$^+$ T cells leading to potent antitumor effects in vivo. This approach is useful for the control of cancer, infectious diseases and any other conditions where enhanced T cell reactivity, primarily CD8$^+$ T cell reactivity, is associated with prophylactic or therapeutic outcomes.

EXAMPLE VIII

Materials and Methods for MDV VP22 DNA Study

Plasmid DNA Construction

The pcDNA3 expression vector, pcDNA3-E7, pcDNA3-HVP22, pcDNA3-E7(E/B) and pcDNA3-HVP22/E7 were described in Example I. For the generation of pcDNA3-MVP22, PCR was used to amplify the MDV-1 VP22 (MVP22) DNA fragment using a DNA template containing MDV-1 UL49, (Yanagida et al., 1993, *J Gen Virol.* 74:1837-1845) and a set of primers: 5'-atctctagaatggggggattctgaaag-gcg-3' [SEQ ID NO:20] and 5'-gatgaattcttcgctatcactgctacgat-3' [SEQ ID NO:21]. The amplified product was cloned into the unique EcoRI and XbaI cloning sites of the pcDNA3.1 (−) expression vector (Invitrogen, Carlsbad, Calif.) downstream of the CMV promoter. For the generation of pcDNA3-MVP22/E7, the same PCR amplified product (MVP22) was cloned into the unique XbaI and EcoRI cloning sites of the pcDNA3-E7(E/B).

DNA Vaccination

See Example I. Mice were vaccinated via gene gun with 2 μg of MVP22, E7, MVP22 mixed with E7 (MVP22+E7), MVP22/E7, HVP22/E7 or pcDNA3 (no insert). One week later, mice were boosted using the same regimen.

Intracellular Cytokine Staining

See Example I. Splenocytes from vaccinated groups of mice were collected 8 days after last vaccination and treated as in Example I.

Enzyme Linked Immunosorbent Assay (ELISA)

The anti-HPV 16 E7 antibodies in the sera were determined by a direct ELISA as described previously (Wu et al., 1995). Briefly, wells of 96 well plates were coated with 100 μl of 10 μg/ml bacteria-derived HPV-16 E7 proteins and incubated at 4° C. overnight. The wells were then blocked with PBS containing 20% fetal bovine serum. Sera were prepared from the mice on day 14 post-immunization, serially diluted in PBS, added to the wells, and incubated on 37° C. for 2 hrs. After washing with PBS containing 0.05% Tween-20, the plate was incubated with 1/2000 dilution of a peroxidase-conjugated rabbit antimouse IgG antibody (Zymed, San Francisco, Calif.) at room temperature for 1 hour. The plate was washed 6 times, developed with 1-Step Turbo TMB-ELISA® (Pierce, Rockford, Ill.), and reactions were stopped with 1M $H_2SO_4$. The plate was read in a standard ELISA microplate reader at a wavelength of 450 nm.

In Vivo Tumor Protection

See Example I. Mice (5 per group) were vaccinated via gene gun with 2 μg of pcDNA3 (no insert), MVP22, E7, MVP22 mixed with E7 (MVP22+E7), or MVP22/E7 DNA. Thereafter, the procedures described in Example I were carried out.

In Vivo Tumor Therapy

See Example I. Three days after the tumor challenge, mice (5/group) were administered 2 μg of pcDNA3 (no insert), MVP22, E7, MVP22 mixed with E7 (MVP22+E7), or MVP22/E7 DNA via gene gun. Responses were evaluated as in Example I.

In Vivo Antibody Depletion Experiment

In vivo antibody depletions were carried out essentially as described in Example I. Mice were vaccinated with 2 μg MVP22/E7 DNA via gene gun, boosted one week later, and challenged as in Example I. Depletion was terminated on day 70 after tumor challenge.

EXAMPLE IX

Comparison of the Genomic Locus and Amino Acid Sequence of UL49 (VP22) Protein for Marek's Disease Virus Type 1 and Herpes Simplex Virus Type 1

The Marek's disease virus type 1 (MDV-1) and herpes simplex virus type 1 (HSV-1) are classified to the subfamily alphaherpesviridae. As shown in FIG. 8A, the size of the MDV-1 genome is 178 kbp (Tulman et al., 2000) and the size of the HSV-1 genome is 152 kbp (NCBI, Accession # NC_001806). Nucleotide position 111953 to 111207 in MDV-1 (Tulman et al., 2000) and nucleotide position 105486 to 106391 in HSV-1 (NCBI, Accession # NC_001806) is the coding region (UL49) for the tegument protein VP22 in the two viruses. The VP22 amino acid sequences from MDV-1 (249 amino acids in length) and HSV-1 (301 amino acids in length) are aligned in FIG. 8B. The amino acid sequences of MDV-1VP22 (MVP22), SEQ ID NO:27, and HSV-1 VP22 (HVP22) (SEQ ID NO:25) were optimally aligned with a computer program (DNAS-TAR) using the Clustal method and PAM250 residue weight table. The results revealed only approximately 20.1% homology.

EXAMPLE X

Vaccination with MVP22/E7 Fusion DNA Significantly Enhances E7-Specific $CD8^+$ T Cell-Mediated Immune Responses To determine whether vaccination of mice with the pcDNA3-MVP22/E7 DNA vaccine can enhance the number of E7-specific $CD8^+$ T cell precursors, we performed intracellular cytokine staining on splenocytes from vaccinated mice. Splenocytes from naïve or vaccinated groups of mice were incubated with the MHC class I (H-2 Db)-restricted E7 peptide (aa 49-57) for detecting E7-specific $CD8^+$ T cells. As shown in FIG. 9A, mice vaccinated with MVP22/E7 DNA exhibited a significant increase in E7-specific IFN-$\gamma^+$ $CD8^+$ T cell precursors ($139/3\times10^5$ splenocytes) compared to mice vaccinated with wild-type E7 DNA ($10/3\times10^5$ splenocytes). The physical linkage of MVP22 to E7 was important for the observed enhancement of E7-specific CD8+ T cell activity since MVP22 mixed with E7 (MVP22+E7 DNA) did not generate a significant increase in the number of $CD8^+$ T cell precursors ($20/3\times10^5$ splenocytes).

EXAMPLE X

Figure 10:
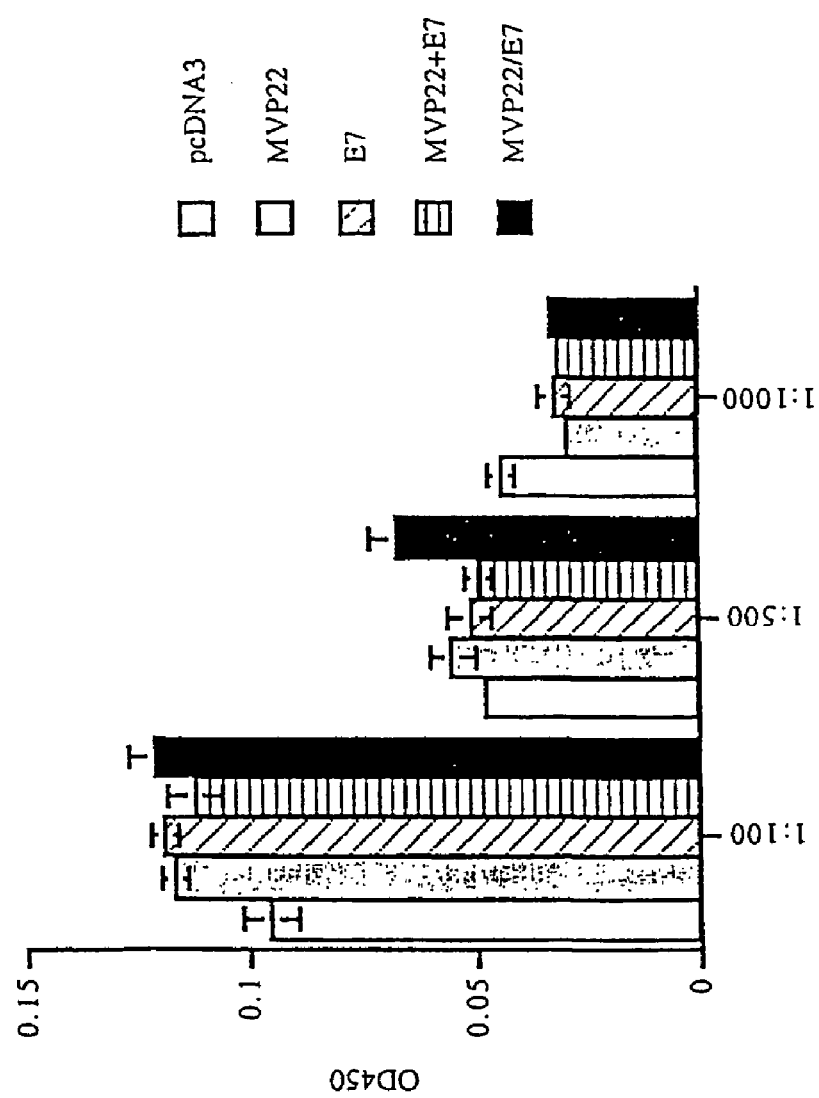

Vaccination with MVP22/E7 Fusion DNA Does Not Generate Significant E7-Specific $CD4^+$ T Cell-Mediated Responses While addition of MVP22 to E7 led to enhanced E7-specific $CD8^+$ T cell activities, we did not detect a significant difference in the number of E7-specific IFN-γ-secreting $CD4^+$ T cells (FIG. 9B) among the various vaccination groups. Using a direct enzyme linked immunosorbent assay (ELISA), we also detected no significant difference in E7-specific antibody responses in the sera of mice vaccinated with various DNA vaccines (FIG. 10).

EXAMPLE XII

Figure 11:
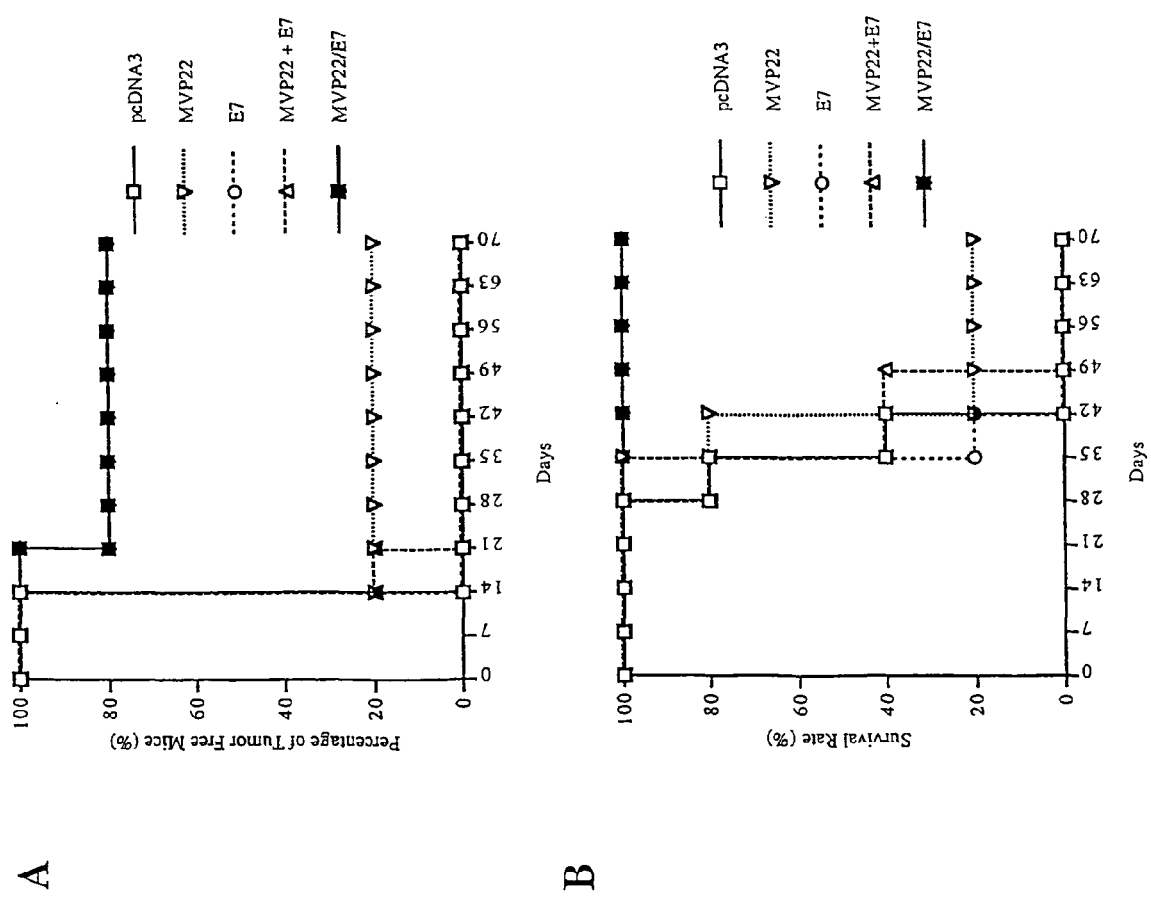
FIGS. 11A and 11B shows the protective effects of the vaccines on tumor growth and survival of mice.

Vaccination with Chimeric MVP22/E7 DNA Vaccine Enhances Protection of Mice Against the Growth of TC-1 Tumor To determine if the observed enhancement in E7-specific $CD8^+$ T cell-mediated immunity translated to a significant E7-specific antitumor effect, an in vivo tumor protection experiment was done the E7-expressing tumor TC-1 (Lin et al., 1996). As shown in FIG. 11A, 80% of mice receiving the MVP22/E7 DNA vaccine remained tumor-free 70 days after TC-1 challenge. Interestingly, 20% of mice receiving MVP22 DNA vaccine remained tumor-free 70 days after TC-1 challenge. In contrast, all of the mice receiving pcDNA3 (no insert), wild-type E7, or MVP22 mixed with E7 DNA vaccine developed tumors within 21 days after tumor challenge. We also observed that fusion of E7 to MVP22 was required for antitumor immunity, since MVP22 mixed with E7 (MVP22+E7 DNA) did not generate enhancement of tumor protection. As shown in FIG. 11B, 100% of mice receiving MVP22/E7 DNA and 20% of mice receiving MVP22 DNA survived 70 days after TC-1 challenge. In contrast, all of the mice receiving pcDNA3 (no insert), wild-type E7, or MVP22 mixed with E7 DNA vaccine did not survive 49 days after tumor challenge. These data suggested that linkage of full-length MVP22 to E7 was important for the observed enhancement of E7-specific tumor protection.

EXAMPLE XIII

Figure 12:
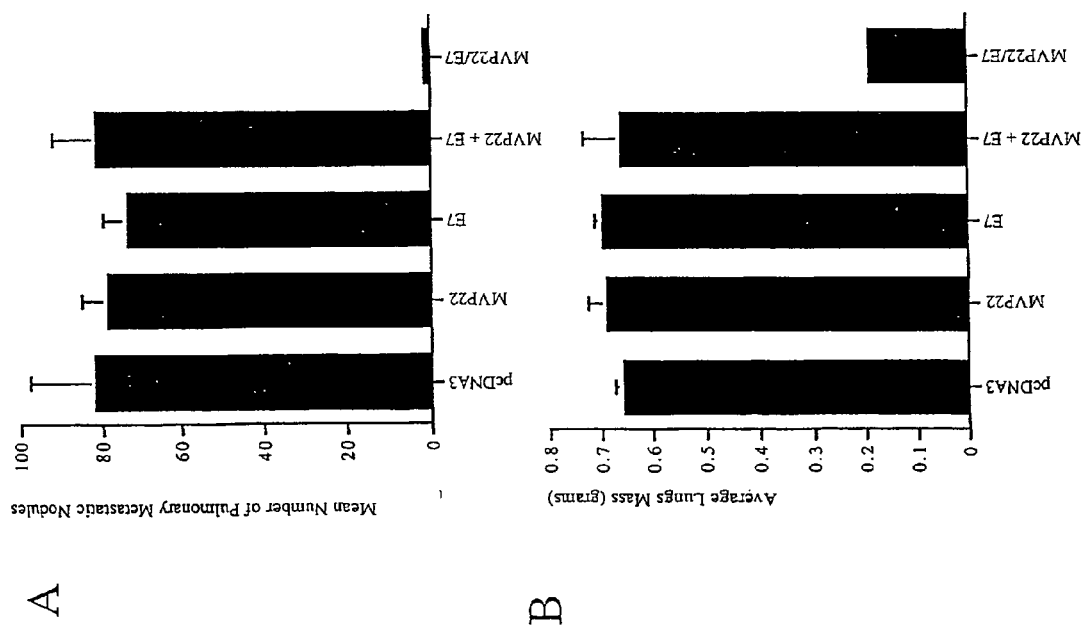
FIGS. 12A and 12B show results of tumor therapy studies.

Treatment with MVP221E7 Fusion DNA Eradicates Established E7-Expressing Tumors in the Lungs We then investigated the therapeutic potential of the chimeric MVP22/E7 DNA construct in treating TC-1 tumor metastases in the lungs. As shown in FIG. 12A, mice vaccinated with MVP22/E7 DNA exhibited the lowest mean number of pulmonary nodules (1.5±2.38) compared to mice vaccinated with wild-type E7 DNA (73.25±11.59), or MVP22 DNA (78.33±9.87). Again, as shown in FIG. 12B, mice vaccinated with MVP22/E7 DNA exhibited the lowest average lungs mass (0.1859±0.018 g) compared to mice vaccinated with wild-type E7 DNA (0.6932±0.033 g), or MVP22 DNA (0.6874±0.057 g). The results from the tumor protection and treatment experiments indicated that linkage of MVP22 to E7 dramatically enhanced antitumor effects against the growth of TC-1 tumors.

EXAMPLE XIV

Figure 13:
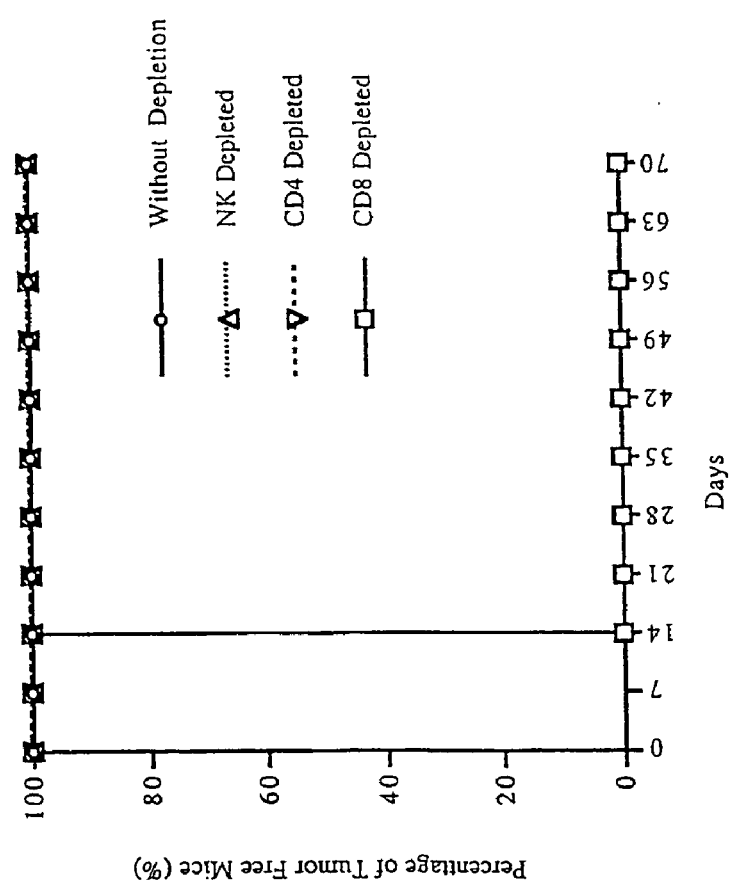
FIG. 13 shows the impact of depleting lymphocytes or NK cells on tumor growth. In vivo depletion was with mAbs. In MVP22/E7 DNA vaccinated mice, only depletion of CD8 T cells (but not of CD4 T cells or of NK cells) reversed the antitumor effect of the vaccine.

CD8$^+$ but Not CD4$^+$ T Cells or NK Cells are Important for Antitumor Effect Induced by MVP22/E7 DNA Vaccine To determine the subset of lymphocytes that are important for the antitumor effect generated by MVP22/E7 DNA vaccine, we performed in vivo antibody depletion experiments. As shown in FIG. 13, all naïve mice and MVP22/E7 DNA-vaccinated mice depleted of CD8$^+$ T cells grew tumors within 14 days after tumor challenge. In contrast, all of the mice depleted of CD4$^+$ T cells and NK cells remained tumor-free 70 days after tumor challenge. These results suggested that CD8$^+$ T cells but not CD4$^+$ T cells nor NK cells are essential for the antitumor immunity generated by the VP22/E7 DNA vaccine.

EXAMPLE XV

Figure 14:
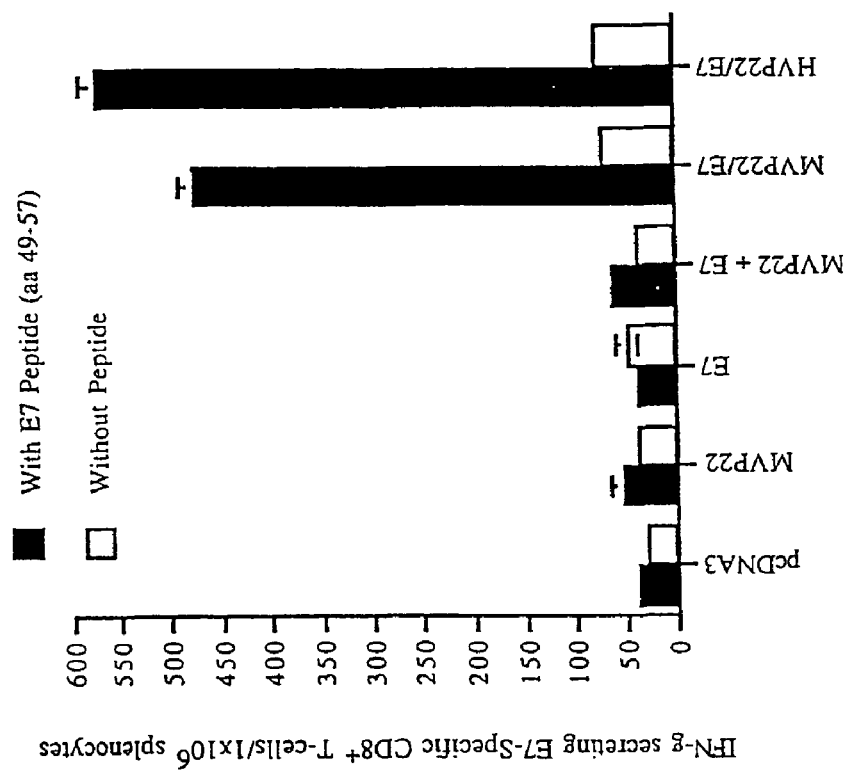
FIG. 14 shows a flow cytometric analysis of IFN-γ-secreting E7-specific $CD8^+$ T cell precursors in mice vaccinated with various recombinant DNA vaccines. The number of IFN-γ-secreting E7-specific $CD8^+$ T cell precursors induced by pcDNA3, MVP22, E7, MVP22+E7, MVP22/E7, and HVP22/E7 were determined and compared. The number of IFN-γ-producing E7-specific $CD8^+$ T cells was determined using flow cytometry in the presence (solid columns) or absence (open columns) of MHC class I restricted E7 peptide (aa 49-57). Results are expressed as mean number of IFN-γ-secreting $CD8^+$ T cells/$10^6$ splenocytes±SE. MVP22/E7 induced numbers of IFN-γ-secreting E7-specific $CD8^+$ T cell precursor comparable to those induced by HVP22/E7.

Mice Vaccinated with MVP22/E7 DNA Generated a Comparable Level of E7-Specific CD8$^+$ T Cell Precursors Compared to Mice Vaccinated with HVP22/E7 DNA Vaccine We performed intracellular cytokine staining on splenocytes from vaccinated mice, and compared the number of IFN-γ secreting E7-specific CD8$^+$ T cell precursors generated in MVP22/E7 and HVP22/E7. As shown in FIG. 14, mice vaccinated with MVP22/E7 and HVP22/E7 DNA constructs generated a significant number of E7-specific IFN-γ$^+$ CD8$^+$ T cell precursors (475 and 571/1×10$^6$, respectively) with E7 peptide stimulation as compared to pcDNA3, MVP22, E7, and MVP22+E7. Without the E7 peptide stimulation, the number of E7-specific IFN-γ-secreting CD8$^+$ T cells among each of the various vaccination groups was similar. These results indicated that MVP22/E7- and HVP22/E7-induced E7-specific CD8$^+$ T cell-mediated immune responses were similar in vaccinated mice.

Discussion of Examples VII-XIV

Despite the limited homology (or more precisely, sequence identity) between the amino acid sequence of MDV-1 UL49 (VP22) and that of HSV-1 VP22—approximately 20%—both polypeptides enhanced DNA vaccine potency when linked to a "model" antigen, E7.

It is important to note that not all molecules with "trafficking properties" have this action of enhancing vaccine potency. The present inventors found that a DNA vaccines comprising E7 DNA fused to DNA encoding sequences derived from proteins with trafficking properties (such as HIV TAT protein, the membrane-translocating sequence and the third helix of the Antennapedia homeodomain) did not generate CD8+ T cell—responses of similar potency as those induced by VP22/E7 (Hung et al., 2001a). Therefore, it was concluded that VP22 and homologues thereof have a unique property or properties that distinguish them from these other constructs.

Several factors may account for the enhanced E7-specific CD8+ T cell activity in mice administered MVP22/E7 and HVP22/E7 DNA vaccines. First, since ballistic DNA delivery can introduce DNA directly into dermal professional APCs, the intercellular spread of the MVP22 and HSV VP22 proteins within the epidermis may have increased the number of APCs that present the linked protein. Second, as described above for HSP VP22, linkage with E7 may directly enhance the presentation of E7 through MHC class I pathway to CD8$^+$ T cells and contribute to the generation of E7-specific CD8$^+$ T cell precursors in vivo (Hung et al., 2001 a). Finally, DCs pulsed with lysates of cells transfected with VP22/E7 DNA exhibited induced significantly higher specific lysis of relevant target cells by CTLs compared to CTLs stimulated by DCs pulsed with lysates of cells transfected with wild type E7 DNA (Cheng et al., 2001), This suggesting the importance of cross-priming for the enhancement of E7-specific CD8$^+$ T cell responses by this vaccine.

The influence of DNA vaccines on the biology of professional APCs at the vaccination sites is also thought to be important factor for the observed T cell activity and the antitumor effects induced by chimeric VP22/E7 DNA. Bacterial DNA is known to include immunostimulatory elements such as CpG islands (Klinman et al., 1997; Sato et al., 1996), which cause simultaneous maturation and activation of murine DCs (Sparwasser et al., 1998). Furthermore, CpG islands may elicit secretion of IL-12 and IFN-γ (Hemmi et al., 2000; Klinman et al., 1997), which are cytokines that participate in Th1-type inflammatory responses that are important for antitumor effects. However, it was not clear if the chimeric VP22/E7 DNA led to greater DC maturation or greater secretion of Th1-type cytokines compared to other DNA constructs.

The present inventors previously developed an endosomal/lysosomal targeting strategy using E7 chimerically linked to a signal peptide (Sig) and the endosomal/lysosomal sorting signal (derived from lysosome associated membrane protein, LAMP-1) to significantly enhance MHC class II presentation of antigen to CD4$^+$ T cells (Wu et al., 1995). Furthermore, several different molecules that were linked to E7, including *Mycobacterium tuberculosis* heat shock protein 70 (HSP70) (Chen et al., 2000) and domain II of *Pseudomonas* exotoxin A, significantly enhanced MHC class I presentation of the antigen to CD8+ T cells (Hung et al., 2001b). Since these types of stimulation act through intracellular pathways, unlike VP22/E7, the potency of HSP70-, ETA(dII)-, or Sig/E7/LAMP-1-containing vaccines should be even further enhanced by adding the intercellular spreading strategy into vaccine design. Thus, according to this invention, the intercellular spreading strategy is used in conjunction with other strategies to further enhance vaccine potency.

For widespread acceptance of MVP22/E7 DNA vaccines, certain safety issues must first be addressed. First, such DNA may integrate into the host genome, though it is estimated that the frequency of integration is much lower than that of spontaneous mutation and should not pose any real risk (Nichols et al., 1995). The second concerns is with the presence of HPV-16 E7 protein in host, e.g., human, cells. As an oncoprotein, E7 can disrupt cell cycle regulation by binding to tumor suppressor pRB protein in nuclei (Lukas et al., 1994), thereby leading to the accumulation of genetic aberrations and eventual malignant transformation in the host cells. The oncogenicity of E7 is eliminated by mutation of the E7 protein to destroy its ability to bind pRB (Heck et al., 1992) while still maintaining most of its antigenicity.

Another concern is the development of autoimmune disease. However, pathological examination of the vital organs in all MVP22/E7-vaccinated mice did not reveal any significant pathologic changes, indicating that MVP22/E7 can be used safely in a potent DNA.

In summary, according to the foregoing results, the fusion of MVP22 to the HPV-16 E7 gene results in a highly immunogenic composition that induces (1) powerful antigen-specific immune reactivity by CD8+ T cells and (2) meaningful antitumor effects against tumors expressing the specific antigen. Since the majority of cervical cancers express E7, MVP22/E7 chimeric DNA vaccine holds promise as a means to control of HPV-associated malignancies. However, this strategy is broadly applicable to other types of cancer. All that is needed is that the cancer be associated with a particular tumor-specific antigen, preferably one that is known.

EXAMPLE XVI

Materials and Methods for Sindbis Virus RNA Replicon Vector Plasmid DNA constructs and preparation. The Sindbis virus RNA replicon vector SINrep5 has been described (Bredenbeek, P J et al., 1993, *J. Virol.* 67:6439-6446) and was provided by Charles M. Rice of Washington University School of Medicine. The generation of pcDNA3-VP22, pcDNA3-E7 and pcDNA3-VP22/E7 was described in Example I. For the generation of SINrep5-VP22, SINrep5-E7, and SINrep5-VP22/E7, DNA fragments encoding VP22, HPV-16 E7, and chimeric VP22/E7 were isolated by digesting pcDNA3-VP22, pcDNA3-E7, and pcDNA3-VP22/E7, respectively, with XbaI and PmeI restriction enzymes. These isolated DNA fragments were further cloned into the corresponding XbaI and PmeI sites of SINrep5 to generate SINrep5-VP22, SINrep5-E7, and SINrep5-VP22/E7 constructs. The accuracy of these constructs was confirmed by DNA sequencing.

In vitro RNA preparation. The generation of RNA transcripts from SINrep5-VP22, SINrep5-E7, SINrep5-VP22/E7, and SINrep5 was performed using the protocol described by Mandl et al. (56) SpeI was used to linearize DNA templates for the synthesis of RNA replicons from SINrep5-VP22, SINrep5-E7, SINrep5-VP22/E7, and SINrep5. RNA vaccines were transcribed in vitro and capped using SP6 RNA polymerase and capping analog from the in vitro transcription kit (Life Technologies, Rockville, Md.) according to the vendor's manual. After synthesis, DNA was removed by digestion with DNase I. Synthesized RNA was then purified by precipitation. RNA concentration was determined by optical density measured at 260 nm. The integrity and quantity of RNA transcripts were further checked using denaturing gel electrophoresis (Mandl, C W et al., 1998, *Nature Med.* 4:1438-1440). The purified RNA was divided into aliquots to be used for vaccination in animals and for transfection of a BHK21 cell line. The protein expression of the transcripts was characterized by transfection of the RNA into BHK21 cells using electroporation with the Cell-Porator electroporation system (Life Technologies) according to the vendor's manual and characterized using Western blot analysis.

Cell lines. Baby hamster kidney (BHK21) cells were obtained from the American Type Culture Collection (Manassas, Va.) and grown in Glasgow minimum essential medium supplemented with 5% fetal bovine serum, 10% tryptose phosphate broth, 2 mM glutamine, and antibiotics. Cells were kept at 37° C. in a humidified 5% $CO_2$ atmosphere and were passaged every 2 days. The production and maintenance of TC-1 cells have been described previously (52).

RNA vaccination. Six to eight week-old female C57BL/6 mice from the National Cancer Institute (Frederick, Md.) were purchased and kept in the Oncology animal facility of the Johns Hopkins Hospital. All animal procedures were performed according to approved protocols and in accordance with recommendations for the proper use and care of laboratory animals. Mice were vaccinated i.m. with 1 μg of various SINrep5 RNA vaccines in the right hind leg.

CTL Assays. See Example I.

ELISA. For the determination of secreted IFNγ, splenocytes were harvested 2 weeks after vaccination and cultured with 1 μg/ml E7 peptide (aa 49-57) (MHC class I epitope) or 10 μg/ml E7 peptide (aa 30-67) (MHC class II peptide) in a total volume of 2 ml of RPMI 1640 supplemented with 10% (vol/vol) fetal bovine serum, 50 U of penicillin and streptomycin per ml, 2 mM L-glutamine, 1 mM sodium pyruvate, and 2 mM nonessential amino acids, in a 24-well tissue culture plate for 6 days. The supernatants were harvested and assayed for IFNγ using ELISA kits according to the manufacturer's protocol (Endogen, Woburn, Mass.).

HPV-16 E7-specific antibodies in sera were detected by direct ELISA as described in Example VIII.

Intracellular cytokine staining and flow cytometry analysis. See Example I.

In Vivo Tumor Protection. See, also, Example I. Mice (5/group) were immunized i.m. with 1 μg/mouse of SINrep5-VP22, SINrep5-E7, SINrep5-VP22/E7, or SINrep5 (no insert) RNA vaccine. Fourteen days after immunization, each mouse was challenged i.v. with $10^4$ TC-1 tumor cells. Three weeks later, mice were euthanatized. The lungs were weighed and pulmonary nodules were enumerated by experimenters blinded to sample identity.

In Vivo Antibody Depletion. See Example I. Each mouse (5/group) was vaccinated i.m. with 1 μg of self-replicating SINrep5-VP22/E7 RNA and challenged i.v. with $10^4$ TC-1 tumor cells 2 weeks later. Depletion treatment was terminated on day 21 after tumor challenge.

Analysis of Cell Death In Vitro. BHK21 cells ($10^7$) were transfected with 4 mg of SINrep5, SINrep5-E7, SINrep5-

VP22, or SINrep5-VP22/E7 RNA transcripts as described above. Untreated BHK21 cells or BHK21 cells electroporated without SINrep5 RNA were used as controls. Transfected BHK21 cells were collected 24 h after transfection. The percentages of apoptotic and necrotic BHK21 cells were analyzed using annexin V apoptosis detection kits (PharMingen) according to the manufacturer's protocol, followed by flow cytometry analysis.

Analysis of Cell Death In Vivo. Mice were immunized with self-replicating SIN5-VP22/E7 RNA injected i.m. into the right leg. Normal saline alone was injected i.m. into the left leg as a control. Mice were sacrificed 4 days after immunization. For the detection of apoptotic cells, a modified terminal deoxyribonucleotidyltransferase-mediated dUTP-biotin nick end labeling (TUNEL) assay was performed (47). The formalin-fixed and paraffin-embedded tissue was cut into 5 mm slices. After deparaffinization, the tissue was placed into a plastic jar containing 0.1 M citrate buffer, pH 6.0, and microwave irradiation was performed for 1 min. Then, the slides were immersed in 0.1M Tris-HCl containing 3% bovine serum albumin and 20% normal bovine serum, pH 7.5, for 30 min at room temperature. After that, the slides were rinsed twice with PBS at room temperature. The slides were then incubated with 50 ml of TUNEL reaction mixture that was provided in an in situ cell detection kit (Roche Diagnostics GmbH) for 60 min at 37° C. in a humidified chamber. Each slide was rinsed three times in PBS for 5 min. Subsequently, 0.3% $H_2O_2$ in methanol was added for 10 min at room temperature in order to eliminate endogenous peroxidase. Fifty microliters of Converter-POD (Roche Diagnostics GmbH) was added and incubated for 30 min at 37° C. in a humidified chamber. The slides were rinsed again three times in PBS at room temperature for 5 min, followed by addition of 50 ml of diaminobenzidine substrate solution and incubation for 3 min at room temperature. Finally, the slides were washed extensively in tap water and counterstained with Mayer's hematoxylin. Apoptotic index is used as a measure of the extent of apoptosis in the stained slides following inspection under a light microscope. Apoptotic index is defined as percentage of apoptotic cells and bodies per 100 cells (53).

CTL Assays Using DCs Incubated with BHK21 Cells Transfected with Various SINrep5 RNAs. CTL assays using DCs incubated with BHK21 cells transfected with various SINrep5 RNAs were performed using a protocol similar that described in Example I with modifications. See, also, Albert, L M et al., 1998, *J. Exp. Med.* 188:1359-1368; Albert, L M et al., 1998, *Nature* 392:86-89. Briefly, DCs were produced by culturing bone marrow cells in the presence of GM-CSF (Lu, Z et al., 2000, *J. Exp. Med.* 191:541-550). These DCs were characterized by flow cytometric analysis as described previously (Wang et al., 2000, supra). BHK21 cells ($10^7$) were transfected with 4 μg of various self-replicating SINrep5 RNA vectors using electroporation, and transfected BHK21 cells were collected 16 to 20 h after electroporation. The levels of E7 protein expression in B21 cells transfected with SINrep5-E7 or SINrep5-VP22/E7 RNA transcripts were determined by ELISA and standardized. Transfected BHK21 cells ($3 \times 10^5$) were then coincubated with $10^5$ bone marrow-derived DCs at 37° C. for 24 h. These prepared DCs were then used as target (T) cells, while the $D^b$-restricted E7-specific CD8+ T cells (62) served as effector (E) cells. In CTL assays, E and T ($10^4$ per well) were mixed at ratios of 1:1, 3:1, 9:1, and 27:1 in a final volume of 200 μl. After 5 h incubation at 37° C., 50 μl of the culture medium supernatant was collected to assess the amount of LDH present as described in Example I. Negative controls were: DCs incubated with untransfected BHK21 cells, transfected BHK21 cells alone, untreated DCs alone, and CD8+ T cells alone.

EXAMPLE XVII

Generation of Self-Replicating RNA Transcripts

Figure 15:
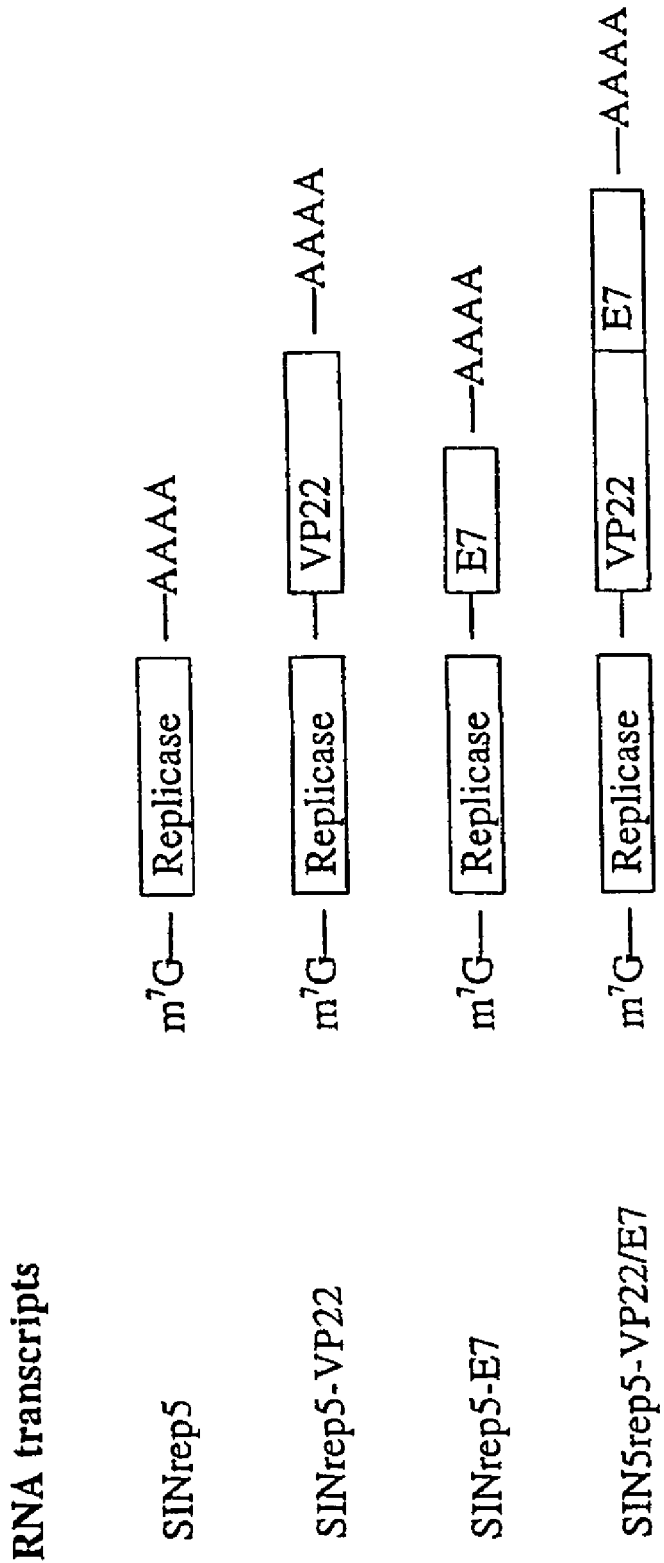
FIG. 15 is a schematic diagram of SINrep5 self-replicating RNA transcripts. A methylated m 7 G cap is located at the 59 end of the mRNA, followed by a sequence responsible for the self-replication (replicase), the gene of interest (i.e., E7, VP22, or VP22/E7), and a polyadenylated tail (AAAA).

Generation of plasmid DNA constructs and subsequent preparation of self-replicating SINrep5 RNA constructs were performed as described in Example XVI. The SINrep5 vector includes nucleic acid encoding Sindbis virus RNA replicase and the SP6 promoter (37). A schematic diagram of RNA transcripts derived from SINrep5, SINrep5-VP22, SINrep5-E7, and SINrep5-VP22/E7 DNA constructs using SP6 RNA polymerase is shown in FIG. 15. E7 expression levels in cells transfected with various E7-containing RNA constructs was characterized by Western blot analysis and ELISA. BHK21 cells transfected with self-replicating SINrep5-E7 and SINrep5-VP22/E7 expressed similar amounts of E7 protein

EXAMPLE XVIII

Figure 16:
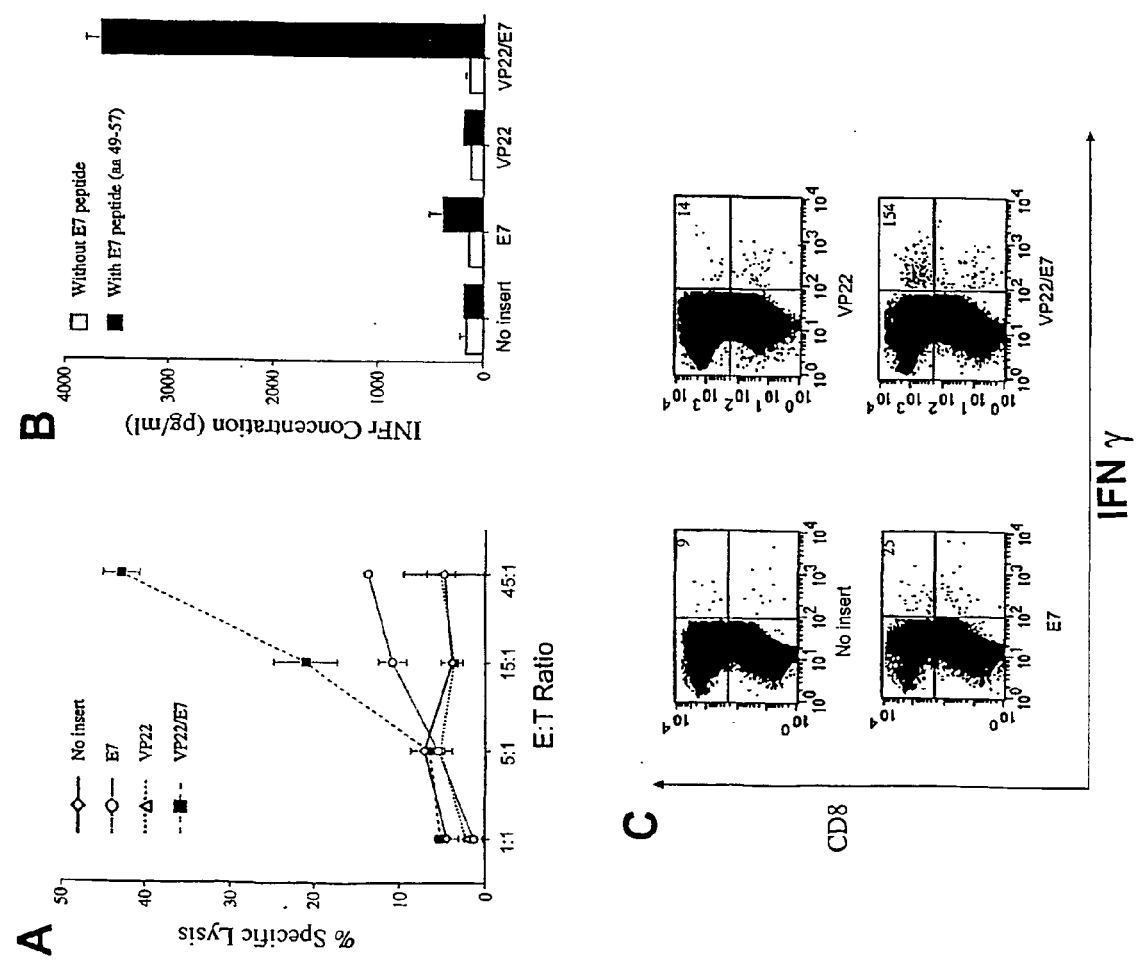
FIGS. 16A, 16B and 16C show immunologic reactivity induced by self-replicating RNA vaccines.

Vaccination with Self-Replicating SINrep5-VP22/E7 RNA Increases the Frequency of IFNγ-Secreting E7-Specific CD8 T Cells E7-specific CD8+ T cell responses to the SINrep5-VP22/E7 RNA vaccine were measured in a CTL assay. FIG. 16A shows the results of a study wherein splenocytes from mice vaccinated with various of the self-replicating SINrep5 RNA vaccines were cultured with the E7 peptide (aa 49-57) for 6 days and tested as effector cells against TC-1 tumor targets. Vaccination with SINrep5-VP22/E7 RNA generated significantly greater specific cytolysis than did that other SINrep5 RNA vaccines (P<0.001, one-way ANOVA). The lysis-inducing capacity of SINrep5-VP22/E7 RNA (42.8% lysis) was about 3-fold that of self-replicating SINrep5-E7 RNA (13.6% lysis) at an E/T ratio of 45 (P<0.001).

An indirect ELISA conducted on supernatant from cultured splenocytes was used to determine the level of secreted IFNγ in response to a pulse of MHC class I-restricted E7 peptide. The peptide was omitted in the negative control. Culture supernatants were collected and evaluated for IFNγ concentration. As shown in FIG. 16B, splenocytes from mice vaccinated with SINrep5-VP22/E7 RNA secreted the highest concentration of IFNγ (3,655 pg/ml) compared to cells from mice vaccinated with other RNA vaccines (no insert: 183 pg/ml; E7: 382 pg/ml; VP22: 190 pg/ml. Standard errors were less than 10% of the mean and statistical significance was found (P<0.001, one-way ANOVA).

To determine which subset(s) of lymphocytes secreted IFNγ, intracellular cytokine staining for IFNγ and flow cytometric analysis for CD8 was performed. Splenocytes from naive or vaccinated mice were incubated with the MHC class I (H-2 $D^b$)-restricted E7 peptide (aa 49-57) (61) to detecting E7-specific CD8+ T cells. As shown in FIG. 16C, vaccination with SINrep5-VP22/E7 RNA generated a higher number of IFNγ-secreting E7-specific CD8+ T cells than did the other vaccine preparations or controls (P<0.01, one-way ANOVA). These results indicated that fusion of VP22 to E7 significantly enhanced the activity of IFNγ-secreting E7-specific CD8+ T cells. The physical linkage of VP22 with E7 was important for this enhanced T cell reactivity because vaccination with a mixture of VP22-encodin RNA and E7-encoding RNA did not generate a significant increase of E7-specific CD8+ T cell activity (vs E7 RNA alone).

IFNγ secretion was also measured in "bulk" by indirect ELISA of the culture supernatants of splenocytes pulsed with MHC class II-restricted E7 peptide, in addition to intracellular cytokine staining (For IFNγ) and enumeration of CD4+ T cells by flow cytometry. No significant differences in IFNγ-secreting CD4+ T cells were observed between groups vaccinated with various SINrep5 RNA vaccine compositions (including controls). Determination of anti-E7 antibodies by ELISA, a measure of antigen-specific B cell reactivity, of supernatants or mouse sera did not reveal any significant differences among the groups.

EXAMPLE XIX

Figure 17:
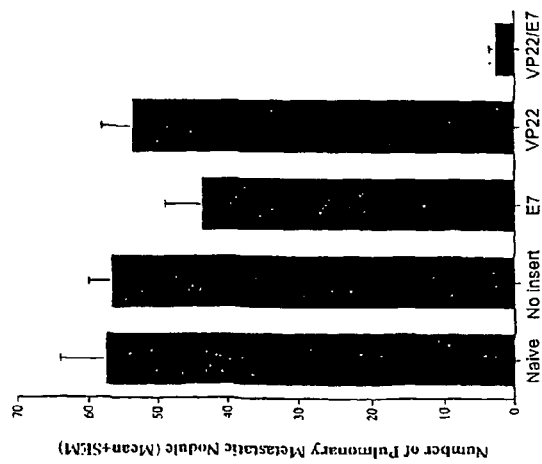
FIG. 17 shows tumor protection by various SINrep5 self-replicating RNA vaccines. Mice (5/group) were immunized i.m. with 1 μg of SINrep5-VP22, SINrep5-E7, SINrep5-VP22/E7, and SINrep5 (no insert) RNA per mouse. Two weeks after vaccination, mice were challenged with TC-1 tumor cells via i.v. injection at a dose of $10^4$ cells/mouse. Mice were monitored twice a week and sacrificed at day 21 after tumor challenge. Lungs were dissected from mice 35 days after vaccination with the various RNA vaccines. The mean number of lung tumor nodules was used as a measurement of the effectiveness of the various self-replicating RNA vaccines at controlling HPV-16 E7-expressing tumor growth. There were fewer mean pulmonary nodules in mice vaccinated with the self-replicating VP22/E7 RNA vaccine than in mice vaccinated with the other RNA vaccines (P<0.001, one-way ANOVA). SEM, standard error of the mean.
Figure 18:
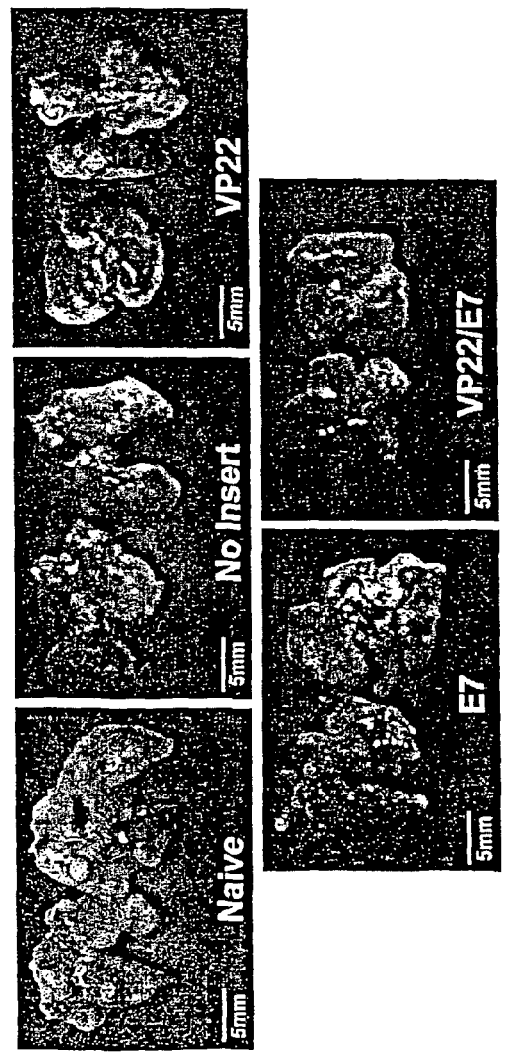
FIG. 18 shows a representative sampling of lung tumors from each vaccinated group. Multiple grossly visible lung tumors are visible in unvaccinated controls and mice vaccinated with SINrep5, SINrep5-E7, or SINrep5-VP22 RNA. Any lung tumors in the SINrep5-VP22/E7 RNA-vaccinated group were not detectable at the magnification used.

Vaccination with Self-Replicating SINrep5-VP22/E7 RNA Protects Mice Against Challenge with E7-Expressing Tumors To determine whether vaccination with the self-replicating SINrep5-VP22/E7 RNA protected mice against E7-expressing tumors, a tumor protection study in vivo was conducted. Mice were vaccinated and challenged with tumor as described in Example XVI. The number of pulmonary nodules and mean lung weight were assessed 21 days after tumor challenge. As shown in FIG. 17, fewer pulmonary nodules were found in mice vaccinated with the self-replicating VP22/E7 RNA vaccine compared to mice vaccinated with the other RNA vaccines (P<0.001, one-way ANOVA). Representative photographs of the gross appearance of lung tumors appear in FIG. 18.

The results demonstrated that the self-replicating SINrep5-VP22/E7 RNA vaccine protected mice from intravenous tumor challenge even at the low dose of 1 μg/mouse. The physical linkage of VP22 with E7 was essential for this antitumor effect because vaccination with 1 μg of a mixture of VP22 RNA and E7 RNA did not generate significant tumor protection compared to E7 RNA alone.

EXAMPLE XX

Figure 19:
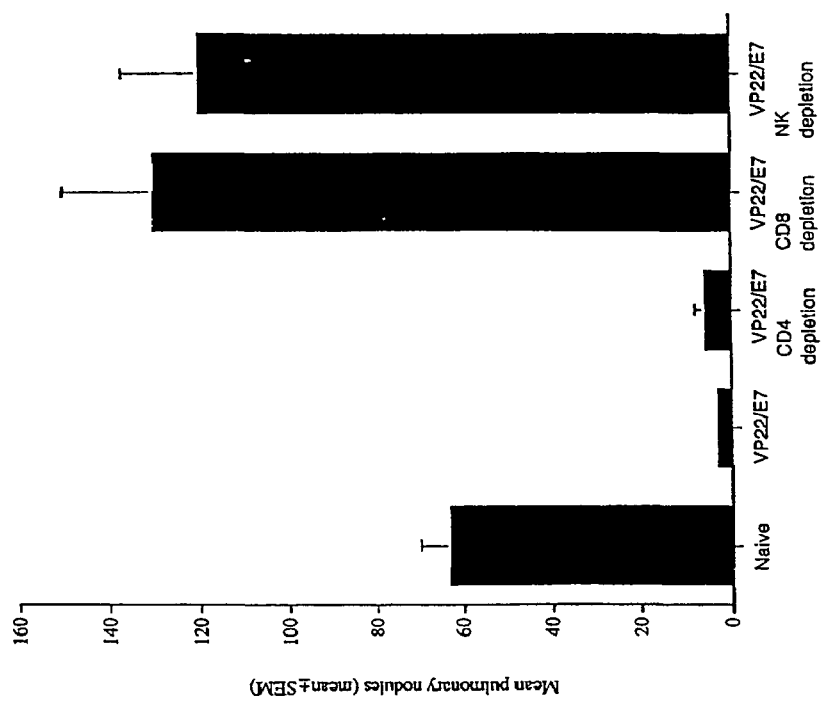
FIG. 19 shows the effect of lymphocyte subset depletions on the potency of self-replicating SINrep5-VP22/E7 RNA vaccine. Mice were immunized with 1 mg of self-replicating SINrep5-VP22/E7 RNA per mouse via i.m. injection. Two weeks after vaccination, mice were challenged with 10 4 TC-1 cells/mouse i.v. Depletions were initiated 1 week prior to tumor challenge and terminated 21 days after tumor challenge. Three weeks after tumor challenge, mice were sacrificed. Depletion of $CD8^+$ T cells and NK1.1 cells resulted in similar mean numbers of pulmonary nodules, significantly greater than those generated in the nondepleted group. The mean number of lung nodules from mice depleted of CD4+ T cells resembled results obtained from nondepleted mice. SEM, standard error of the mean.

CD8+ T Cells and NK Cells Play Important Roles in the Antitumor Effect of the SINrep5-VP22/E7 RNA Vaccine To determine the types of lymphocytes that are important for protection against E7-expressing tumor cells, we performed in vivo antibody depletion experiments. As shown in FIG. 19, the mean number of pulmonary tumor nodules from mice depleted of CD8+ T cells (130±20) and NK1.1 cells (120±17) was significantly higher than those of nondepleted (2.0±0.6) and CD4$^+$ T cell-depleted (5.7±2.2) groups (P<0.001, one-way ANOVA). In comparison, the mean number of pulmonary tumor nodules from mice depleted of CD4$^+$ T cells resembled that obtained from nondepleted mice. These antibody depletion experiments suggested that CD8+ T and NK cells are both important for the antitumor immunity generated by the SINrep5-VP22/E7 RNA vaccine.

EXAMPLE XXI

Figure 20:
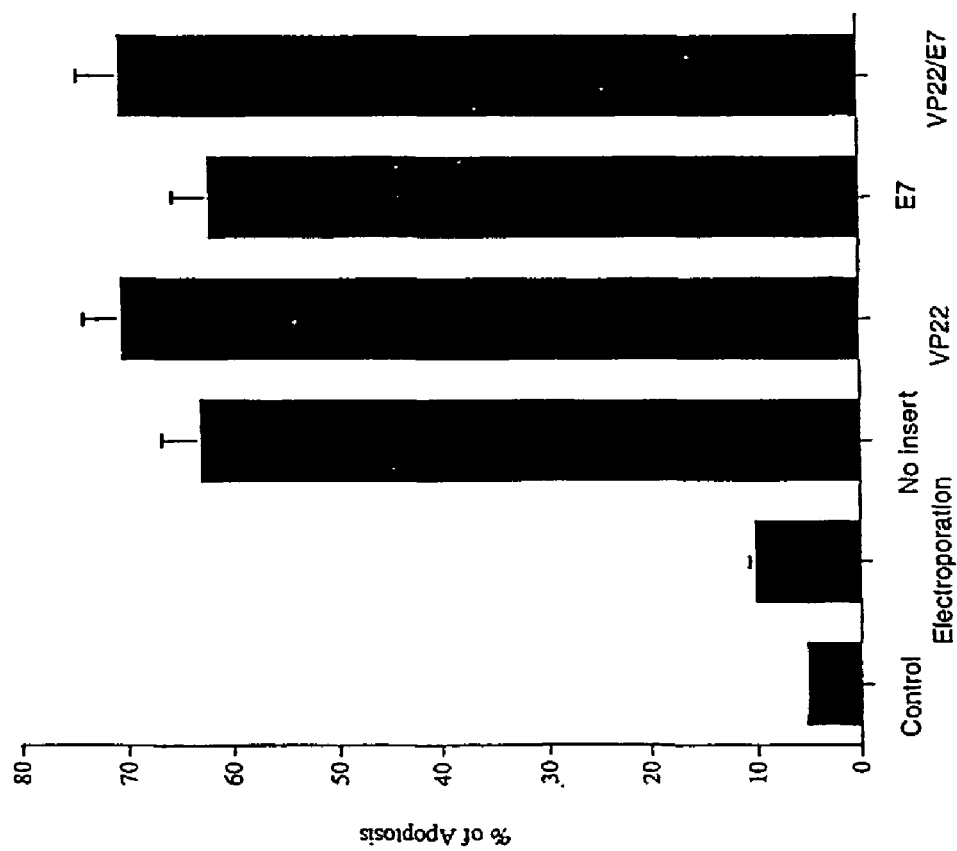
FIG. 20 shows apoptotic changes by flow cytometric analysis in BHK21 cells transfected with various SINrep5 RNA vaccines. The percentage of apoptosis in the transfected BHK21 cells was determined 24 h after transfection. Note that BHK21 cells transfected with SINrep5 RNA vaccines generated a higher percentage of apoptosis than did cells for the other two control groups. No statistical differences could be found in the apoptotic percentages generated by the various SINrep5 RNA vaccines.

Self-Replicating RNA Vaccines Induced Apoptosis in Transfected Cells and in Vaccinated Hosts RNAs transcribed in vitro from various plasmid SINrep5 RNA vaccines were transfected into BHK21 cells using electroporation. Controls were electroporated BHK21 cells not exposed to RNA and untreated BHK21 cells. The percent apoptosis observed in transfected BHK21 cells was highest at 24 h and the degree of apoptosis (up to 70%; significantly greater than controls) did not differ among BHK21 cells transfected with any of the SINrep5 RNA constructs at 24 hrs (FIG. 20).

Figure 21:
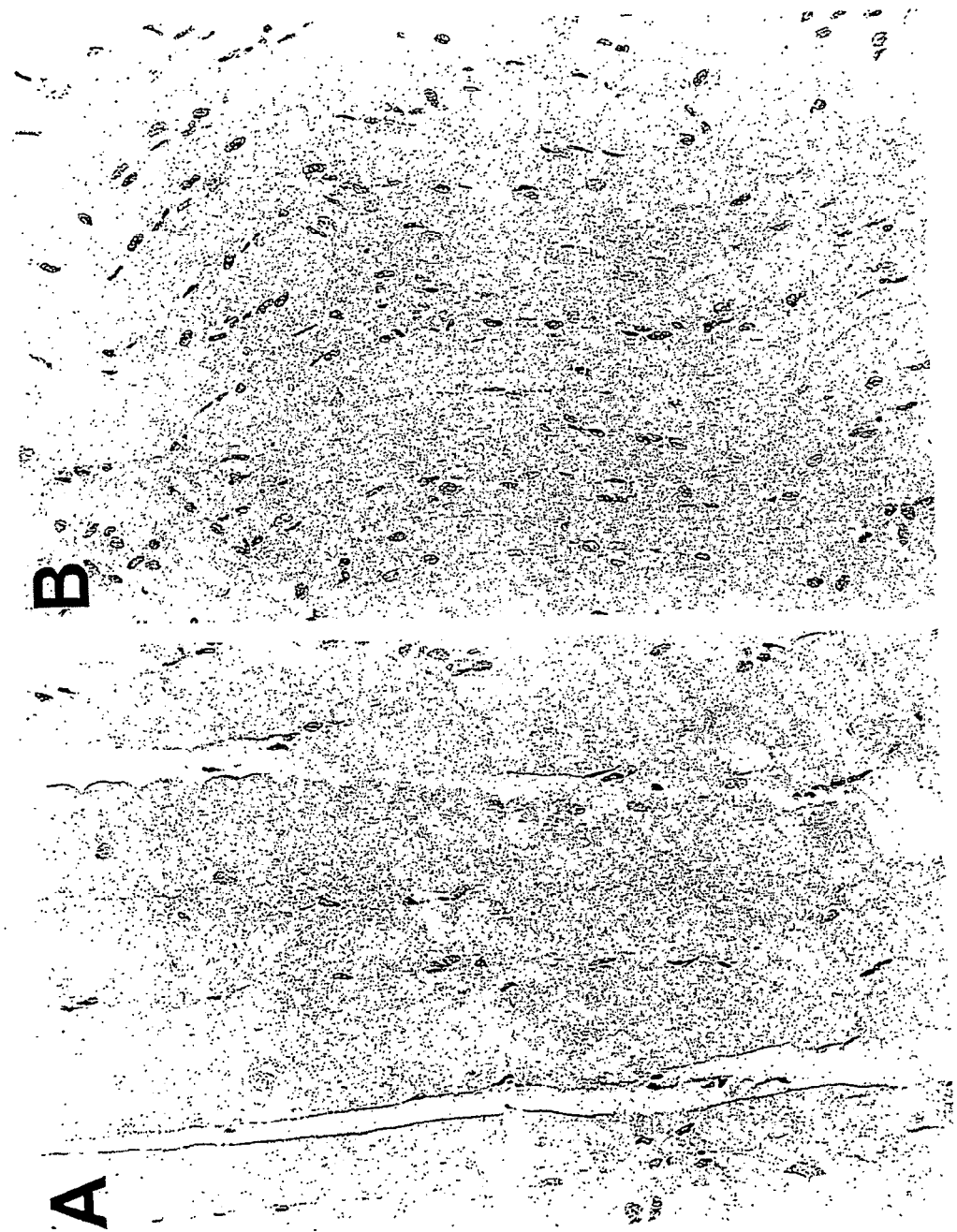
FIGS. 21A and 21B shows results of a TUNEL assay to determine apoptotic cells in the skeletal muscle of vaccinated mice.

The next step involved characterizing the extent of apoptosis induced in vivo by SINrep5 RNA. This was done by staining sections of muscle tissue at the injection sites using the TUNEL method. As shown in FIG. 21B, the SINrep5 RNA-treated group exhibited more apoptotic cells in muscle than did the saline-injected group (FIG. 21) 4 days after treatment.γγ

EXAMPLE XXII

Figure 22:
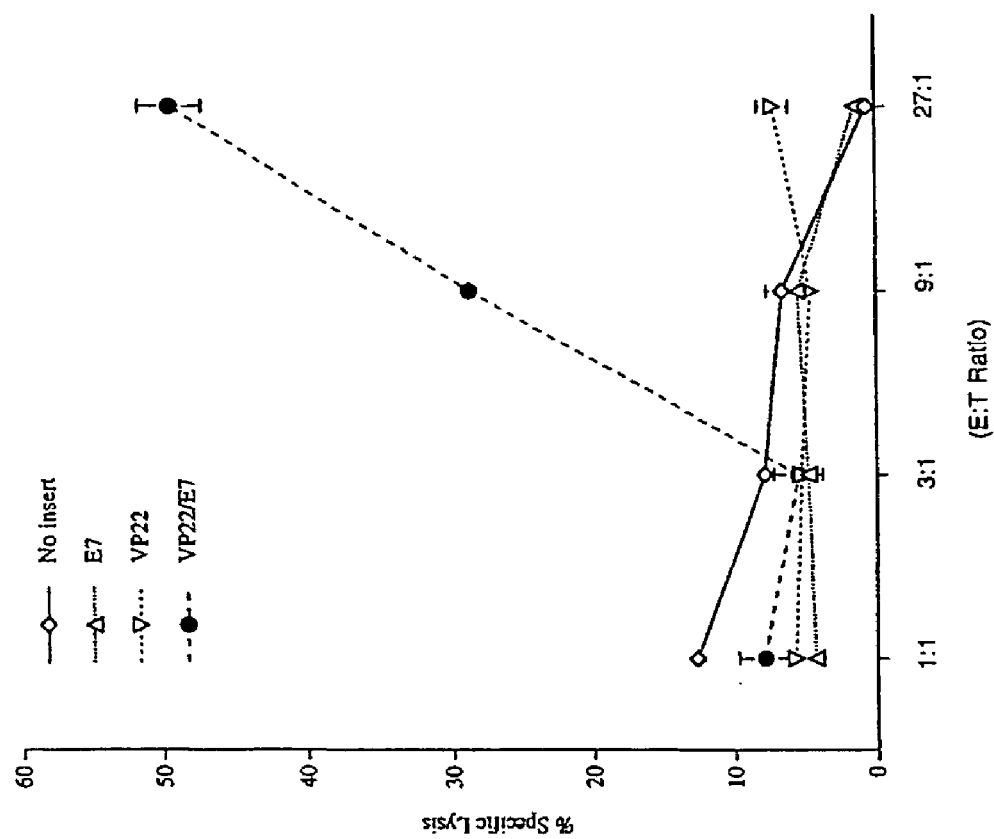
FIG. 22 shows results of CTL assays that demonstrate enhanced MHC class I presentation of E7 by bone marrow-derived DCs pulsed with apoptotic cells transfected with SINrep5-VP22/E7. BHK21 cells were electroporated with various self-replicating RNAs. The transfected BHK21 cells were cocultured with bone marrow-derived Cs. The DCs were used as target cells, and the E7-specific CD8$^+$ T cells served as effector cells. Cytolysis was determined by quantitative measurement of LDH release. The self-replicating VP22/E7 RNA vaccines generated a significantly higher percentage of specific lysis (at 9:1 and 27:1 E/T ratios) than did the other RNA vaccines (P<0.001). Results are from one experiment representative of two performed.

Enhanced Presentation of E7 Through the MHC Class I Pathway in DCs Pulsed with SINrep5-VP22/E7 RNA-Transfected Cells As discussed above, "cross priming" may be responsible for the enhanced E7-specific CD8+ T cell responses in vivo. Here that would involve presentation of E7 via the MHC class I pathway after uptake of apoptotic cells expressing various E7 constructs. A cross-priming experiment was performed to characterize MHC class I presentation of E7 in DCs pulsed with apoptotic BHK21 cells transfected with various self-replicating RNA compositions. As mentioned above the transfection efficiency of BHK21 cells is stable, and E7 expression levels among cells transfected with different E7—self-replicating RNAs were stable. Transfected BHK21 cells were coincubated with bone marrow-derived DCs, which served as target cells in CTL assays. Effector cells were tE7-specific CD8+ T cells. Assays at E/T ratios of 1:1, 3:1, 9:1, and 27:1 were performed. As shown in FIG. 22, DCs coincubated with BHK21 cells transfected with SINrep5-VP22/E7 RNA induced significantly higher specific lysis than did DCs coincubated with BHK21 cells transfected with SINrep5-E7 RNA (P<0.001).

These results suggested that DCs incubated with BHK21 cells that had been transfected with SINrep5-VP22/E7 RNA presented E7 through the MHC class I pathway more efficiently than did DCs incubated with BHK21 cells transfected with wild-type E7 RNA. Thus, the fusion of VP22 to E7 acts to stimulate E7-specific CD8+ T cell immunity via a cross-priming mechanism.

Discussion of Examples XVI-XX

The foregoing study demonstrated that linking of VP22 with E7 significantly enhanced the potency of HPV-16 E7-expressing self-replicating RNA vaccines which stimulated marked E7-specific CD8+ T cell responsiveness and, in vivo, reduced the number of lethal pulmonary E7-expressing tumors developing after i.v. challenge.

RNA vaccines possess several advantages even over efficient viral DNA vectors in gene delivery in vivo. For example, immune recognition of antigens on adenovirus or vaccinia virus vectors renders them less useful for repeat vaccination. Retrovirus vectors display low in vitro infectivity and carry potential virological risks, including helper virus replication and insertional mutagenesis. In contrast, naked RNA vaccines as described herein are relatively safe and can be administered repeatedly. Furthermore, multiple naked RNA vaccines can be administered together.

The present inventors' success in linking VP22 to a model antigen in the context of such RNA vaccines suggests that other proteins with similar trafficking properties may also enhance vaccine potency. For example, proteins such as the bovine herpesvirus 1 VP22 homolog (46) and Marek's disease virus VP22 homolog (see above; 41) enhance the intercellular spread of linked protein. Employment of such trafficking proteins in fusion with antigens in a manner similar to that described herein will enhance the potency of self-replicating RNA vaccines.

One potential mechanism for the enhanced E7-specific CD8+ T cell responses in vivo occurs when cells expressing VP22/E7 present E7 to CTLs via MHC class I. This process is known as "direct priming." However, this is believed not to be primarily responsible for the observed enhancement in the antigen-specific CD8+ T cell responses.

Intramuscular injection of DNA vaccines is known to result in DNA uptake by muscle cells at the injection sites (57). In the present study, the RNA vaccines were also tested by i.m. injection. This likely results in uptake of the RNA by muscle cells. The results exemplified above support such a conclusion (see FIGS. 21A & 21B). However, it is not possible, a priori, to exclude the possibility that cells other than muscle cells were also transduced by the injected RNA. Because they do not express costimulatory molecules that are important for efficient activation of T cells, muscle cells are not ideal professional APCs. Even if various of the SINrep5 constructs are delivered to nonmuscle cells, the self-replicating RNA eventually results in the apoptosis (of transfected cells) (44) rendering them unlikely to present antigen directly in an efficient manner.

A more likely alternative explanation for enhanced specific T cell responses following administration of chimeric SINrep5-VP22/E7 in vivo is the cross-priming effect discussed above (FIG. 22). Although the results suggests that transfection by the SINrep5-VP22/E7 vector led to apoptosis, it was not proved that DCs take up the apoptotic cells containing the VP22/E7 fusion protein or, if instead, VP22/E7 protein released after apoptosis or secreted from transduced cells is taken up. Because various SINrep5 constructs induced similar degrees of apoptosis (FIG. 20), the enhanced specific T cell reactivity was most likely due to the linkage of E7 with VP22. Thus, these results suggest that the linkage of VP22 to E7 enhanced MHC class I presentation of the linked E7 antigen through a cross-priming effect.

The present study showed that depletion of NK cells diminished the antitumor effect stimulated by the VP22/E7 RNA replicon vaccine (FIG. 19). This indicated that NK cells are necessary for at least part of the antitumor effect induced by the vaccine. However, NK cells alone could not account for the entire antitumor effect because various RNA replicon-based vaccines induced similar numbers of NK cells. The in vivo antibody depletion studies suggested that CD8+ CTLs are also important for the antitumor effects of this SINrep5-VP22/E7 RNA vaccine (FIG. 19). Thus, it was concluded that both NK cells and E7-specific CD8+ T cells were important antitumor effectors induced in response to the VP22/E7 RNA vaccine.

NK cells were not as important in the antitumor response induced by an intradermally administered naked VP22/E7 DNA vaccine. Depletion of NK1.1+cells in mice vaccinated with naked VP22/E7 DNA had only slightly effects on the antitumor response. Thus, different forms, or different routes of administration of, nucleic acid vaccines may activate different subsets of effector cells in the host and manifest different antitumor effects.

For acceptance of a VP22/E7 RNA vaccine for use in humans, certain safety considerations require review. The first issue is related to the usage of the RNA replicon. In these murine studies, increased apoptotic changes and inflammatory responses localized at the injection sites of RNA replicon-based vaccines were observed and eventually subsided (FIG. 6B). Pathological examination of vital organs in VP22/E7 RNA-vaccinated mice and did not reveal any significant changes, alleviating concern about tissue damage after administration of RNA replicon vaccines. A second risk comes from the presence of HPV-16 E7 protein in host cells as was discussed above. Use of the RNA replicon vector should reduce concerns about the oncogenicity of E7 since cells transfected with RNA replicon vaccines will eventually undergo apoptosis. In summary, fusion of a gene encoding HSV-1 VP22 to the HPV-16 E7 gene in an RNA replicon yields a vaccine composition with potent, T cell stimulatory activity which results in antitumor effects on tumors expressing the specific antigen (HPV-16 E7). Because most cervical cancers express HPV E7, the present vaccine has the potential to control HPV-associated tumors. The present strategy has applications in other cancer systems and in infectious disease. The strategy may also be exploited in other nonreplicating vector systems to improve the potency of vaccines that are otherwise limited by an inability to spread in vivo.

DOCUMENTS CITED

1. Hoffman, S. L., D. L. Doolan, M. Sedegah, R. Granizinski, H. Wang, K. Gowda, P. Hobart, M. Margalith, J. Norman, and R. C. Hedstrom. 1995. Nucleic acid malaria vaccines. Current status and potential. *Ann NY Acad Sci* 772:88-94.
2. Donnelly, J. J., J. B. Ulmer, J. W. Shiver, and M. A. Liu. 1997. DNA vaccines. *Annu Rev Immunol* 15:617-48.
3. Gurunathan, S., D. M. Klinman, and R. A. Seder. 2000. DNA vaccines: immunology, application, and optimization*. *Annu Rev Immunol* 18:927-74.
4. Elliott, G., and P. O'Hare. 1997. Intercellular trafficking and protein delivery by a herpesvirus structural protein. *Cell* 88:223-33.
5. Phelan, A., G. Elliott, and P. O'Hare. 1998. Intercellular delivery of functional p53 by the herpesvirus protein VP22. *Nat Biotechnol* 16:440-3.
6. Dilber, M. S., A. Phelan, A. Aints, A. J. Mohamed, G. Elliott, C. I. Smith, and P. O'Hare. 1999. Intercellular delivery of thymidine kinase prodrug activating enzyme by the herpes simplex virus protein, VP22. *Gene Ther* 6:12-21.
7. Chen, C. H., H. Ji, K. W. Suh, M. A. Choti, D. M. Pardoll, and T. C. Wu. 1999. Gene gun-mediated DNA vaccination induces antitumor immunity against human papillomavirus type 16 E7-expressing murine tumor metastases in the liver and lungs. *Gene Ther* 6:1972-81.
8. Ji, H., T.-L. Wang, C.-H. Chen, C.-F. Hung, S. Pai, K.-Y. Lin, R. J. Kurman, D. M. Pardoll, and T.-C. Wu. 1999. Targeting HPV-16 E7 to the endosomal/lysosomal compartment enhances the antitumor immunity of DNA vaccines against murine HPV-16 E7-expressing tumors. *Human Gene Therapy* 10:2727-2740.
9. Chen, C. H., T. L. Wang, C. F. Hung, Y. Yang, R. A. Young, D. M. Pardoll, and T. C. Wu. 2000. Enhancement of DNA vaccine potency by linkage of antigen gene to an HSP70 gene. *Cancer Res* 60:1035-42.
10. Wu, T.-C., F. G. Guarnieri, K. F. Staveley-O'Carroll, R. P. Viscidi, H. I. Levitsky, L. Hedrick, K. R. Cho, T. August, and D. M. Pardoll. 1995. Engineering an intracellular pathway for MHC class II presentation of HPV-16 E7. *Proc. Natl. Acad. Sci.* 92:11671-11675.

11. Green, M., and P. M. Loewenstein. 1988. Autonomous functional domains of chemically synthesized human immunodeficiency virus tat trans-activator protein. *Cell* 55:1179-88.
12. Schwarze, S. R., A. Ho, A. Vocero-Akbani, and S. F. Dowdy. 1999. In vivo protein transduction: delivery of a biologically active protein into the mouse. *Science* 285:1569-72.
13. Rojas, M., J. P. Donahue, Z. Tan, and Y. Z. Lin. 1998. Genetic engineering of proteins with cell membrane permeability. *Nat Biotechnol* 16:370-5.
14. Derossi, D., A. H. Joliot, G. Chassaing, and A. Prochiantz. 1994. The third helix of the Antennapedia homeodomain translocates through biological membranes. *J Biol Chem* 269:10444-50.
15. Bloom, M. B., D. Perry-Lalley, P. F. Robbins, Y. Li, M. el-Gamil, S. A. Rosenberg, and J. C. Yang. 1997. Identification of tyrosinase-related protein 2 as a tumor rejection antigen for the B 16 melanoma. *J Exp Med* 185:453-9.
16. Feltkamp, M. C., H. L. Smits, M. P. Vierboom, R. P. Minnaar, J. B. de, J. W. Drijfhout, S. J. ter, C. J. Melief, and W. M. Kast. 1993. Vaccination with cytotoxic T lymphocyte epitope-containing peptide protects against a tumor induced by human papillomavirus type 16-transformed cells. *Eur J Immunol* 23:2242-9.
17. Tindle, R. W., G. J. Fernando, J. C. Sterling, and I. H. Frazer. 1991. A "public" T-helper epitope of the E7 transforming protein of human papillomavirus 16 provides cognate help for several E7 B-cell epitopes from cervical cancer-associated human papillomavirus genotypes. *Proc Natl Acad Sci USA* 88:5887-91.
18. Lin, K.-Y., F. G. Guarnieri, K. F. Staveley-O'Carroll, H. I. Levitsky, T. August, D. M. Pardoll, and T.-C. Wu. 1996. Treatment of established tumors with a novel vaccine that enhances major histocompatibility class II presentation of tumor antigen. *Cancer Research* 56:21-26.
19. Corr, M., A. von Damm, D. J. Lee, and H. Tighe. 1999. In vivo priming by DNA injection occurs predominantly by antigen transfer. *J Immunol* 163:4721-7.
20. Wang, T.-L., M. Ling, I.-M. Shih, T. Pham, S. I. Pai, L. Lu, R. J. Kurman, D. M. Pardoll, and T.-C. Wu. 2000. Intramuscular Administration of E7-Transfected Dendritic Cells Generates the Most Potent E7-Specific Anti-Tumor Immunity. *Gene Therapy* 7:726-733.
21. Wu, T. C. 1994. Immunology of the human papilloma virus in relation to cancer. *Curr Opin Immunol* 6:746-754.
22. Schmitz, J. E., M. J. Kuroda, S. Santra, V. G. Sasseville, M. A. Simon, M. A. Lifton, P. Racz, K. Tenner-Racz, M. Dalesandro, B. J. Scallon, J. Ghrayeb, M. A. Forman, D. C. Montefiori, E. P. Rieber, N. L. Letvin, and K. A. Reimann. 1999. Control of viremia in simian immunodeficiency virus infection by CD8+ lymphocytes. *Science* 283:857-60.
23. Shen, Z., G. Reznikoff, G. Dranoff, and K. L. Rock. 1997. Cloned dendritic cells can present exogenous antigens on both MHC class I and class II molecules. *J Immunol* 158:2723-30.
24. Kim, D. T., D. J. Mitchell, D. G. Brockstedt, L. Fong, G. P. Nolan, C. G. Fathman, E. G. Engleman, and J. B. Rothbard. 1997. Introduction of soluble proteins into the MHC class I pathway by conjugation to an HIV tat peptide. *J Immunol* 159:1666-8.
25. Condon, C., S. C. Watkins, C. M. Celluzzi, K. Thompson, and L. D. Falo, Jr. 1996. DNA-based immunization by in vivo transfection of dendritic cells. *Nat Med* 2:1122-8.
26. Huang, A. Y., P. Golumbek M. Ahmadzadeh, E. Jaffee, D. Pardoll, and H. Levitsky. 1994. Role of bone marrow-derived cells in presenting MHC class I-restricted tumor antigens. *Science* 264:961-5.
27. Cheng, W.-F., C.-F. Hung, C.-Y. Chai, K.-F. Hsu, L. He, M. Ling, and T.-C. Wu. 2001. Enhancement of Sindbis Virus Self-Replicating RNA Vaccine Potency by Linkage of Herpes Simplex Virus Type 1 VP22 Protein to Antigen. *J Virol* 75:2368-2376 (2001 March).
28. Porgador, A., K. R. Irvine, A. Iwasaki, B. H. Barber, N. P. Restifo, and R. N. Germain. 1998. Predominant role for directly transfected dendritic cells in antigen presentation to CD8+ T cells after gene gun immunization. *J Exp Med* 188:1075-82.
29. Alcbari, O., N. Panjwani, S. Garcia, R. Tascon, D. Lowrie, and B. Stockinger. 1999. DNA vaccination: transfection and activation of dendritic cells as key events for immunity. *J Exp Med* 189:169-78.
30. Harms, J. S., X. Ren, S. C. Oliveira, and G. A. Splitter. 2000. Distinctions between bovine herpesvirus 1 and herpes simplex virus type 1 VP22 tegument protein subcellular associations. *J Virol* 74:3301-12.
31. Koptidesova, D., J. Kopacek, V. Zelnik, N. L. Ross, S. Pastorekova, and J. Pastorek. 1995. Identification and characterization of a cDNA clone derived from the Marek's disease tumour cell line RPL1 encoding a homologue of alpha-transinducing factor (VP16) of HSV-1. *Arch Virol* 140:355-62.
32. Dorange, F., S. El Mehdaoui, C. Pichon, P. Coursaget, and J. F. Vautherot. 2000. Marek's disease virus (MDV) homologues of herpes simplex virus type 1 UL49 (VP22) and UL48 (VP16) genes: high-level expression and characterization of MDV-1 VP22 and VP 16. *J Gen Virol* 81 Pt 9:2219-30.
33. Albert, L. M., S. F. Pearce, L. M. Francisco, B. Sauter, P. Roy, R. L. Silverstein, and N. Bhardwaj. 1998. Immature dendritic cells phagocytose apoptotic cells via alphavbeta5 and CD36, and cross-present antigens to cytotoxic T lymphocytes. J. Exp. Med. 188:1359-1368.
34. Albert, L. M., B. Sauter, and N. Bhardwaj. 1998. Dendritic cells acquire antigen from apoptotic cells and induce class I-restricted CTLs. Nature 392:86-89.
35. Berglund, P., M. Quesada-Rolander, P. Putkonen, G. Biberfeld, R. Thor-stensson, and P. Liljestrom. 1997. Outcome of immunization of cynomolgus monkeys with recombinant Semlili Forest virus encoding human immuno-deficiency virus type 1 envelope protein and challenge with a high dose of SHIV-4 virus. AIDS Res. Hum. Retrovir. 13:1487-1495.
36. Berglund, P., C. Smerdou, M. N. Fleeton, I. Tubulekas, and P. Liljestrom. 1998. Enhancing immune responses using suicidal DNA vaccines. Nat. Bio-technol. 16:562-565.
37. Bredenbeek, P. J., I. Frolov, C. M. Rice, and S. Schlesinger. 1993. Sindbis virus expression vectors: packaging of RNA replicons by using defective helper RNAs. J. Virol. 67:6439-6446.
38. Chen, C.-H., T.-L. Wang, C.-F. Hung, Y. Yang, R. A. Young, D. M. Pardoll, and T.-C. Wu. 2000. Enhancement of DNA vaccine potency by linkage of antigen gene to an HSP70 gene. Cancer Res. 60:1035-1042.
39. Dialynas, D. P., Z. S. Quan, K. A. Wall, A. Pierres, J. Quintans, M. R. Loken, M. Pierres, and F. W. Fitch. 1983. Characterization of the murine T cell surface molecule, designated L3T4, identified by monoclonal antibody GK1.5: similarity of L3T4 to the human Leu-3/T4 molecule. J. Immunol. 131:2445-2451.

40. Dilber, S. M., A. Phelan, A. Aints, A. J. Mohamed, G. Elliott, C. I. Smith, and P. O'Hare. 1999. Intercellular delivery of thymidine kinase prodrug activat-ing enzyme by the herpes simplex virus protein, VP22. Gene Ther. 6:12-21.

41. Dorange, F., S. El Mehdaoui, C. Pichon, P. Coursaget, and J. F. Vautherot. 2000. Marek's disease virus (MDV) homologues of herpes simplex virus type 1 UL49 (VP22) and UL48 (VP 16) genes: high-level expression and charac-terization of MDV-1 VP22 and VP16. J. Gen. Virol. 81(Part 9):2219-2230.

42. Elliott, G., and P. O'Hare. 1997. Intercellular trafficking and protein delivery by a herpesvirus structural protein. Cell 88:223-233.

43. Feltlcamp, C. M., H. L. Smits, M. P. Vierboom, R. P. Minnaar, B. M. de Jongh, J. W. Drijfhout, J. ter Schegget, C. J. Melief, and W. M. Kast. 1993. Vaccination with cytotoxic T lymphocyte epitope-containing peptide protects against a tumor induced by human papillomavirus type 16-transformed cells. Eur. J. Immunol. 23:2242-2249.

44. Frolov, I., and S. Schlesinger. 1996. Translation of Sindbis virus mRNA: analysis of sequences downstream of the initiating AUG codon that enhance translation. J. Virol. 70:1182-1190.

45. Hariharan, J. M., D. A. Driver, K. Townsend, D. Brumm, J. M. Polo, B. A. Belli, D. J. Catton, D. Hsu, D. Mittelstaedt, J. E. McCormack, L. Karavodin, T. W. Dubensky, Jr., S. M. Chang, and T. A. Banks. 1998. DNA immunization against herpes simplex virus: enhanced efficacy using a Sindbis virus-based vector. J. Virol. 72:950-958.

46. Harms, J. S., X. Ren, S. C. Oliveira, and G. A. Splitter. 2000. Distinctions between bovine herpesvirus 1 and herpes simplex virus type 1 VP22 tegu-ment protein subcellular associations. J. Virol. 74:3301-3312.

47. Haussler, O., J. I. Epstein, M. B. Amin, P. U. Heitz, and S. Hailemariam. 1999. Cell proliferation, apoptosis, oncogene, and tumor suppressor gene status in adenosis with comparison to benign prostatic hyperplasia, prostatic intraepithelial neoplasia, and cancer. Hum. Pathol. 30:1077-1086.

48. Huang, A. Y., P. Golumbek, M. Ahmadzadeh, E. Jaffee, D. Pardoll, and H. Levitsky. 1994. Role of bone marrow-derived cells in presenting MHC class I-restricted tumor antigens. Science 264:961-965.

49. Koo, G. C., F. J. Dumont, M. Tutt, J. Hackett, Jr., and V. Kumar. 1986. The NK-1.1(2) mouse: a model to study differentiation of murine NK cells. J. Immunol. 137:3742-3747.

50. Leitner, W. W., H. Ying, D. A. Driver, T. W. Dubensky, and N. P. Restifo. 2000. Enhancement of tumor-specific immune response with plasmid DNA replicon vectors. Cancer Res. 60:51-55.

51. Leitner, W. W., H. Ying, and N. P. Restifo. 1999. DNA and RNA-based vaccines: principles, progress and prospects. Vaccine 18:765-777.

52. Lin, K.-Y., F. G. Guarnieri, K. F. Staveley-O'Carroll, H. I. Levitsky, T. August, D. M. Pardoll, and T.-C. Wu. 1996. Treatment of established tumors with a novel vaccine that enhances major histocompatibility class II presen-tation of tumor antigen. Cancer Res. 56:21-26.

53. Lipponen, P. K., and S. Aaltomaa. 1994. Apoptosis in bladder cancer as related to standard prognostic factors and prognosis. J. Pathol. 173:333-339.

54. Lu, Z., L. Yuan, X. Zhou, E. Sotomayor, H. I. Levitsky, and D. M. Pardoll. 2000. CD40-independent pathways of T cell help for priming of CD8(1) cytotoxic T lymphocytes. J. Exp. Med. 191:541-550.

55. Lukas, J., H. Muller, J. Bartkova, D. Spitkovsky, A. A. Kjerulff, D. P. Jansen, M. Strauss, and J. Bartek. 1994. DNA tumor virus oncoproteins and reti-noblastoma gene mutations share the ability to relieve the cell's requirement for cyclin D1 function in G1. J. Cell Biol. 125:625-638.

56. Mandl, C. W., J. H. Aberle, S. W. Aberle, H. Holzmann, S. L. Allison, and F. X. Heinz. 1998. In vitro-synthesized infectious RNA as an attenuated live vaccine in a flavivirus model. Nat. Med. 4:1438-1440.

57. Pardoll, D. M., and A. M. Beckerleg. 1995. Exposing the immunology of naked DNA vaccines. Immunity 3:165-169.

58. Phelan, A., G. Elliott, and P. O'Hare. 1998. Intercellular delivery of func-tional p53 by the herpesvirus protein VP22. Nat. Bioteclmol. 16:440-443.

59. Pushko, P., M. Parker, G. V. Ludwig, N. L. Davis, R. E. Johnston, and J. F. Smith. 1997. Replicon-helper systems from attenuated Venezuelan equine encephalitis virus: expression of heterologous genes in vitro and immunization against heterologous pathogens in vivo. Virology 239:389-401.

60. Sarmiento, M., A. L. Glasebrook, and F. W. Fitch. 1980. IgG or IgM mono-clonal antibodies reactive with different determinants on the molecular com-plex bearing Lyt 2 antigen block T cell-mediated cytolysis in the absence of complement. J. Immunol. 125:2665-2672.

61. Tindle, R. W., G. J. Fernando, J. C. Sterling, and I. H. Frazer. 1991. A "public" T-helper epitope of the E7 transforming protein of human papil-lomavirus 16 provides cognate help for several E7 B-cell epitopes from cervical cancer-associated human papillomavirus genotypes. Proc. Natl. Acad. Sci. USA 88:5887-5891.

62. Wang, T.-L., L. Ling, I.-M. Shih, T. Pham, S. L. Pai, L. Lu, R. J. Kurman, D. M. Pardoll, and T.-C. Wu. 2000. Intramuscular administration of E7-transfected dendritic cells generates the most potent E7-specific anti-tumor immunity. Gene Ther. 7:726-733.

63. Wu, T.-C., F. G. Guarnieri, K. F. Staveley-O'CalToll, R. P. Viscidi, H. I. Levitsky, L. Hedrick, K. R. Cho, T. August, and D. M. Pardoll. 1995. Engi-neering an intracellular pathway for MHC class II presentation of HPV-16 E7. Proc. Natl. Acad. Sci. USA 92:11671-11675.

64. Wu, T. C., A. Y. Huang, E. M. Jaffee, H. I. Levitsky, and D. M. Pardoll. 1995. A reassessment of the role of B7-1 expression in tumor rejection. J. Exp. Med. 182:1415-1421.

65. Ying, H., T. Z. Zaks, R. F. Wang, K. R. Irvine, U.S. Kammula, F. M. Marincola, W. W. Leitner, and N. P. Restifo. 1999. Cancer therapy using a self-replicating RNA vaccine. Nat. Med. 5:823-827.

Chen, C. H., Wang, T. L., Hung, C. F., Yang, Y., Young, R. A., Pardoll, D. M. and Wu, T. C. (2000). Enhancement of DNA vaccine potency by linkage of antigen gene to an HSP70 gene. Cancer Res. 60, 1035-1042.

Cheng, W.-F., Hung, C.-F., Chai, C.-Y., Hsu, K.-F., He, L., Ling, M. and Wu, T.-C. (2001). Enhancement of Sindbis Virus Self-Replicating RNA Vaccine Potency by Linkage of Herpes Simplex Virus Type 1 VP22 Protein to Antigen. J Virol (in press).

Condon, C., Watkins, S. C., Celluzzi, C. M., Thompson, K. and Falo, L. D., Jr. (1996). DNA-based immunization by in vivo transfection of dendritic cells. Nat Med. 2, 1122-1128.d Dialynas, D. P., Quan, Z. S., Wall, K. A., Pierres, A., Quintans, J., Loken, M. R., Pierres, M. and Fitch, F. W. (1983). Characterization of the murine T cell surface molecule, designated L3T4, identified by monoclonal antibody GK1.5: similarity of L3T4 to the human Leu-3/T4 molecule. J. Immunol. 131, 2445.

Donnelly, J. J., Ulmer, J. B., Shiver, J. W. and Liu, M. A. (1997). DNA vaccines. Annu Rev Immunol. 15, 617-648.

Dorange, F., El Mehdaoui, S., Pichon, C., Coursaget, P. and Vautherot, J. F. (2000). Marek's disease virus (MDV) homologues of herpes simplex virus type 1 UL49 (VP22) and UL48 (VP16) genes: high-level expression and characterization of MDV-1 VP22 and VP16. J Gen Virol. 81 Pt 9, 2219-2230.

Elliott, G. and O'Hare, P. (1997). Intercellular trafficking and protein delivery by a herpesvirus structural protein. Cell. 88, 223-233.

Feltkamp, M. C., Smits, H. L., Vierboom, M. P., Minnaar, R. P., de, J. B., Drijfhout, J. W., ter, S. J., Melief, C. J. and Kast, W. M. (1993). Vaccination with cytotoxic T lymphocyte epitope-containing peptide protects against a tumor induced by human papillomavirus type 16-transformed cells. Eur J. Immunol. 23, 2242-2249.

Heck, D. V., Yee, C. L., Howley, P. M. and Munger, K. (1992). Efficiency of binding the retinoblastoma protein correlates with the transforming capacity of the E7 oncoproteins of the human papillomaviruses. Proc Natl Acad Sci USA. 89, 4442-4446.

Hemmi, H., Takeuchi, O., Kawai, T., Kaisho, T., Sato, S., Sanjo, H., Matsumoto, M., Hoshino, K., Wagner, H., Takeda, K. and Akira, S. (2000). A Toll-like receptor recognizes bacterial DNA. Nature. 408, 740-745.

Hung, C.-F., Cheng, W.-F., Chai, C.-Y., Hsu, K.-F., He, L., Ling, M. and Wu, T.-C. (2001a). Improving vaccine potency through intercellular spreading and enhanced MHC class I presentation of antigen. J Immunol 166: 5733-5740.

Hung, C.-F., Cheng, W.-F., Hsu, K.-F., Chai, C.-Y., He, L., Ling, M. and Wu, T.-C. (2001b). Cancer immunotherapy using a DNA vaccine encoding the translocation domain of a bacterial toxin linked to a tumor antigen. Cancer Research. 61, 3698-3703.

Ji, H., Wang, T.-L., Chen, C.-H., Hung, C.-F., Pai, S., Lin, K.-Y., Kurman, R. J., Pardoll, D. M. and Wu, T.-C (1999). Targeting HPV-16 E7 to the endosomal/lysosomal compartment enhances the antitumor immunity of DNA vaccines against murine HPV-16 E7-expressing tumors. Human Gene Therapy. 10, 2727-2740.

Klinman, D. M., Yamshchikov, G. and Ishigatsubo, Y. (1997). Contribution of CpG motifs to the immunogenicity of DNA vaccines. J. Immunol. 158, 3635-3639.

Koo, G. C., Dumont, F. J., Tutt, M., Hackett, J., Jr. and Kurnar, V. (1986). The NK-1.1(−) mouse: a model to study differentiation of murine NK cells. J. Immunol. 137, 3742.

Koptidesova, D., Kopacek, J., Zelnik, V., Ross, N. L., Pastorekova, S. and Pastorek, J. (1995). Identification and characterization of a cDNA clone derived from the Marek's disease tumour cell line RPL1 encoding a homologue of alpha-transinducing factor (VP16) of HSV-1. Arch Virol. 140, 355-362.

Lin, K.-Y., Guarnieri, F. G., Staveley-O'Carroll, K. F., Levitsky, H. I., August, T., Pardoll., D. M. and Wu, T.-C (1996). Treatment of established tumors with a novel vaccine that enhances major histocompatibility class II presentation of tumor antigen. Cancer Research. 56, 21-26.

Lukas, J., Muller, H., Bartkova, J., Spitkovsky, D., Kjerulff, A. A., Jansen, D. P., Strauss, M. and Bartek J. (1994). DNA tumor virus oncoproteins and retinoblastoma gene mutations share the ability to relieve the cell's requirement for cyclin D1 function in G1. J. Cell Biol. 125, 625-638.

Nichols, W. W., Ledwith, B. J., Manam, S. V. and Troilo, P. J. (1995). Potential DNA vaccine integration into host cell genome. Annals of NY Academy of Science. 772, 30-39.

Pardoll, D. M. and Beckerleg, A. M. (1995). Exposing the immunology of naked DNA vaccines. Immunity. 3 165-169.

Robinson, H. L. and Torres, C. A. (1997). DNA vaccines. Semin Immunol. 9, 271-283.

Sarmiento, M., Glasebrook A. L. and Fitch, F. W. (1980). IgG or IgM monoclonal antibodies reactive with different determinants on the molecular complex bearing Lyt 2 antigen block T cell-mediated cytolysis in the absence of complement. J. Immunol. 125, 2665-2672.

Sato, Y., Roman, M., Tighe, H., Lee, D., Corr, M., Nguyen, M. D., Silverman, G. J., Lotz, M., Carson, D. A. and Raz, E. (1996). Immunostimulatory DNA sequences necessary for effective intradermal gene immunization. Science. 273, 352-354.

Sparwasser, T., Koch, E. S., Vabulas, R. M., Heeg, K., Lipford, G. B., Ellwart, J. W. and Wagner, H. (1998). Bacterial DNA and immunostimulatory CpG oligonucleotides trigger maturation and activation of murine dendritic cells. Eur J Immunol. 28, 2045-2054.

Tindle, R. W., Fernando, G. J., Sterling, J. C. and Frazer, I. H. (1991). A "public" T-helper epitope of the E7 transforming protein of human papillomavirus 16 provides cognate help for several E7 B-cell epitopes from cervical cancer-associated human papillomavirus genotypes. Proc Natl Acad Sci USA. 88, 5887-5891.

Tulman, E. R., Afonso, C. L., Lu, Z., Zsak, L., Rock, D. L. and Kutish, G. F. (2000). The genome of a very virulent Marek's disease virus. J. Virol. 74, 7980-7988.

Wu, T.-C., Guarnieri, F. G., Staveley-O'Carroll, K. F., Viscidi, R. P., Levitsky, H. I., Hedrick, L., Cho, K. R., August, T. and Pardoll, D. M. (1995). Engineering an intracellular pathway for MHC class II presentation of HPV-16 E7. Proc. Natl. Acad. Sci. 92, 11671-11675.

Yanagida, N., Yoshida, S., Nazerian, K. and Lee, L. F. (1993). Nucleotide and predicted amino acid sequences of Marek's disease virus homologues of herpes simplex virus major tegument proteins. J Gen Virol. 74, 1837-1845.

The references cited above are all incorporated by reference herein, whether specifically incorporated or not.

Citation of the documents herein is not intended as an admission that any of them is pertinent prior art. All statements as to the date or representation as to the contents of these documents is based on the information available to the applicant and does not constitute any admission as to the correctness of the dates or contents of these documents.

What is claimed is:

1. A recombinant nucleic acid molecule encoding a fusion or chimeric polypeptide, which molecule comprises:

(a) a first nucleic acid sequence encoding a first polypeptide that comprises at least one Marek's Disease Virus (MDV) VP22 protein comprising SEQ ID NO: 28, or a homologue of the polypeptide comprising an amino acid sequence that is at least about 90% identical to SEQ ID NO: 28; and (b) a second nucleic acid sequence that is linked in frame to said first nucleic acid sequence and that encodes an antigenic polypeptide or peptide from Human Papillomavirus (HPV), wherein the first and the second nucleic acid sequences are in a self-replicating RNA replicon.

2. The nucleic acid molecule of claim 1, wherein the antigenic polypeptide comprises an epitope that binds to, and is presented on the cell surface by, an MHC class I protein.

3. The nucleic acid molecule of claim 2, wherein said epitope is between about 8 and about 11 amino acid residues in length.

4. The nucleic acid molecule of claim 1, further comprising a linker fused in frame to the first and the second nucleic acid sequences.

5. The nucleic acid molecule of claim 1, wherein the antigen is the E7 polytide of HPV-16 or an antigenic fragment therof.

6. The nucleic acid molecule of claim 1, wherein the self-replicating replicon is a Sindbis virus RNA replicon.

7. The nucleic acid molecule of claim 4, wherein the Sindbis virus RNA replicon is SINrep5.

8. The nucleic acid molecule of claim 5, wherein the E7 polypeptide comprises SEQ ID NO: 27.

9. The nucleic acid of claim 1, which is DNA coated on a gold particle.

* * * * *

SEQUENCE LISTING

<160> NUMBER OF SEQ ID NOS: 29

<210> SEQ ID NO 1
<211> LENGTH: 24
<212> TYPE: DNA
<213> ORGANISM: Artificial sequence
<220> FEATURE:
<223> OTHER INFORMATION: Primer

<400> SEQUENCE: 1
ggggaattca tgagataca ccta                                    24

<210> SEQ ID NO 2
<211> LENGTH: 23
<212> TYPE: DNA
<213> ORGANISM: Artificial sequence
<220> FEATURE:
<223> OTHER INFORMATION: Primer

<400> SEQUENCE: 2
ggtggatcct tgagaacaga tgg                                    23

<210> SEQ ID NO 3
<211> LENGTH: 29
<212> TYPE: DNA
<213> ORGANISM: Artificial sequence
<220> FEATURE:
<223> OTHER INFORMATION: Primer

<400> SEQUENCE: 3
gggtctagaa tgacctctcg ccgctccgt                              29

<210> SEQ ID NO 4
<211> LENGTH: 29
<212> TYPE: DNA
<213> ORGANISM: Artificial sequence
<220> FEATURE:
<223> OTHER INFORMATION: Primer

<400> SEQUENCE: 4
ggggaattcg tcctgcacca cgtctggat                              29

<210> SEQ ID NO 5
<211> LENGTH: 30
<212> TYPE: DNA
<213> ORGANISM: Artificial sequence
<220> FEATURE:
<223> OTHER INFORMATION: Primer

<400> SEQUENCE: 5
atcggatcca tggtgagcaa gggcgaggag                             30

<210> SEQ ID NO 6
<211> LENGTH: 30
<212> TYPE: DNA
<213> ORGANISM: Artificial sequence
<220> FEATURE:
<223> OTHER INFORMATION: Primer

<400> SEQUENCE: 6
gggaagcttt acttgtacag ctcgtccatg                             30

<210> SEQ ID NO 7
<211> LENGTH: 29
<212> TYPE: DNA
<213> ORGANISM: Artificial sequence
<220> FEATURE:
<223> OTHER INFORMATION: Primer

<400> SEQUENCE: 7
gggtctagaa tgacctctcg ccgctccgt                               29

<210> SEQ ID NO 8
<211> LENGTH: 29
<212> TYPE: DNA
<213> ORGANISM: Artificial sequence
<220> FEATURE:
<223> OTHER INFORMATION: Primer

<400> SEQUENCE: 8
ggggaattcc tcgacgggcc gtctggggc                               29

<210> SEQ ID NO 9
<211> LENGTH: 10
<212> TYPE: PRT
<213> ORGANISM: Artificial sequence
<220> FEATURE:
<223> OTHER INFORMATION: Synthetic sequence

<400> SEQUENCE: 9

Met Arg Lys Lys Arg Arg Gln Arg Arg Arg
1               5                   10

<210> SEQ ID NO 10
<211> LENGTH: 42
<212> TYPE: DNA
<213> ORGANISM: Artificial sequence
<220> FEATURE:
<223> OTHER INFORMATION: Primer

<400> SEQUENCE: 10
ctagaatgta cggccgcaag aaacgccgcc agcgccgccg cg                 42

<210> SEQ ID NO 11
<211> LENGTH: 42
<212> TYPE: DNA
<213> ORGANISM: Artificial sequence
<220> FEATURE:
<223> OTHER INFORMATION: Primer

<400> SEQUENCE: 11
aattcgcggc ggcgctggcg gcgtttcttg cggccgtaca tt                 42

<210> SEQ ID NO 12
<211> LENGTH: 12
<212> TYPE: PRT
<213> ORGANISM: Artificial sequence
<220> FEATURE:
<223> OTHER INFORMATION: Synthetic sequence

<400> SEQUENCE: 12

Ala Ala Val Leu Leu Pro Val Leu Leu Ala Ala Pro
1               5                   10

```
<210> SEQ ID NO 13
<211> LENGTH: 43
<212> TYPE: DNA
<213> ORGANISM: Artificial sequence
<220> FEATURE:
<223> OTHER INFORMATION: Primer

<400> SEQUENCE: 13
gatccgcagc cgttcttctc cctgttcttc ttgccgcacc cta            43

<210> SEQ ID NO 14
<211> LENGTH: 43
<212> TYPE: DNA
<213> ORGANISM: Artificial sequence
<220> FEATURE:
<223> OTHER INFORMATION: Primer

<400> SEQUENCE: 14
agcttagggt gcggcaagaa gaacagggag aagaacggct gcg            43

<210> SEQ ID NO 15
<211> LENGTH: 17
<212> TYPE: PRT
<213> ORGANISM: Artificial sequence
<220> FEATURE:
<223> OTHER INFORMATION: Synthetic sequence

<400> SEQUENCE: 15

Met Arg Gln Ile Lys Ile Trp Phe Gln Asn Arg Arg Met Lys Trp Lys
1               5                   10                  15

Lys

<210> SEQ ID NO 16
<211> LENGTH: 57
<212> TYPE: DNA
<213> ORGANISM: Artificial sequence
<220> FEATURE:
<223> OTHER INFORMATION: Primer

<400> SEQUENCE: 16
ctagaatgcg ccaaatcaaa atctggttcc agaatcgacg aatgaagtgg aaaaaag        57

<210> SEQ ID NO 17
<211> LENGTH: 57
<212> TYPE: DNA
<213> ORGANISM: Artificial sequence
<220> FEATURE:
<223> OTHER INFORMATION: Primer

<400> SEQUENCE: 17
aattcttttt tccacttcat tcgtcgattc tggaaccaga ttttgatttg gcgcatt        57

<210> SEQ ID NO 18
<211> LENGTH: 9
<212> TYPE: PRT
<213> ORGANISM: Artificial sequence
<220> FEATURE:
<223> OTHER INFORMATION: Synthetic sequence

<400> SEQUENCE: 18

Arg Lys Lys Arg Arg Gln Arg Arg Arg
1               5
```

```
<210> SEQ ID NO 19
<211> LENGTH: 16
<212> TYPE: PRT
<213> ORGANISM: Drosophila sp.

<400> SEQUENCE: 19

Arg Gln Ile Lys Ile Trp Phe Gln Asn Arg Arg Met Lys Trp Lys Lys
1               5                   10                  15

<210> SEQ ID NO 20
<211> LENGTH: 29
<212> TYPE: DNA
<213> ORGANISM: Artificial sequence
<220> FEATURE:
<223> OTHER INFORMATION: Primer

<400> SEQUENCE: 20
atctctagaa tggggattc tgaaaggcg                                         29

<210> SEQ ID NO 21
<211> LENGTH: 29
<212> TYPE: DNA
<213> ORGANISM: Artificial sequence
<220> FEATURE:
<223> OTHER INFORMATION: Primer

<400> SEQUENCE: 21
gatgaattct tcgctatcac tgctacgat                                        29

<210> SEQ ID NO 22
<211> LENGTH: 1257
<212> TYPE: DNA
<213> ORGANISM: Artificial sequence
<220> FEATURE:
<223> OTHER INFORMATION: Synthetic sequence - Plasmid pcDNA3-VP22/E7

<400> SEQUENCE: 22 atg acc tct cgc cgc tcc gtg aag tcg ggt ccg cgg gag gtt ccg cgc        48
Met Thr Ser Arg Arg Ser Val Lys Ser Gly Pro Arg Glu Val Pro Arg
1               5                   10                  15 gat gag tac gag gat ctg tac tac acc ccg tct tca ggt atg gcg agt        96
Asp Glu Tyr Glu Asp Leu Tyr Tyr Thr Pro Ser Ser Gly Met Ala Ser
                20                  25                  30 ccc gat agt ccg cct gac acc tcc cgc cgt ggc gcc cta cag aca cgc       144
Pro Asp Ser Pro Pro Asp Thr Ser Arg Arg Gly Ala Leu Gln Thr Arg
            35                  40                  45 tcg cgc cag agg ggc gag gtc cgt ttc gtc cag tac gac gag tcg gat       192
Ser Arg Gln Arg Gly Glu Val Arg Phe Val Gln Tyr Asp Glu Ser Asp
        50                  55                  60 tat gcc ctc tac ggg ggc tcg tct tcc gaa gac gac gaa cac ccg gag       240
Tyr Ala Leu Tyr Gly Gly Ser Ser Ser Glu Asp Asp Glu His Pro Glu
65                  70                  75                  80 gtc ccc cgg acg cgg cgt ccc gtt tcc ggg gcg gtt ttg tcc ggc ccg       288
Val Pro Arg Thr Arg Arg Pro Val Ser Gly Ala Val Leu Ser Gly Pro
                85                  90                  95 ggg cct gcg cgg gcg cct ccg cca ccc gct ggg tcc gga ggg gcc gga       336
Gly Pro Ala Arg Ala Pro Pro Pro Ala Gly Ser Gly Gly Ala Gly
                100                 105                 110 cgc aca ccc acc acc gcc ccc cgg gcc ccc cga acc cag cgg gtg gcg       384
Arg Thr Pro Thr Thr Ala Pro Arg Ala Pro Arg Thr Gln Arg Val Ala
            115                 120                 125 tct aag gcc ccc gcg gcc ccg gcg gcg gag acc acc cgc ggc agg aaa       432
Ser Lys Ala Pro Ala Ala Pro Ala Ala Glu Thr Thr Arg Gly Arg Lys
        130                 135                 140
```

```
tcg gcc cag cca gaa tcc gcc gca ctc cca gac gcc ccc gcg tcg acg    480
Ser Ala Gln Pro Glu Ser Ala Ala Leu Pro Asp Ala Pro Ala Ser Thr
145                 150                 155                 160 gcg cca acc cga tcc aag aca ccc gcg cag ggg ctg gcc aga aag ctg    528
Ala Pro Thr Arg Ser Lys Thr Pro Ala Gln Gly Leu Ala Arg Lys Leu
            165                 170                 175 cac ttt agc acc gcc ccc cca aac ccc gac gcg cca tgg acc ccc cgg    576
His Phe Ser Thr Ala Pro Pro Asn Pro Asp Ala Pro Trp Thr Pro Arg
                180                 185                 190 gtg gcc ggc ttt aac aag cgc gtc ttc tgc gcc gcg gtc ggg cgc ctg    624
Val Ala Gly Phe Asn Lys Arg Val Phe Cys Ala Ala Val Gly Arg Leu
            195                 200                 205 gcg gcc atg cat gcc cgg atg gcg gct gtc cag ctc tgg gac atg tcg    672
Ala Ala Met His Ala Arg Met Ala Ala Val Gln Leu Trp Asp Met Ser
210                 215                 220 cgt ccg cgc aca gac gaa gac ctc aac gaa ctc ctt ggc atc acc acc    720
Arg Pro Arg Thr Asp Glu Asp Leu Asn Glu Leu Leu Gly Ile Thr Thr
225                 230                 235                 240 atc cgc gtg acg gtc tgc gag ggc aaa aac ctg ctt cag cgc gcc aac    768
Ile Arg Val Thr Val Cys Glu Gly Lys Asn Leu Leu Gln Arg Ala Asn
                245                 250                 255 gag ttg gtg aat cca gac gtg gtg cag gac gtc gac gcg gcc acg gcg    816
Glu Leu Val Asn Pro Asp Val Val Gln Asp Val Asp Ala Ala Thr Ala
            260                 265                 270 act cga ggg cgt tct gcg gcg tcg cgc ccc acc gag cga cct cga gcc    864
Thr Arg Gly Arg Ser Ala Ala Ser Arg Pro Thr Glu Arg Pro Arg Ala
            275                 280                 285 cca gcc cgc tcc gct tct cgc ccc aga cgg ccc gtc gag ggt acc gag    912
Pro Ala Arg Ser Ala Ser Arg Pro Arg Arg Pro Val Glu Gly Thr Glu
290                 295                 300 ctc gga tcc atg cat gga gat aca cct aca ttg cat gaa tat atg tta    960
Leu Gly Ser Met His Gly Asp Thr Pro Thr Leu His Glu Tyr Met Leu
305                 310                 315                 320 gat ttg caa cca gag aca act gat ctc tac tgt tat gag caa tta aat   1008
Asp Leu Gln Pro Glu Thr Thr Asp Leu Tyr Cys Tyr Glu Gln Leu Asn
                325                 330                 335 gac agc tca gag gag gag gat gaa ata gat ggt cca gct gga caa gca   1056
Asp Ser Ser Glu Glu Glu Asp Glu Ile Asp Gly Pro Ala Gly Gln Ala
            340                 345                 350 gaa ccg gac aga gcc cat tac aat att gta acc ttt tgt tgc aag tgt   1104
Glu Pro Asp Arg Ala His Tyr Asn Ile Val Thr Phe Cys Cys Lys Cys
            355                 360                 365 gac tct acg ctt cgg ttg tgc gta caa agc aca cac gta gac att cgt   1152
Asp Ser Thr Leu Arg Leu Cys Val Gln Ser Thr His Val Asp Ile Arg
370                 375                 380 act ttg gaa gac ctg tta atg ggc aca cta gga att gtg tgc ccc atc   1200
Thr Leu Glu Asp Leu Leu Met Gly Thr Leu Gly Ile Val Cys Pro Ile
385                 390                 395                 400 tgt tct cag gat aag ctt aag ttt aaa ccg ctg atc agc ctc gac tgt   1248
Cys Ser Gln Asp Lys Leu Lys Phe Lys Pro Leu Ile Ser Leu Asp Cys
                405                 410                 415 gcc ttc tag                                                        1257
Ala Phe

<210> SEQ ID NO 23
<211> LENGTH: 418
<212> TYPE: PRT
<213> ORGANISM: Artificial sequence
<220> FEATURE:
<223> OTHER INFORMATION: Synthetic sequence encoded by pcDNA3-VP22/E7
      DNA
```

```
<400> SEQUENCE: 23

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
                100                 105                 110

Arg Thr Pro Thr Thr Ala Pro Arg Ala Pro Arg Thr Gln Arg Val Ala
                115                 120                 125

Ser Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
            195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
            275                 280                 285

Pro Ala Arg Ser Ala Ser Arg Pro Arg Arg Pro Val Glu Gly Thr Glu
    290                 295                 300

Leu Gly Ser Met His Gly Asp Thr Pro Thr Leu His Glu Tyr Met Leu
305                 310                 315                 320

Asp Leu Gln Pro Glu Thr Thr Asp Leu Tyr Cys Tyr Glu Gln Leu Asn
                325                 330                 335

Asp Ser Ser Glu Glu Glu Asp Glu Ile Asp Gly Pro Ala Gly Gln Ala
            340                 345                 350

Glu Pro Asp Arg Ala His Tyr Asn Ile Val Thr Phe Cys Cys Lys Cys
            355                 360                 365

Asp Ser Thr Leu Arg Leu Cys Val Gln Ser Thr His Val Asp Ile Arg
    370                 375                 380

Thr Leu Glu Asp Leu Leu Met Gly Thr Leu Gly Ile Val Cys Pro Ile
385                 390                 395                 400
```

```
Cys Ser Gln Asp Lys Leu Lys Phe Lys Pro Leu Ile Ser Leu Asp Cys
            405                 410                 415
Ala Phe

<210> SEQ ID NO 24
<211> LENGTH: 903
<212> TYPE: DNA
<213> ORGANISM: Herpes simplex virus-1

<400> SEQUENCE: 24
atgacctctc gccgctccgt gaagtcgggt ccgcgggagg ttccgcgcga tgagtacgag      60
gatctgtact acaccccgtc ttcaggtatg gcgagtcccg atagtccgcc tgacacctcc     120
cgccgtggcg ccctacagac acgctcgcgc cagaggggcg aggtccgttt cgtccagtac     180
gacgagtcgg attatgccct ctacggggc tcgtcttccg aagacgacga acacccggag      240
gtccccccgga cgcggcgtcc cgtttccggg cggttttgt ccggcccggg gcctgcgcgg      300
gcgcctccgc caccgctgg gtccgaggg gccggacgca cacccaccac cgccccccgg       360
gccccccgaa cccagcgggt ggcgtctaag gccccgcgg cccggcggc ggagaccacc      420
cgcggcagga atcggcccca gccagaatcc gccgcactcc cagacgcccc cgcgtcgacg     480
gcgccaaccc gatccaagac acccgcgcag gggctggcca gaaagctgca ctttagcacc     540
gccccccccaa accccgacgc gccatggacc ccccgggtgg ccggctttaa caagcgcgtc    600
ttctgcgccg cggtcgggcg cctggcggcc atgcatgccc ggatggcggc tgtccagctc    660
tgggacatgt cgcgtccgcg cacagacgaa gacctcaacg aactccttgg catcaccacc    720
atccgcgtga cggtctgcga gggcaaaaac ctgcttcagc gcgccaacga gttggtgaat    780
ccagacgtgg tgcaggacgt cgacgcgcc acggcgactc gagggcgttc tgcggcgtcg    840
cgccccaccg agcgacctcg agccccagcc cgctccgctt ctcgccccag acggcccgtc    900
gag                                                                   903

<210> SEQ ID NO 25
<211> LENGTH: 288
<212> TYPE: DNA
<213> ORGANISM: Artificial sequence
<220> FEATURE:
<223> OTHER INFORMATION: Synthetic sequence - part of HPV-16 E7 protein

<400> SEQUENCE: 25
atgcatggag atacacctac attgcatgaa tatatgttag atttgcaacc agagacaact      60
gatctctact gttatgagca attaaatgac agctcagagg aggaggatga aatagatggt     120
ccagctggac aagcagaacc ggacagagcc cattacaata ttgtaacctt ttgttgcaag    180
tgtgactcta cgcttcggtt gtgcgtacaa agcacacacg tagacattcg tactttggaa    240
gacctgttaa tgggcacact aggaattgtg tgccccatct gttctcag                288

<210> SEQ ID NO 26
<211> LENGTH: 301
<212> TYPE: PRT
<213> ORGANISM: Herpes simplex virus-1

<400> SEQUENCE: 26

Met Thr Ser Arg Arg Ser Val Lys Ser Gly Pro Arg Glu Val Pro Arg
1               5                   10                  15
Asp Glu Tyr Glu Asp Leu Tyr Tyr Thr Pro Ser Ser Gly Met Ala Ser
            20                  25                  30
```

```
Pro Asp Ser Pro Asp Thr Ser Arg Arg Gly Ala Leu Gln Thr Arg
            35                  40                  45
Ser Arg Gln Arg Gly Glu Val Arg Phe Val Gln Tyr Asp Glu Ser Asp
 50                  55                  60
Tyr Ala Leu Tyr Gly Gly Ser Ser Glu Asp Glu His Pro Glu
 65                  70                  75                  80
Val Pro Arg Thr Arg Arg Pro Val Ser Gly Val Leu Ser Gly Pro
                85                  90                  95
Gly Pro Ala Arg Ala Pro Pro Pro Ala Gly Ser Gly Gly Ala Gly
            100                 105                 110
Arg Thr Pro Thr Thr Ala Pro Arg Ala Pro Arg Thr Gln Arg Val Ala
            115                 120                 125
Ser Lys Ala Pro Ala Ala Pro Ala Ala Glu Thr Thr Arg Gly Arg Lys
130                 135                 140
Ser Ala Gln Pro Glu Ser Ala Ala Leu Pro Asp Ala Pro Ala Ser Thr
145                 150                 155                 160
Ala Pro Thr Arg Ser Lys Thr Pro Ala Gln Gly Leu Ala Arg Lys Leu
            165                 170                 175
His Phe Ser Thr Ala Pro Pro Asn Pro Asp Ala Pro Trp Thr Pro Arg
            180                 185                 190
Val Ala Gly Phe Asn Lys Arg Val Phe Cys Ala Val Gly Arg Leu
            195                 200                 205
Ala Ala Met His Ala Arg Met Ala Ala Val Gln Leu Trp Asp Met Ser
210                 215                 220
Arg Pro Arg Thr Asp Glu Asp Leu Asn Glu Leu Leu Gly Ile Thr Thr
225                 230                 235                 240
Ile Arg Val Thr Val Cys Glu Gly Lys Asn Leu Leu Gln Arg Ala Asn
            245                 250                 255
Glu Leu Val Asn Pro Asp Val Val Gln Asp Val Asp Ala Ala Thr Ala
            260                 265                 270
Thr Arg Gly Arg Ser Ala Ala Ser Arg Pro Thr Glu Arg Pro Arg Ala
            275                 280                 285
Pro Ala Arg Ser Ala Ser Arg Pro Arg Arg Pro Val Glu
290                 295                 300

<210> SEQ ID NO 27
<211> LENGTH: 98
<212> TYPE: PRT
<213> ORGANISM: Artificial sequence
<220> FEATURE:
<223> OTHER INFORMATION: Synthetic sequence - part of HPV-16 E7 protein

<400> SEQUENCE: 27

Met His Gly Asp Thr Pro Thr Leu His Glu Tyr Met Leu Asp Leu Gln
 1               5                  10                  15
Pro Glu Thr Thr Asp Leu Tyr Cys Tyr Glu Gln Leu Asn Asp Ser Ser
                20                  25                  30
Glu Glu Glu Asp Glu Ile Asp Gly Pro Ala Gly Gln Ala Glu Pro Asp
            35                  40                  45
Arg Ala His Tyr Asn Ile Val Thr Pro His Glu Cys Cys Lys Cys Asp
 50                  55                  60
Ser Thr Leu Arg Leu Cys Val Gln Ser Thr His Val Asp Ile Arg Thr
 65                  70                  75                  80
```

Leu Glu Asp Leu Leu Met Gly Thr Leu Gly Ile Val Cys Pro Ile Cys
            85                  90                  95

Ser Gln

<210> SEQ ID NO 28
<211> LENGTH: 249
<212> TYPE: PRT
<213> ORGANISM: Marek's disease virus-1

<400> SEQUENCE: 28

Met Gly Asp Ser Glu Arg Arg Lys Ser Glu Arg Arg Ser Leu Gly
1               5                   10                  15

Tyr Pro Ser Ala Tyr Asp Asp Val Ser Ile Pro Ala Arg Arg Pro Ser
            20                  25                  30

Thr Arg Thr Gln Arg Asn Leu Asn Gln Asp Asp Leu Ser Lys His Gly
        35                  40                  45

Pro Phe Thr Asp His Pro Thr Gln Lys His Lys Ser Ala Lys Ala Val
    50                  55                  60

Ser Glu Asp Val Ser Ser Thr Thr Arg Gly Gly Phe Thr Asn Lys Pro
65                  70                  75                  80

Arg Thr Lys Pro Gly Val Arg Ala Val Gln Ser Asn Lys Phe Ala Phe
                85                  90                  95

Ser Thr Ala Pro Ser Ser Ala Ser Ser Thr Trp Arg Ser Asn Thr Val
            100                 105                 110

Ala Phe Asn Gln Arg Met Phe Cys Gly Ala Val Ala Thr Val Ala Gln
        115                 120                 125

Tyr His Ala Tyr Gln Gly Ala Leu Ala Leu Trp Arg Gln Asp Pro Pro
    130                 135                 140

Arg Thr Asn Glu Glu Leu Asp Ala Phe Leu Ser Arg Ala Val Ile Lys
145                 150                 155                 160

Ile Thr Ile Gln Glu Gly Pro Asn Leu Met Gly Glu Ala Glu Thr Cys
                165                 170                 175

Ala Arg Lys Leu Leu Glu Glu Ser Gly Leu Ser Gln Gly Asn Glu Asn
            180                 185                 190

Val Lys Ser Lys Ser Glu Arg Thr Thr Lys Ser Glu Arg Thr Arg Arg
        195                 200                 205

Gly Gly Glu Ile Glu Ile Lys Ser Pro Asp Pro Gly Ser His Arg Thr
    210                 215                 220

His Asn Pro Arg Thr Pro Ala Thr Ser Arg Arg His His Ser Ser Ala
225                 230                 235                 240

Arg Gly Tyr Arg Ser Ser Asp Ser Glu
                245

<210> SEQ ID NO 29
<211> LENGTH: 750
<212> TYPE: DNA
<213> ORGANISM: Marek's disease virus-1

<400> SEQUENCE: 29
atgggggatt ctgaaaggcg gaaatcggaa cggcgtcgtt cccttggata tccctctgca      60
tatgatgacg tctcgattcc tgctcgcaga ccatcaacac gtactcagcg aaatttaaac     120
caggatgatt tgtcaaaaca tggaccattt accgaccatc caacacaaaa acataaatcg     180
gcgaaagccg tatcggaaga cgtttcgtct accacccggg gtggctttac aaacaaaccc     240
cgtaccaagc ccggggtcag agctgtacaa agtaataaat tcgctttcag tacggctcct     300

-continued

```
tcatcagcat ctagcacttg gagatcaaat acagtggcat ttaatcagcg tatgttttgc    360
ggagcggttg caactgtggc tcaatatcac gcataccaag gcgcgctcgc cctttggcgt    420
caagatcctc cgcgaacaaa tgaagaatta gatgcatttc tttccagagc tgtcattaaa    480
attaccattc aagagggtcc aaatttgatg ggggaagccg aaacctgtgc ccgcaaacta    540
ttggaagagt ctggattatc ccaggggaac gagaacgtaa agtccaaatc tgaacgtaca    600
accaaatctg aacgtacaag acgcggcggt gaaattgaaa tcaaatcgcc agatccggga    660
tctcatcgta cacataaccc tcgcactccc gcaacttcgc gtcgccatca ttcatccgcc    720
cgcggatatc gtagcagtga tagcgaataa                                     750
```